(12) United States Patent
Allen et al.

(10) Patent No.: US 12,397,079 B2
(45) Date of Patent: Aug. 26, 2025

(54) ULTRAVIOLET LIGHT DISINFECTION SYSTEM AND METHOD

(71) Applicant: CURRENT LIGHTING SOLUTIONS, LLC, East Cleveland, OH (US)

(72) Inventors: Gary R. Allen, Euclid, OH (US);
Kevin J. Benner, Solon, OH (US);
Stephen P. Glaudel, Hatfield, PA (US)

(73) Assignee: CURRENT LIGHTING SOLUTIONS, LLC, East Cleveland, OH (US)

( * ) Notice: Subject to any disclaimer, the term of this patent is extended or adjusted under 35 U.S.C. 154(b) by 0 days.

(21) Appl. No.: 17/475,973

(22) Filed: Sep. 15, 2021

(65) Prior Publication Data

US 2022/0001069 A1  Jan. 6, 2022

Related U.S. Application Data

(63) Continuation of application No. PCT/US2020/056991, filed on Oct. 23, 2020.
(Continued)

(51) Int. Cl.
*A61L 9/20* (2006.01)
*A61L 2/10* (2006.01)
*A61L 2/24* (2006.01)

(52) U.S. Cl.
CPC .......... *A61L 9/20* (2013.01); *A61L 2/10* (2013.01); *A61L 2/24* (2013.01); *A61L 2202/11* (2013.01);
(Continued)

(58) Field of Classification Search
CPC ...... A61L 2/10; A61L 2/24; A61L 9/20; A61L 2202/11; A61L 2202/14; A61L 2202/25; A61L 2209/111; A61L 2209/12
See application file for complete search history.

(56) References Cited

U.S. PATENT DOCUMENTS 8,398,264 B2  3/2013  Anderson et al.
9,039,966 B2  5/2015  Anderson et al.
(Continued)

OTHER PUBLICATIONS

Ebnesajjad, Sina. "Expanded PTFE Applications Handbook." William Andrew Publishing. Chapter 7. pp. 163-170. (Year: 2017).*
(Continued)

*Primary Examiner* — Timothy C Cleveland
(74) *Attorney, Agent, or Firm* — Lippes Mathias LLP

(57) ABSTRACT

A multispectral light source for disinfection is disclosed, including a plurality of light sources with different disinfection peak wavelengths and electronics. Each disinfection peak wavelength is effective for disinfection, and the electronics are configured to drive the plurality of light sources to emit light at the different disinfection peak wavelengths. In a specific embodiment, multispectral light source includes one or more UV-C light sources emitting ultraviolet light in a UV-C range, and one or more UV-A light sources emitting ultraviolet light in a UV-A range. The multispectral light source optionally may further include one or more white light sources emitting white light providing illumination. In a disinfection method, light in the UV-C range is emitted into an occupied space, and light outside of the UV-C range that is effective for inactivating at least one target pathogen is also emitted, optionally simultaneously, into the occupied space.

20 Claims, 29 Drawing Sheets

Related U.S. Application Data

(60) Provisional application No. 63/054,382, filed on Jul. 21, 2020, provisional application No. 63/047,722, filed on Jul. 2, 2020.

(52) U.S. Cl.
CPC ....... *A61L 2202/14* (2013.01); *A61L 2202/25* (2013.01); *A61L 2209/111* (2013.01); *A61L 2209/12* (2013.01)

(56) References Cited

U.S. PATENT DOCUMENTS

| | | | |
|---|---|---|---|
| 9,937,274 B2 | 4/2018 | Clynne et al. | |
| 9,981,052 B2 | 5/2018 | Clynne et al. | |
| 10,369,379 B2 | 8/2019 | Randers-Pehrson et al. | |
| 2007/0216472 A1 | 9/2007 | Stibich et al. | |
| 2007/0284315 A1 | 12/2007 | Collins et al. | |
| 2008/0305004 A1 | 12/2008 | Anderson et al. | |
| 2012/0238939 A1 | 9/2012 | Gerstenmeier | |
| 2015/0062893 A1* | 3/2015 | Lynn | F21V 7/00 362/231 |
| 2015/0086420 A1* | 3/2015 | Trapani | A61L 9/20 422/24 |
| 2016/0271281 A1 | 9/2016 | Clynne et al. | |
| 2017/0246329 A1* | 8/2017 | Lloyd | A61L 2/084 |
| 2018/0169279 A1 | 6/2018 | Randers-Pehrson et al. | |
| 2018/0339073 A1 | 11/2018 | Clynne et al. | |
| 2019/0328920 A1 | 10/2019 | Stibich et al. | |
| 2019/0347451 A1 | 11/2019 | Jinedatha | |
| 2023/0039310 A1* | 2/2023 | Baarman | A61L 9/20 |

OTHER PUBLICATIONS

Moreno et al. "Effects on illumination uniformity due to dilution on arrays of LEDs." Proceedings vol. 5529, Nonimaging Optics and Efficient Illumination Systems. 2004. 268-275. (Year: 2004).*

International Search Report mailed Mar. 23, 2021 for International application No. PCT/US2020/056991.

Written Option of the International Search Authority mailed Mar. 23, 2021 for International application No. PCT/US2020/056991.

Buonanno, Manuela et al., *"Far-UVC light (222 nm) efficiently and safely inactivates airborne"*, Scientific Reports (2020) 10:10285 https://doi.org/10.1038/s41598-020-67211-2.

Narita, Kouji, et al., publication titled "222-nm UVC inactivates a wide spectrum of microbial pathogens" Journal of Hospital Infection, https://doi.org/10.1016/j.jhin Mar. 30, 2020.

Tseng, Chun-Chieh et al. (2005), *"Inactivation of Virus-Containing Aerosols by Ultraviolet Germicidal Irradiation, Aerosol Science and Technology"*, 39:12, 1136-1142, DOI: 10.1080/02786820500428575, Published online: Feb. 23, 2007.

Buonanno, Manuela et al. *"Germicidal Efficacy and Mammalian Skin Safety of 222-nm UV Light"*, Radiat Res. Apr. 2017 ; 187(4): 483-491, doi:10.1667/ RR0010CC.1.

* cited by examiner

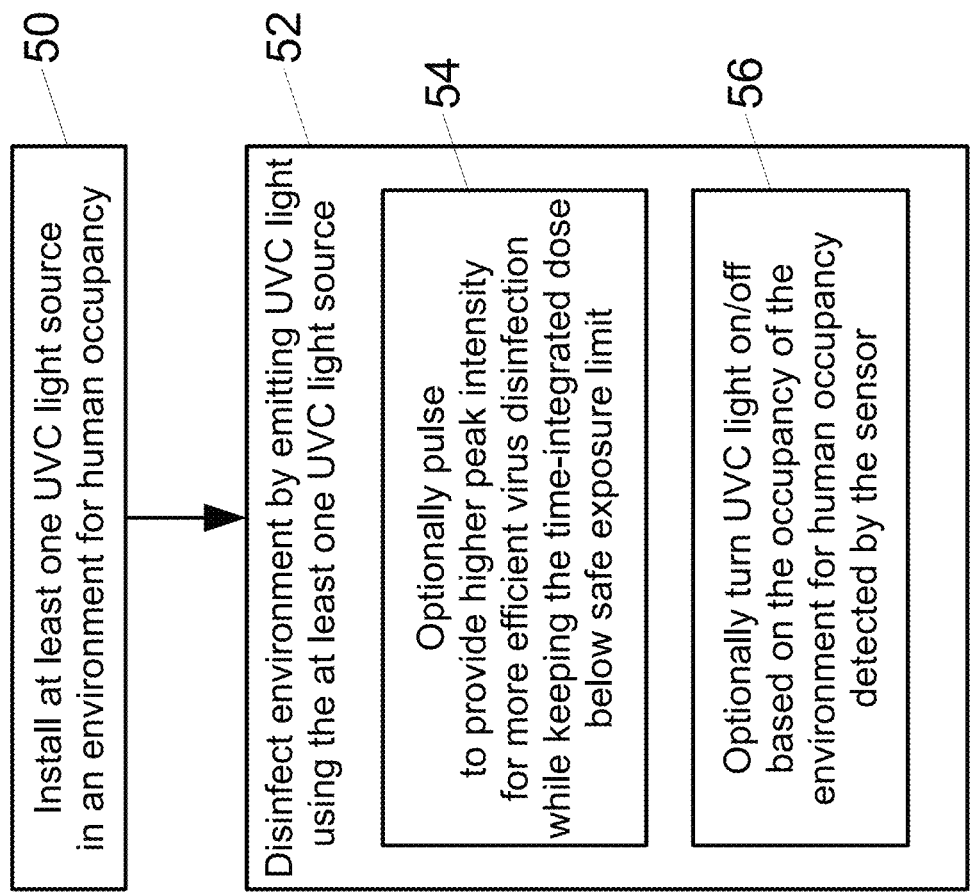

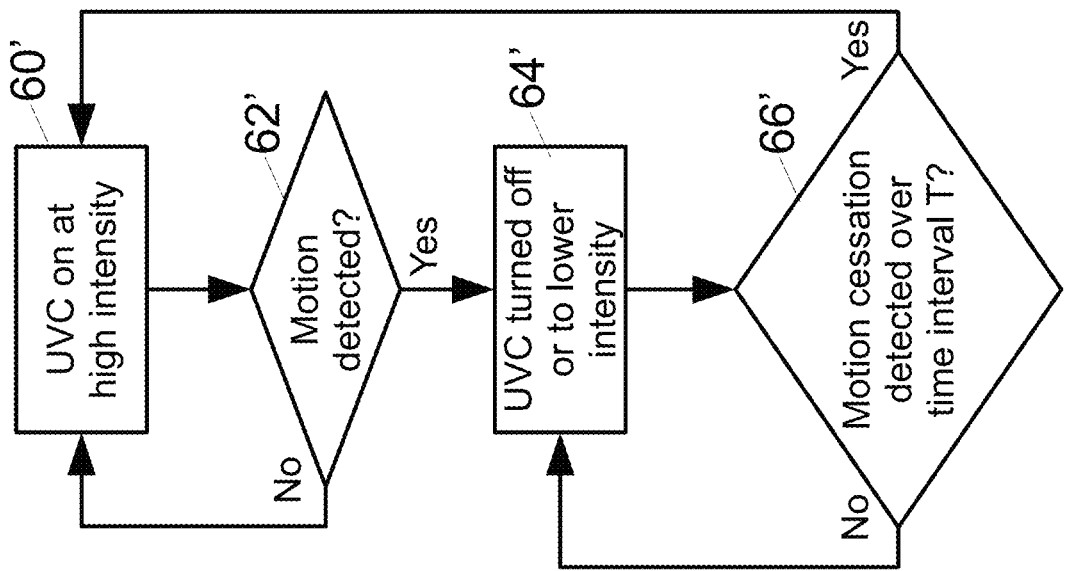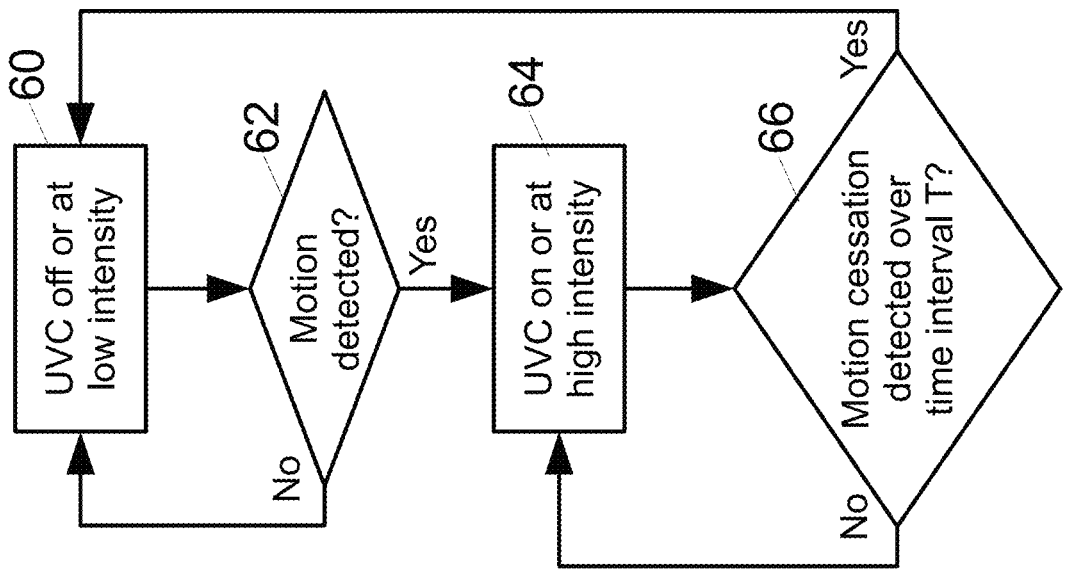
Fig. 5

Table 1: Geometric Means of log10 kill of viruses at 254 nm in air

| Virus in Air | Type | D90 | log10 kill @60 $J/m^2$ | |
|---|---|---|---|---|
| | | $J/m^2$ | min | max |
| Adenovirus | dsDNA | 44 | 0.8 | 1.4 |
| Bacteriophage MS2 | ssRNA | 12 | 1.5 | 5.1 |
| Coliphage T7 | dsDNA | 8 | 1.4 | 7.2 |
| Coliphage φX-174 | ssDNA | 3 | 3.5 | 17 |
| Coronavirus | ssRNA | 3 | 2.0 | 20 |
| Coxsackievirus | ssRNA | 21 | 2.9 | 2.9 |
| Influenza A | ssRNA | 19 | 3.2 | 3.2 |
| phage phi 6 | dsRNA | 6 | 2.0 | 10 |
| Sindbis virus | ssRNA | 22 | 2.7 | 2.7 |
| Vaccinia virus | dsDNA | 4 | 3.5 | 15 |

| | | | |
|---|---|---|---|
| Geometric Mean of D90's | 10 | 2.1 | 6.1 |

| | | |
|---|---|---|
| % Pathogens with at least 99% kill | 60% | 90% |

Fig. 15

Table 2: Geometric Means of log10 kill of viruses at 254 nm on surfaces

| Virus on Surfaces | Type | D90 J/m² | log10 kill @254 nm min | log10 kill @254 nm max |
|---|---|---|---|---|
| Adenovirus | dsDNA | 307 | 0.2 | 0.2 |
| Coliphage PRD1 | dsDNA | 87 | 0.7 | 0.7 |
| Human Cytomegalovirus | dsDNA | 181 | 0.3 | 0.3 |
| Newcastle Disease | ssRNA | 16 | 3.1 | 3.8 |
| Poliovirus | dsRNA | 42 | 1.4 | 1.4 |
| Rauscher Murine Leukemia | ssRNA | 959 | 0.1 | 0.1 |
| Rous Sarcoma | ssRNA | 200 | 0.3 | 0.3 |
| S. aureus phage | dsDNA | 79 | 0.1 | 0.8 |

| Geometric Mean of D90's | 122 | 0.4 | 0.5 |
|---|---|---|---|

| % Pathogens with at least 99% kill | 13% | 13% |
|---|---|---|

Fig. 16

Table 3: Geometric Means of log10 kill of bacteria at 254 nm in air

| Bacteria in Air | Type | D90 $J/m^2$ | log10 kill @60 $J/m^2$ min | log10 kill @60 $J/m^2$ max |
|---|---|---|---|---|
| B. atrophaeus (B. globigii) | Sp | 144 | | 0.4 |
| Bacillus subtilis | Veg | 14 | 4.3 | 4.3 |
| Bacillus subtilis | Sp | 104 | 0.5 | 0.6 |
| Escherichia coli | Veg | 8 | 0.3 | 7.8 |
| Francisella tularensis | Veg | 272 | 0.0 | 0.2 |
| Mycobacterium bovis | Veg | 17 | 0.4 | 3.6 |
| Mycobacterium parafortuitum | Veg | 22 | 1.8 | 2.7 |
| Mycobacterium phlei | Veg | 29 | 0.1 | 2.1 |
| Mycobacterium smegmatis | Veg | 12 | | 5.0 |
| Mycobacterium tuberculosis | Veg | 5 | 1.0 | 12 |
| Pseudomonas aeruginosa | Veg | 4 | 15 | 15 |
| Pseudomonas fluorescens | Veg | 3 | 4.3 | 20 |
| Serratia indica | Veg | 209 | 0.3 | 0.3 |
| Serratia marcescens | Veg | 7 | 2.5 | 8.1 |
| Staphylococcus albus | Veg | 35 | 0.1 | 1.7 |
| Staphylococcus aureus | Veg | 5 | 3.4 | 12.3 |
| Staphylococcus epidermis | Veg | 21 | 1.2 | 2.9 |
| Streptococcus agalactiae | Veg | 5 | 1.4 | 12 |
| Streptococcus pyogenes | Veg | 1 | 2.0 | 60 |
| Geometric Mean of D90's | | 16 | 0.8 | 3.7 |
| % Pathogens with at least 99% kill | | | 29% | 74% |

Fig. 17

Table 4: Geometric Means of log10 kill of bacteria at 254 nm on surfaces

| Bacteria on Surfaces | Type | D90 J/m² | log10 kill @60 J/m² min | log10 kill @60 J/m² max |
|---|---|---|---|---|
| Acinetobacter baumannii | Veg | 18 | 3.3 | 3.3 |
| Bacillus anthracis | Sp | 183 | 0.3 | 0.3 |
| Bacillus cereus | Sp | 227 | | 0.3 |
| Bacillus megatherium | Veg | 113 | | 0.5 |
| Bacillus megatherium | Sp | 273 | | 0.2 |
| Bacillus subtilis | Sp | 90 | 0.6 | 0.7 |
| Corynebacterium diphtheriae | Veg | 33 | 1.4 | 1.8 |
| Escherichia coli | Veg | 23 | 1.2 | 2.6 |
| Haemophilus influenzae | Veg | 38 | 0.4 | 1.6 |
| Halobacterium sp. | Veg | 25 | 2.4 | 2.4 |
| Legionella bozemanii | Veg | 15 | 4.0 | 4.0 |
| Legionella dumoffi | Veg | 24 | 2.5 | 2.5 |
| Legionella gormanii | Veg | 26 | 2.3 | 2.3 |
| Legionella jordanis | Veg | 11 | 5.5 | 5.5 |
| Legionella longbeach | Veg | 11 | 5.5 | 5.5 |
| Legionella mcdadei | Veg | 15 | 4.0 | 4.0 |
| Legionella oakridgensis | Veg | 10 | 5.7 | 5.7 |
| Legionella wadsworthii | Veg | 4 | 15 | 15 |
| Listeria monocytogenes | Veg | 39 | 1.4 | 1.5 |
| Micrococcus candidus | Veg | 61 | | 1.0 |
| Micrococcus piltonensis | Veg | 81 | 0.7 | 0.7 |
| Micrococcus sphaeroides | Veg | 100 | 0.6 | 0.6 |
| Mycobacterium bovis BCG | Veg | 22 | 2.2 | 2.7 |
| Mycobacterium tuberculosis | Veg | 11 | 4.4 | 5.5 |

Fig. 18

Table 4: (continued)

| Bacteria on Surfaces | Type | D90 J/m² | log10 kill @60 J/m² min | log10 kill @60 J/m² max |
|---|---|---|---|---|
| Mycoplasma arthritidis | Veg | 7 | 3.1 | 8.6 |
| Mycoplasma fermentans | Veg | 9 | 2.4 | 8.7 |
| Mycoplasma hominis | Veg | 7 | 3.1 | 8.6 |
| Mycoplasma Orale | Veg | 8 | 2.7 | 7.4 |
| Mycoplasma pneumoniae | Veg | 8 | 2.8 | 7.5 |
| Mycoplasma salivarium | Veg | 11 | 2.0 | 5.5 |
| Neisseria catarrhalis | Veg | 44 | 1.4 | 1.4 |
| Nocardia asteroides | Veg | 260 | 0.2 | 0.2 |
| Phytomonas | Veg | 44 | 1.4 | 1.4 |
| Proteus vulgaris | Veg | 30 | 2.0 | 2.0 |
| Pseudomonas aeruginosa | Veg | 23 | 2.1 | 2.6 |
| Pseudomonas fluorescens | Veg | 35 | 1.7 | 1.7 |
| Salmonella enteritidis | Veg | 10 | 4.6 | 6.0 |
| Salmonella typhi | Veg | 21 | 1.9 | 2.9 |
| Sarcina lutea | Veg | 197 | 0.3 | 0.3 |
| Serratia marcescens | Veg | 14 | 2.9 | 4.3 |
| Shigella paradysenteriae | Veg | 17 | 2.4 | 3.5 |
| Spirillum rubrum | Veg | 44 | 1.4 | 1.4 |
| Staphylococcus albus | Veg | 18 | 1.4 | 3.3 |
| Staphylococcus aureus | Veg | 35 | 0.7 | 1.7 |
| Streptococcus haemolyticus | Veg | 22 | 1.6 | 2.7 |
| Streptococcus lactis | Veg | 62 | 1.0 | 1.0 |
| Streptococcus pneumoniae | Veg | 468 | 0.1 | 0.1 |
| Streptococcus pyogenes | Veg | 4 | 1.5 | 1.5 |
| Streptococcus viridans | Veg | 20 | 1.6 | 3.0 |

| Geometric Mean of D90's | 28.7 | 1.8 | 2.1 |
|---|---|---|---|
| % Pathogens with at least 99% kill | | 49% | 57% |

Fig. 19

Table 5: Summary of % of pathogen species that are inactivated by at least 99% by 60 J/m2 @ 254 nm

| | Air | Surface |
|---|---|---|
| Viruses | 60-90% | 13% |
| Bacteria | 29-74% | 49-57% |

Fig. 20

Table 6: compilation of the inactivation data from SARS CoV-2 references

| Reference | Medium | As measured D90 [J/m²] |
|---|---|---|
| Patterson | Aqueous | 88 |
| Bianco | Aqueous | 22 |
| BU-Signify | Surfaces | 25 |
| Inagaki | Aqueous @280 nm | 42 |
| Kitigawa | Surface @222 nm | 11 |
| Heilingloh | Aqueous | 776 |

Fig. 21

Table 7: Excerpt of UV Rate Constant data @ 254nm for various viruses as a function of relative humidity, with water in the limit

| | | k [$m^2/J$] | | | | | | |
|---|---|---|---|---|---|---|---|---|
| Microbe | Type | <68%RH | >75%RH | avg RH | Water | Water/Avg RH | Reference | |
| Adenovirus | dsDNA | 0.039 | 0.068 | 0.0535 | 0.006 | 0.11 | Walker | -2007 |
| Vaccinia | dsDNA | 6.01 | 1.42 | 3.715 | 0.134 | 0.04 | McDevitt | -2007 |
| phage T7 | dsDNA | 0.33 | 0.22 | 0.275 | 0.082 | 0.30 | Tseng | -2005 |
| phage phi 6 | dsRNA | 0.43 | 0.31 | 0.37 | - | | Tseng | -2005 |
| phage phi X174 | ssDNA | 0.71 | 0.53 | 0.62 | 0.111 | 0.18 | Tseng | -2005 |
| Coronavirus | ssRNA | 0.377 | - | 0.377 | 0.149 | 0.40 | Walker | -2007 |
| MS2 | ssRNA | 0.038 | 0.048 | 0.043 | 0.013 | 0.30 | Walker | -2007 |
| MS2 | ssRNA | 0.81 | 0.64 | 0.725 | 0.013 | 0.02 | Tseng | -2005 |
| Geometric Mean Water/RH | | | | | | 0.12 | | |

Table 8: Summary of Inactivation of Viruses and Bacteria in Air and on Surfaces, including Coronavirus and SAR CoV-2

| Reference | Medium | D90 [J/m$^2$] as measured | D90 [J/m$^2$] estimated in Air at measured wavelength | Uracil absorbance at measured wavelength | D90 [J/m$^2$] estimated in Air @ 254 nm |
|---|---|---|---|---|---|
| Patterson | Aqueous | 88 | 11 | 7.9 | 11 |
| Bianco | Aqueous | 22 | 2.8 | 7.9 | 2.8 |
| BU-Signify | Surfaces | 25 | 2.5 | 7.9 | 2.5 |
| Inagaki | Aqueous @280 nm | 42 | 5.2 | 2.2 | 1.4 |
| Kitigawa | Surface @222 nm | 11 | 1.1 | 2.8 | 0.4 |
| Heilingloh | Aqueous | 776 | 97 | 7.9 | 97 |
| | | | | Geometric Mean, all 6 D90's | 4.0 |
| | | | | Geometric Mean, omitting high outlier | 2.1 |
| | | | | Geometric Mean, omitting high & low outliers | 3.2 |
| | | | | Geometric Mean, omitting all 3 outliers | 2.1 |

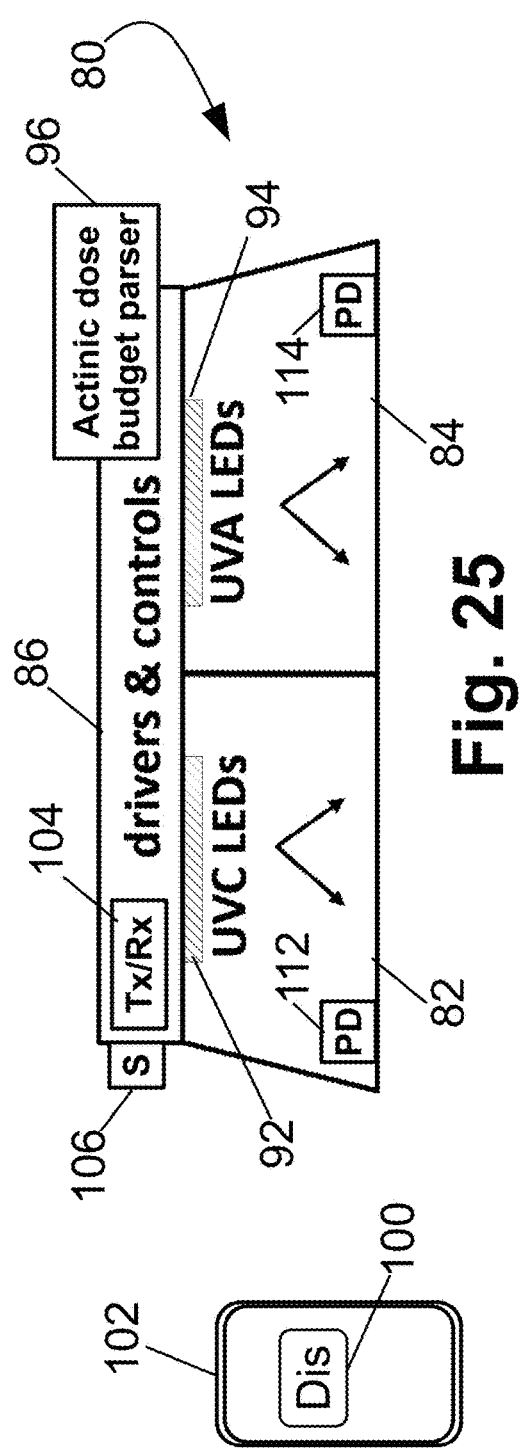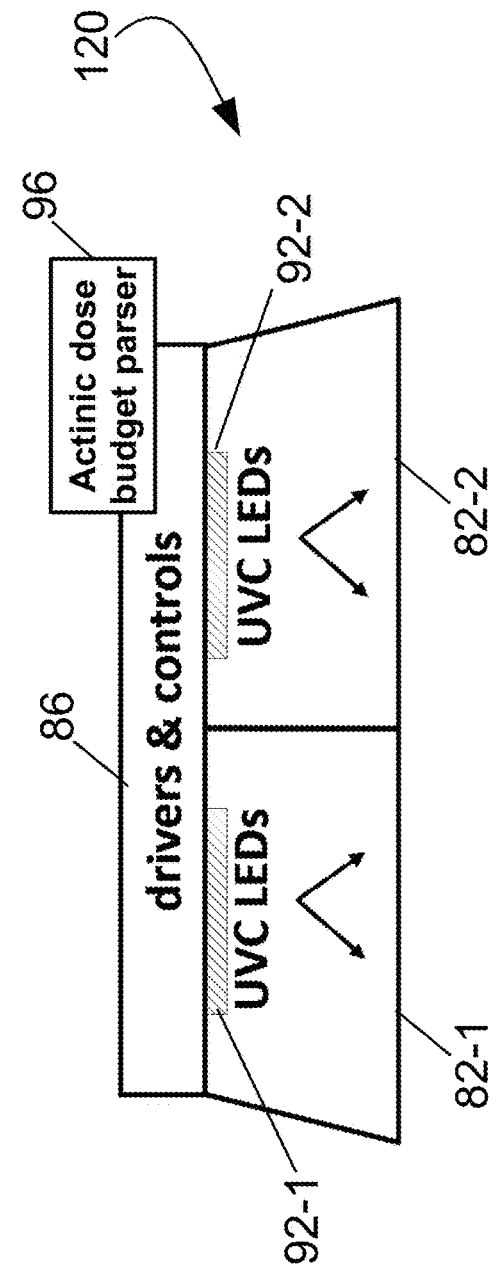

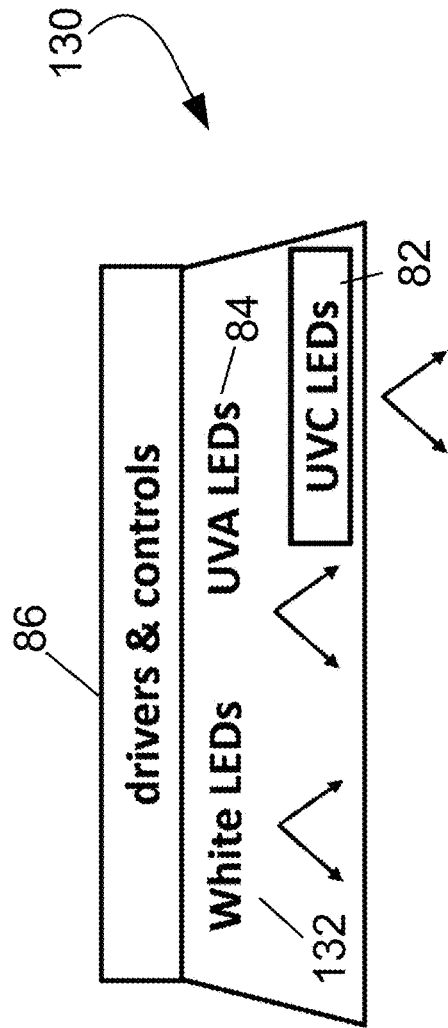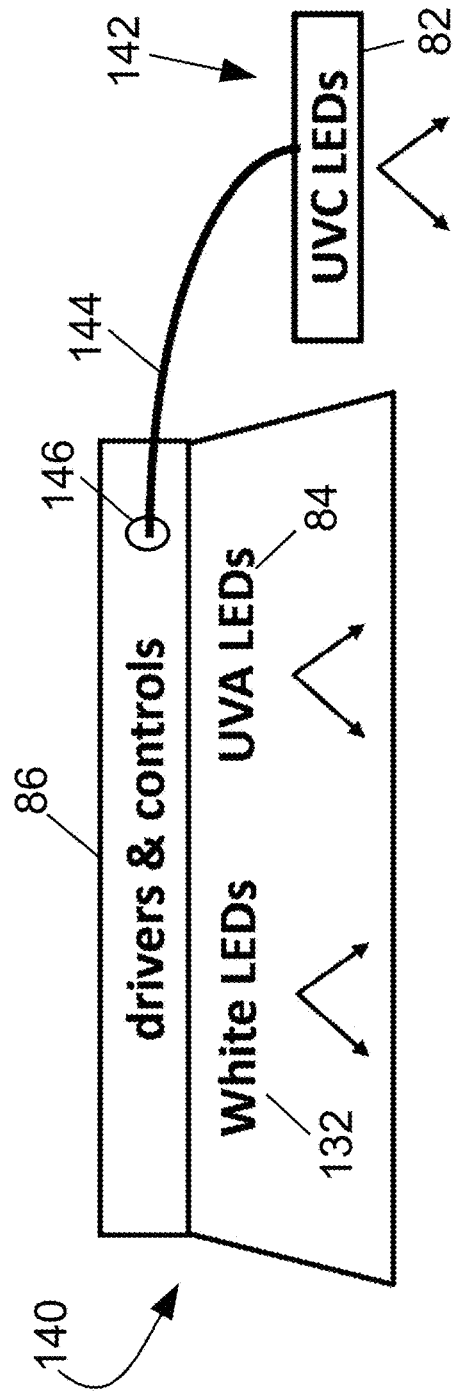

| D90 [J/m²] | 254 nm ||
|---|---|---|
| | Water/Surface | Air Lo/Hi RH |
| Virus | 40/73 | 6/8 |
| Bacteria veg. | 27/16 | 6/31 |
| Bacterial Spores | 160/126 | 90/89 |
| Fungi veg. | 229/329 | 23/- |
| Fungal Spores | 251/292 | 315/488 |

Fig. 31

| from 2013 Santos (aqueous) | D90 [J/m²] | | | Actinic EL [J/m²] | | |
|---|---|---|---|---|---|---|
| | 365 nm | 302 nm | 254 nm | 272,727 | 182 | 60 |
| Bacterium (veg) | | | | log10 inactivation at EL | | |
| | | | | 365 nm | 302 nm | 254 nm |
| Acinetobacter | 528,187 | 113,278 | 60 | 0.5 | 0.002 | 1.0 |
| Bacillus | 508,255 | 113,278 | 104 | 0.5 | 0.002 | 0.6 |
| Brevibacterium | 172,408 | 126,565 | 54 | 1.6 | 0.001 | 1.1 |
| Micrococcus | 986,613 | 166,429 | 149 | 0.3 | 0.001 | 0.4 |
| Paracoccus | 946,750 | 133,874 | 46 | 0.3 | 0.001 | 1.3 |
| Pseudomonas | 734,146 | 163,771 | 135 | 0.4 | 0.001 | 0.4 |
| Psychrobacter | 757,400 | 98,329 | 55 | 0.4 | 0.002 | 1.1 |
| Sphingomonas | 966,681 | 130,220 | 135 | 0.3 | 0.001 | 0.4 |
| Staphylococcus | 458,426 | 122,911 | 58 | 0.6 | 0.001 | 1.0 |
| Geometric Mean D50 | 603,712 | 128,158 | 80 | 0.5 | 0.00 | 0.8 |

| from 2020 Brons (dry) | | | | | | |
|---|---|---|---|---|---|---|
| S. aureus | 18,602 | | | 4.4 | | |

| from 2020 Kvam (dry) | | | | | | |
|---|---|---|---|---|---|---|
| S. aureus | 10,309 | | | 8.0 | | |
| E. faecalis | 13,790 | | | 6.0 | | |
| E. coli | 23,358 | | | 3.5 | | |

Fig. 33

ULTRAVIOLET LIGHT DISINFECTION SYSTEM AND METHOD

This application is a Continuation of PCT/US2020/056991 filed Oct. 23, 2020 titled "MULTISPECTRAL LIGHT DISINFECTION SYSTEM AND METHOD", which claims the benefit of U.S. Provisional Application No. 63/054,382 filed Jul. 21, 2020 titled "MULTISPECTRAL LIGHT DISINFECTION SYSTEM AND METHOD", and which claims the benefit of U.S. Provisional Application No. 63/047,722 filed Jul. 2, 2020 titled "LIGHT DISINFECTION SYSTEM AND METHOD". U.S. Provisional Application No. 63/054,382 filed Jul. 21, 2020 is incorporated herein by reference in its entirety. U.S. Provisional Application No. 63/047,722 filed Jul. 2, 2020 is incorporated herein by reference in its entirety.

BACKGROUND

The following relates to the disinfection arts, pathogen control arts, viral pathogen control arts, lighting arts, and the like.

Clynne et al., U.S. Pat. No. 9,937,274 B2 issued Apr. 10, 2018 and Clynne et al., U.S. Pat. No. 9,981,052 B2 (which is a continuation of U.S. Pat. No. 9,937,274) provide, in some illustrative examples, disinfection systems that include a light source configured to generate ultraviolet light toward one or more surfaces or materials to inactivate one or more pathogens on the one or more surfaces or materials.

U.S. Pub. No. 2016/0271281 A1 is the published application corresponding to U.S. Pat. No. 9,937,274. U.S. Pub. No. 2016/0271281 A1 is incorporated herein by reference in its entirety to provide general information on disinfection systems for occupied spaces that use ultraviolet light.

Moreno, "Effects on illumination uniformity due to dilution on arrays of LEDs", 2004 Proceedings of SPIE, provides an approach for computing the spatial distribution of irradiance from a light emitting diode (LED) on a plane illuminated by the LED.

Wladyslaw Kowalski, ULTRAVIOLET GERMICIDAL IRRADIATION HANDBOOK (Springer-Verlag Berlin Heidelberg 2009) (hereinafter "Kowalski 2009") provides information for estimating rate constants for inactivation of pathogens.

Certain improvements are disclosed.

BRIEF DESCRIPTION

In some illustrative embodiments disclosed herein, a multispectral light source for disinfection is disclosed. The multispectral light source includes: a plurality of light sources (e.g., outputting in the ultraviolet, visible, or infrared range, or more generally outputting non-ionizing electromagnetic radiation) with different disinfection peak wavelengths where each disinfection peak wavelength is effective for disinfection; and electronics configured to drive the plurality of light sources to emit light at the different disinfection peak wavelengths. In some embodiments, the multispectral light source is configured to emit light into an environment for human occupancy to inactivate one or more pathogens in the environment for human occupancy, and the irradiation of the light emitted into the environment for human occupancy by the multispectral light source is effective to achieve at least 90% inactivation of the one or more pathogens in the environment within 8 hours or less. In some embodiments, the plurality of light sources with different disinfection peak wavelengths include at least one UV-A light source with a disinfection peak wavelength in the UV-A range and at least one UV-C light source with a disinfection peak wavelength in the UV-C range. The multispectral light source optionally may further include one or more white light sources emitting white light providing illumination. In some embodiments, the multispectral light source does not include a UV-B light source emitting in the UV-B range. In some embodiments, the electronics include an actinic dose budget parser configured to control the plurality of sets of LEDs to emit the different disinfection peak wavelengths to output a predetermined spectrum optimized to inactivate a specific target pathogen or class of pathogens or multiple classes of pathogens. In some embodiments, the different disinfection peak wavelengths are discrete peak wavelengths having relatively narrow emission bands having FWHM about 10 nm (in the case of an LED or laser diode, or possibly narrower in the case of a Hg, Xe, or excimer discharge lamp), each disinfection peak wavelength thus including emission covering a band of about 30-50 nm or less adjacent to the peak wavelength, and a total emission intensity of the multispectral light source outside of the discrete peaks and their adjacent bands is less than 40% of the total intensity emitted by the multispectral light source. In some embodiments, the plurality of light sources with different disinfection peak wavelengths comprise a plurality of sets of LEDs where each set of LEDs includes one or more LEDs emitting at a respective disinfection peak wavelength, and the electronics include an actinic dose budget parser comprising an electronic processor programmed to control the plurality of sets of LEDs to emit the different disinfection peak wavelengths to output a predetermined spectrum optimized to inactivate a specific target pathogen or class of pathogens or classes of pathogens.

In some illustrative embodiments disclosed herein, a multispectral light source for disinfection is disclosed. The multispectral light source includes one or more UV-C light sources emitting ultraviolet light in a UV-C range, and one or more UV-A light sources emitting ultraviolet light in a UV-A range. The multispectral light source optionally may further include one or more white light sources emitting white light providing illumination. For example, the multispectral light source may further include a single fixture in which the one or more UV-C light sources, the one or more UV-A light sources, and the (optional) white light sources are mounted. Alternatively, the multispectral light source may further include a main fixture in which the one or more UV-A light sources and the (optional) white light sources are mounted, and an auxiliary fixture in which the one or more UV-C light sources are mounted. In the latter embodiments, the main fixture may include a connector via which the auxiliary fixture is connected to receive electrical power from the main fixture. In any of the foregoing variants, the multispectral light source may optionally further include electronics (and optionally sensors) programmed to control the one or more UV-C light sources and the one or more UV-A light sources to control a total actinic dose emitted by the combination of the one or more UV-C light sources and the one or more UV-A light sources.

In some illustrative embodiments disclosed herein, a disinfection method includes: emitting light in the UV-C range that is effective for inactivating at least one target pathogen into an occupied space; and emitting light outside of the UV-C range that is effective for inactivating the at least one target pathogen into the occupied space. In some embodiments, the emitting of the light outside of the UV-C range that is effective for inactivating the at least one target pathogen into the occupied space comprises emitting light in the UV-A range into the occupied space. In some embodiments, the emitting of the light outside of the UV-C range that is effective for inactivating the at least one target pathogen into the occupied space comprises emitting light in the violet or other visible range into the occupied space. In some embodiments, the emitting of the light outside of the UV-C range that is effective for inactivating the at least one target pathogen into the occupied space comprises emitting light in the infrared range into the occupied space. In any of the foregoing variants, in some more specific embodiments the emitting of the UV-C light into the occupied space and the emitting of the light outside of the UV-C range that is effective for inactivating the at least one target pathogen into the occupied space may be performed simultaneously or sequentially, or a combination.

In some illustrative embodiments disclosed herein, a disinfection system includes at least one light source configured to emit light into an environment for human occupancy to inactivate one or more pathogens in the environment for human occupancy. The light includes an inactivating portion in a range of 200 nanometers to 280 nanometers inclusive. In some embodiments, the light emitted by the at least one light source is effective to produce an actinic dose at a target plane in the environment of 30 J/m$^2$ or less over an eight hour period, wherein the target plane is two meters or closer to a floor of the environment for human occupancy.

In some illustrative embodiments disclosed herein, a viral disinfection light source comprises a light source including a lamp or one or more LEDs disposed on a substrate. The light source is configured to emit light including an inactivating portion having peak wavelength in a range of 200 nanometers to 280 nanometers inclusive.

In some illustrative embodiments disclosed herein, a multispectral light source for disinfection is disclosed. The multispectral light source comprises: a plurality of light sources with different peak wavelengths including at least one ultraviolet light source whose peak wavelength is in the ultraviolet range; and electronics configured to drive the plurality of light sources to emit disinfection light producing an actinic dose that is below a dose limit for actinic radiation exposure. In some embodiments of the multispectral light source, the dose limit is defined for a time frame of an eight hour period. In some embodiments of the multispectral light source, the dose limit is defined for a time frame of a twenty-four hour period. In some embodiments of the multispectral light source, the actinic dose $D_{act}$ is $D_{act}=\Sigma_{i=1}^{N}k_{act,i}H_i$ where i=1, . . . , N indexes the light sources of the plurality of ultraviolet light sources, $H_i$ is a radiant dose produced by light source i, and $k_{act,i}$ is an actinic hazard coefficient at the peak wavelength of the light source i. In some embodiments of the multispectral light source, the at least one ultraviolet light source includes at least one UV-C light source whose peak wavelength is in the UV-C range, and in some such embodiments the at least one ultraviolet light source may further include at least one UV-A light source whose peak wavelength is in the UV-A range, and/or at least one violet light source whose peak wavelength is greater than 380 nm and less than or equal to 450 nm. In some embodiments of the multispectral light source, the electronics are further configured to adjust relative intensities of the light sources of the plurality of light sources while keeping the actinic dose of the emitted disinfection light below the dose limit.

In some illustrative embodiments disclosed herein, a multispectral light source for disinfection is disclosed. The multispectral light source comprises: a plurality of light sources with different peak wavelengths including at least one ultraviolet light source whose peak wavelength is in the ultraviolet range; and electronics configured to drive the plurality of light sources to emit disinfection light producing an actinic dose that is below a dose limit for actinic radiation exposure. The electronics are further configured to adjust actinic dose fractions of the light sources of the plurality of light sources while keeping the actinic dose of the emitted disinfection light below the dose limit. In some embodiments, the actinic dose $D_{act}$ is $D_{act}=\Sigma_{i=1}^{N}k_{act,i}H_i$ where i=1, N indexes the light sources of the plurality of ultraviolet light sources, $H_i$ is a radiant dose produced by light source i, and $k_{act,i}$ is an actinic hazard coefficient at the peak wavelength of the light source i, and $k_{act,i} H_i$ is the actinic dose fraction of the light source i.

In some illustrative embodiments disclosed herein, a multispectral light source for disinfection is disclosed. The multispectral light source comprises: at least one UV-C light source configured to emit ultraviolet light whose peak wavelength is in the UV-C range; and at least one non-UV-C light source configured to emit light whose peak wavelength is outside of the UV-C range. In some embodiments, the at least one non-UV-C light source includes a UV-A light source configured to emit ultraviolet light whose peak wavelength is in the UV-A range. In some embodiments, the at least one non-UV-C light source includes at least one light source configured to emit light whose peak wavelength is in the visible or infrared range.

In some illustrative embodiments disclosed herein, a disinfection method comprises: inactivating a first target pathogen by emitting first light whose peak wavelength is in the UV-C range into an occupied space; and inactivating a second target pathogen by emitting second light whose peak wavelength is outside of the UV-C range into the occupied space. In some embodiments, the peak wavelength of the second light is in the UV-A range. In some embodiments, the peak wavelength of the second light is in the violet and/or infrared range. In some embodiments, the first target pathogen is a viral pathogen and the second target pathogen is a bacterial pathogen. The first target pathogen may in some embodiments be the same as the second target pathogen. The first target pathogen may in some embodiments be different from the second target pathogen. In some embodiments, the emitting of the first light into the occupied space and the emitting of the second light into the occupied space are performed simultaneously.

In some illustrative embodiments disclosed herein, a disinfection system comprises at least one light source configured to emit light into an environment for human occupancy to inactivate one or more pathogens in the environment for human occupancy, the light including an inactivating portion in a range of 240 nanometers to 280 nanometers. The light emitted by the at least one light source is effective to produce an actinic dose at a target plane in the environment of 30 J/m$^2$ or less over a twenty-four hour period, where the target plane is a horizontal plane 2.1 meters or more from a floor of the environment for human occupancy.

In some illustrative embodiments disclosed herein, a disinfection method comprises emitting light into an environment for human occupancy to inactivate one or more pathogens in the environment for human occupancy, the light including an inactivating portion in a range of 240 nanometers to 280 nanometers. The emitted light is effective to produce an actinic dose at a target plane in the environment of 30 J/m$^2$ or less over a twenty-four hour period, where the target plane is a horizontal plane 2.1 meters or more from a floor of the environment for human occupancy

BRIEF DESCRIPTION OF THE DRAWINGS

The following is a brief description of the drawings, which are presented for the purposes of illustrating the exemplary embodiments disclosed herein and not for the purposes of limiting the same.

Figure 2:
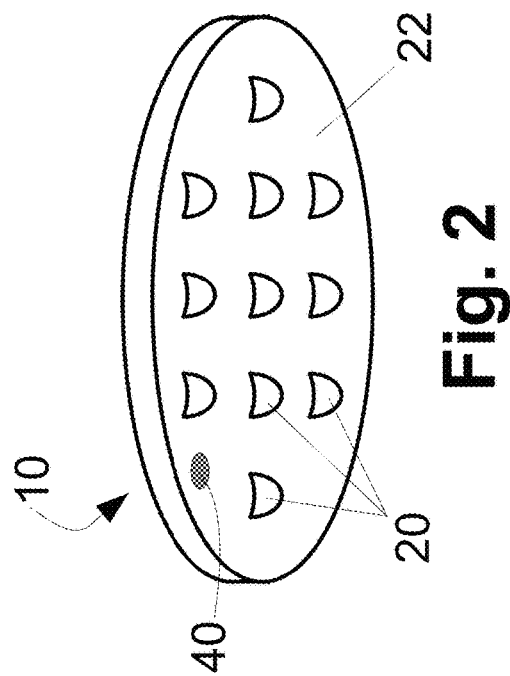

FIG. 2 diagrammatically illustrates an embodiment of a light source of the viral disinfection system of FIG. 1 which employs light emitting diodes (LEDs).

FIG. 3 diagrammatically illustrates an embodiment of a light source of the viral disinfection system of FIG. 1 which employs a mercury lamp.

FIG. 4 diagrammatically illustrates a viral disinfection method suitably performed using the viral disinfection system of FIG. 1.

FIGS. 5 and 6 illustrate two respective methods for controlling the light emitted by the light sources of the system of FIG. 1 based on occupancy as indicated by a motion sensor (FIG. 5) or microphone (FIG. 6).

FIG. 7 presents a plot of actinic hazard and germicidal efficiency functions versus wavelength.

FIG. 8 presents a plot of $\log_{10}$ actinic hazard versus wavelength.

FIGS. 9-14 present spatial distribution of irradiance for various configurations of light sources of the viral disinfection system of FIG. 1.

FIGS. 15-24 present various tables of data as described herein.

FIGS. 25-29 diagrammatically show various embodiments of multispectral light sources for disinfection as described herein.

FIG. 30 diagrammatically illustrates a multispectral light source for disinfection that is programmable to implement a spectrum tailored for disinfecting a specific target pathogen.

FIG. 31 presents a table summarizing D90 doses at 254 nm for various categories of pathogens in water, on surfaces, and in low and high relative humidity air.

FIG. 32 plots D90 and actinic limit doses for *E. coli* in air.

FIG. 33 presents a table comparing D90 doses for various bacteria inactivated in aqueous media at 365 nm, 302 nm, and 254 nm.

DETAILED DESCRIPTION

The present disclosure provides for a lighting system that includes a light source configured to generate light in an environment for human occupancy, the light including an inactivating portion having wavelengths in the UV-C range, e.g. UV-C in a range of 280 nm or lower, or more preferably UV-C in a range of 275 nm or lower, or even more preferably UV-C in a range of 270 nm or lower.

It is recognized herein that UV-C exposure is particularly efficacious for disinfecting virus pathogens, even when the UV-C is irradiated directly into an environment for human occupancy, even when occupied. For example, a single coronavirus particle is extremely small, having a size of about 0.1 micron in diameter. The particles of many other pathogenic viruses are comparably small, e.g. well under 1 micron in diameter in many cases. As a result, UV-C radiation can damage the nucleic acid contained in a coronavirus or other virus particle suspended in air very rapidly, e.g. in well under one second with a dose as low as ~10 J/m$^2$. By contrast, the short wavelength of UV-C light means that its penetration depth in human tissue is small, usually being absorbed in the outer layer of skin or eye tissue. Hence, UV-C radiation has less impact on human safety than, for example, UV-B radiation, and some regulatory schemes set the dose limit for actinic radiation exposure at 270 nm to 30 J/m$^2$ over an eight hour or 24 hour period (the time frame depending on the regulatory scheme), with higher doses allowed at both shorter and longer UV wavelengths. While this is a low dose, as discussed herein it provides a window for employing disinfection of occupied spaces by way of UV-C light, without posing a safety risk to occupants. In particular, some embodiments disclosed herein leverage the difference in the inactivation rate for virus particles irradiated with a given UV-C dose over a short period of time, versus the photobiological hazard-limited dose for human tissue, which is limited over a longer integration time of UV-C irradiation (that is, a dose, e.g. measured in units of J/m$^2$). Based on this recognition, more effective viral disinfection in an occupied space may be achieved by using pulsed or timed UV-C light, which can allow for a higher irradiance during pulse peaks, and a lower (or zero) irradiance between the pulses or on times. This provides for higher irradiance to inactivate virus particles while they are suspended in air, while keeping the time-integrated UV-C dose "Below the Exposure Limit" (BEL). This may be referred to as Direct Irradiation Below the Exposure Limit (DIBEL). Herein, direct irradiation refers to light that is irradiated directly into an environment for human occupancy, whether occupied or unoccupied during the irradiation; DIBEL refers to direct irradiation at a dose Below the Exposure Limit.

For coronavirus and many other viruses, a major transmission vector is by way of respiratory droplets produced when an infected person coughs, sneezes, sings, or talks. In one model of this transmission vector, the droplets evaporate quickly, leaving "bare" virus particles suspended in ambient air for many minutes (larger particles) or many hours (smaller particles) before settling onto surfaces. In the case of SARS-CoV-2, the virus is known to remain viable while suspended in air for many hours, with a half-life (time to 50% inactivation due to natural causes) of 1.1 hours. In a room, vehicle cabin, an aircraft cabin, train compartment, or other (at least mostly) enclosed environment for human occupancy, this means that airborne virus particles present a transmission threat for several hours or more after an infected person leaves the environment.

With reference now to FIG. 1, a viral disinfection system is configured to disinfect an environment 2 for human occupancy, such as the room 2 having a ceiling 4, floor 6, and walls 8 that is occupied by persons. More generally, the environment 2 for human occupancy can be a room (which could be a conference room, medical operating room, a hallway, office, classroom, bathroom, or so forth), or a vehicle cabin, an aircraft cabin, train compartment, or so forth, or even an outdoor environment (which could be a shopping cart corral or picnic venue, or so forth). In these various embodiments, the environment 2 for human occupancy has a floor 6, such as the illustrative floor 6 of the room, the floor of the vehicle or aircraft cabin, or the floor of the train compartment. In the case of an outdoor environment, the floor 6 is considered the ground of the outdoor environment. It will be appreciated that the portion of the environment 2 that is actually occupied by persons is typically the space that is approximately two meters or closer (e.g. 2.1 meters or closer in some embodiments) to the floor 6, which is the expected occupancy in a normal work environment. Hence, the disinfection system is typically designed to provide disinfection at a target plane, where the target plane is two meters or closer to the floor 6. The viral disinfection system includes at least one light source 10 configured to emit light into the environment 2 for human occupancy to inactivate one or more virus pathogens suspended in ambient air of the environment 2 or residing on surfaces 12 or materials, including human skin. The illustrative at least one light source 10 of FIG. 1 includes a plurality of ceiling-mounted light sources and a plurality of wall-mounted light sources. More generally, all the light sources could be only ceiling-mounted, or all the light sources could be only wall-mounted. More generally, the light sources are not required to be mounted, but may be supported in lamp holder fixtures, or resting on the floor or on furniture, in coves, suspended from supports, or so forth. The at least one light source 10 preferably includes a plurality of light sources distributed over wall(s) and/or the ceiling so as to apply the light to most or all of the ambient air in the environment 2. Complete coverage may not be necessary, however, if the ambient air in the environment 2 is circulating so that air in any "dead" areas that are not irradiated by the light will move by convection or other circulation into irradiated areas.

The light emitted by the at least one light source 10 includes an inactivating portion having peak wavelength in a range of 200 nanometers to 280 nanometers inclusive. More generally, the light emitted by the at least one light source 10 may be UV-C light (defined as the wavelength range 100 nanometers to 280 nanometers inclusive), or may be some range within the UV-C spectrum, such as 200-275 nanometers inclusive or 200-270 nanometers inclusive. Depending on the type of light source 10, the light may be narrow-band light, e.g. predominantly a single discrete emission line or a set of discrete emission lines, or may be broad-band light. Preferably the intensity of the light emitted by the at least one light source 10 is effective to achieve at least 90% inactivation of the virus pathogen in the ambient air within about two hours. On the other hand, the efficacy of UV-C light for inactivating virus pathogen on a surface is much lower (e.g., requiring about 10 times more UV-C light in some reports); hence, the irradiance at the one or more surfaces may in some embodiments be not effective to achieve at least 90% inactivation of the virus pathogen on the one or more surfaces within about two to four hours, but may be inactivated by the longer-term dose within 8 hours or over multiple 8-hour doses.

With reference to FIG. 2, in some embodiments each light source 10 comprises one or more light emitting diodes (LEDs) 20, for example disposed on a printed-circuit board or other substrate 22 and optionally mounted in a housing (not shown). The LEDs are UV-C LEDs that emit light in the UV-C range (100-280 nanometers inclusive) or some range within the UV-C range such as 200-280 nanometers, 200-275 nanometers, 200-270 nanometers, 230-280 nanometers, 240-280 nanometers, 240-275 nanometers, 240-270 nanometers, or so forth. As will be described in greater detail later herein, the LEDs 20 may be aluminum gallium nitride (AlGaN) LEDs, although other types of UV-C-emitting LEDs may be used as the LEDs 20. Laser diodes may also be used in place of some or all of the LEDs, laser diodes having advantages related to beam pattern and pulsing capabilities. In some embodiments, there may be as few as a single LED 20 disposed on the substrate 22. The substrate 22 may optionally be coated with a diffuse or specular UV-C-reflective layer such as an aluminum layer, a silver layer, a foam Teflon™ (e.g. expanded polytetrafluoroethylene, i.e. ePTFE, from W.L. Gore) layer, a thin-film optical coating, or so forth in order to increase the light emission efficiency.

Figure 3:
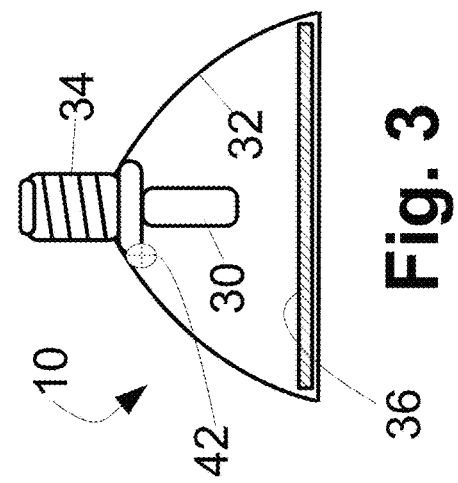

With reference to FIG. 3, in some embodiments each light source 10 comprises a mercury (Hg) lamp 30, optionally further including a collecting reflector 32 with a reflecting surface such as an aluminum surface, a silver surface, a foam Teflon Teflon™ (e.g. expanded polytetrafluoroethylene, i.e. ePTFE) surface, a thin-film optical coating, or so forth in order to increase the light emission efficiency. In general, the Hg lamp 30 may be a medium-pressure Hg lamp, or a low-pressure Hg lamp.

The light source 10 comprising one or more LEDs 20 (FIG. 2) outputs low intensity light, typically only ~1-100 mW of UV radiation, and consuming only about 0.1-10 W of electrical power. The mercury lamp 30 generally produces a much higher intensity ~1-100 W of UV radiation, but is not adversely affected by dissipation of self-heat. Accordingly, in some embodiments, the light source 10 does not include a heat sink. The light source 10 may optionally include additional features, such as a lightbulb base 34 for mechanically and electrically connecting the light source 30 to A.C. electrical light bulb base, or a spectral filter 36. If the intensity output by the mercury lamp 30 is too high to ensure safety of the occupants, the spectral filter 36 may additionally or alternatively integrate or be deployed in combination with a neutral density filter or baffles or collimators or the like to reduce the UV radiation intensity. While the illustrative lightbulb base 34 is an Edison screw lightbulb base 34, another type of lightbulb base may be used, such as a bayonet base, a bi-post lightbulb base, or a bi-pin lightbulb base. While the illustrative lightbulb base 34 is shown in conjunction with the mercury lamp 30 in FIG. 3, the LED-based light source of FIG. 2 may also optionally incorporate a lightbulb base for powering the LEDs 20. On the other hand, embodiments in which another type of electrical connection is employed are contemplated, e.g. the light source may include a pigtail that is wired to an electrical power source, or the light source may include an on-board battery, or so forth. It will be appreciated that the light source 10 may also include suitable electrical power conditioning circuitry, e.g. an electrical ballast circuit for driving the Hg lamp 30, or LED driver circuitry disposed on or embedded in the substrate 22 in the case of an LED-based light source such as that of FIG. 2. The illustrative spectral filter 36 employed with the Hg lamp 30 of FIG. 3 may, for example, filter out the mercury resonance line at 185 nanometers so that the output of the light source is more purely at the 254 nanometer mercury resonance line. Such filtering can, for example, reduce ozone generation. Similarly, a spectral filter may be employed with the LED(s) 20. By way of a more generalized example, the light source may include a spectral bandpass filter 36 having a passband in the wavelength range of 240 nanometers to 280 nanometers inclusive, for example. A filter may be especially beneficial in passing energy at the most efficacious wavelength, while blocking energy at less efficacious wavelengths that nonetheless accrue against the actinic EL (Exposure Limit) dose without maximal benefit to disinfection.

Figure 1:
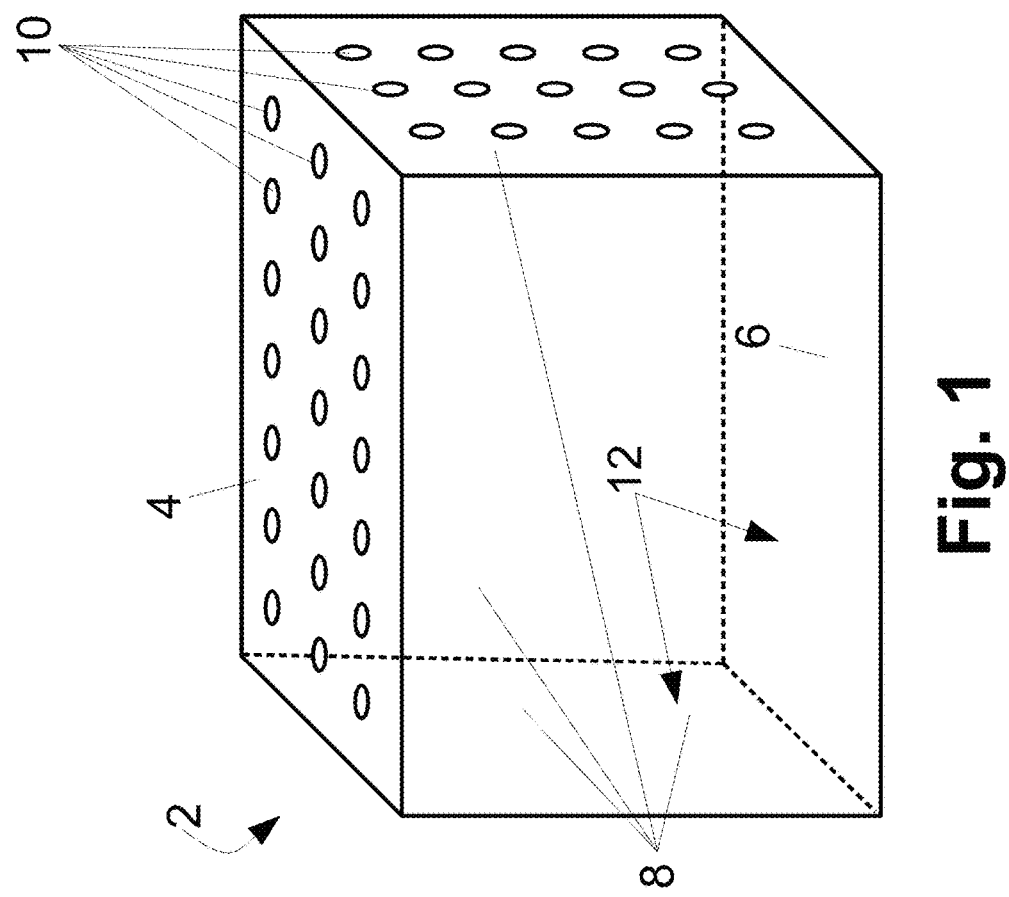
FIG. 1 diagrammatically illustrates a viral disinfection system is configured to disinfect an environment for human occupancy.

Because the UV-C light emitted by the light source 10 is low power and is intended to fill the interior space of the environment 2 (possibly using multiple light sources 10 as shown in FIG. 1), in some embodiments the light source 10 does not include any refractive or reflective optical components. Alternatively, if refractive or reflective optical components are included (not shown, e.g. incorporated into the fixture and/or into the LEDs, and/or optionally including spectral filters as previously discussed), they should be UV-C transmissive refractive or diffractive components or UV-C reflective components, or UV-C-tuned quantum-cavity components e.g. arranged to direct the light toward the one or more surfaces 12 or toward preferred target zones in the environment, e.g. where people are likely to congregate or to not congregate. It is also noted that in some embodiments, a combination of LED-based light sources 10 (e.g. as shown in FIG. 2) and mercury lamp light sources 10 (e.g. as shown in FIG. 3) or some other type of UV light source (e.g., excimer laser, laser diode, et cetera) may be employed together to disinfect the environment 2.

With continuing reference to FIGS. 2 and 3, in some embodiments a sensor 40, 42 is provided, which is configured to detect occupancy of the environment 2; and an electronic processor (not shown, e.g. a microprocessor or microcontroller and ancillary electronics such as a RAM, ROM, or other memory chip, discrete circuit elements, and/or so forth) is optionally provided that is configured (e.g. programmed by software or firmware stored in a ROM chip and executable by the microprocessor) to control the at least one light source 10 to generate the light toward one or more surfaces 12 or preferred target zones based on the occupancy of the environment 2 detected by the sensor 40, 42. By way of non-limiting illustration, the LED-based light source of FIG. 2 includes a motion sensor, thermopile, ultrasonic sensor, or other occupancy sensor(s) 40 for detecting occupancy of the environment 2 by detecting motion in the environment. The motion sensor 40 may comprise any suitable motion sensor, for example a passive infrared (PIR) motion sensor, a microwave motion sensor, an ultrasonic motion sensor, a camera-based motion sensor, and/or so forth. A camera-based, or imaging, sensor may determine the density or proximity of occupants and respond with higher or lower UV-C doses as appropriate. As a further non-limiting illustration, the sensor may comprise a microphone 42 as shown in FIG. 3, which detects occupancy based on detected vocalization.

The illustrative sensor 40, 42 is integrated into a light source 10; if the electronic processor is also integrated into the light source 10 then this can provide a single unitary device that both emits the UV-C light for disinfection and detects occupancy and controls that UV-C light based on the occupancy. In other embodiments (not shown), the sensor may be a separate component from the light source(s) 10, and the electronic processor may be integral with the light source(s) 10, or may be integral with the sensor component, or the electronic processor may be a third component separate from both the light source(s) and the sensor component. For example, the electronic processor may be implemented as a central control computer that controls power to a fleet of light sources 10 distributed throughout a room, floor, building, or other environment. In such cases, the individual light sources 10 may have no integral electronic processor (for example, the central control computer may deliver a controlled amount of power to the light sources 10 to directly control their light output intensities); or, in other embodiments, may have an integral electronic processor of low computational complexity that merely receives control signals from the central control computer and controls the light source 10 on the basis of (e.g., proportional to) that control signal. Such "distributed" implementations may advantageously allow the electronic processor to receive sensor signals from a number of sensors distributed in the environment 2 so as to more accurately assess occupancy of the environment 2. Moreover, some embodiments of the light source 10 may have no electronic processor and may not be controlled by any remote electronic processor. For example, the light source 10 may have an integral analog or digital clock that is set to operate the light source 10 during a set time interval (e.g. 9:00 am to 5:00 pm for an office that is staffed from 9 am to 5 pm; or 8:00 am to 8:00 pm for a retail store that is open from 8 am to 8 pm; or so forth).

With reference now to FIG. 4, a viral disinfection method suitably performed using the light source(s) 10 is described. In an operation 50, the light source(s) are installed in the environment 2 for human occupancy. This entails physically mounting the light sources, and electrically connecting the light sources to electrical power (e.g., connecting the lightbulb base 34 to a pre-existing lighting receptacle (e.g. lightbulb socket), installing a battery if the light source is battery powered, or wiring a pigtail to electrical power, or so forth). In the installation operation 50, care should be taken to provide sufficient coverage of the volume of ambient air in the environment 2, so that most or all of this volume is irradiated by the UV-C light emitted by the light source(s) 10. Additionally, care should be taken to ensure that persons in the environment 2 are not exposed to excessive UV-C light by being too close to the light source(s) 10. For example, the light source(s) 10 can be designed for ceiling mounting, and the light source(s) 10 can be designed so that when thusly spaced from the one or more surfaces 12 by (about) the ceiling height, this distance is large enough for the light to have irradiance at the one or more surfaces 12 below the exposure threshold (e.g., 30 J/m$^2$ or less of actinic-weighted irradiance, or 60 J/m$^2$ or less over an eight hour period in some embodiments, as further explained elsewhere herein).

With continuing reference to FIG. 4, in an operation 52 the ambient air, surfaces and materials of the environment 2 are disinfected by emitting UV-C light using the at least one UV-C light source 10. As will be described in greater detail elsewhere herein, the light source(s) 10 are designed to provide sufficient irradiance to provide effective viral disinfection while ensuring the UV-C light exposure remains below the Exposure Limit (EL) for a typical 8 hour workday. As further indicated in FIG. 4, in some embodiments this balancing of viral disinfection efficacy versus providing occupant safety is achieved in part by pulsing or timing the UV-C light to provide higher peak intensity for more efficient virus disinfection while keeping the time-integrated dose below the EL. Such pulsing or timing can be performed by the electronic controller, or can be implemented by an analog circuit that applies electrical pulses to the LEDs 20 or Hg lamp 30. In some non-limiting illustrative embodiments, the light source(s) 10 are configured to generate the light as pulses having pulse width of 1 second or less and pulse spacing of at least 10 seconds. This reflects the fact that the inactivation of many pathogens is not reciprocal, i.e., a measured dose [J/m$^2$] delivered in a short time may be more effective than the same dose delivered over a longer time; whereas, the safety hazard is a function of the time-integrated exposure dose. For (as just one example) 1 second pulses spaced apart by 10 seconds, the duty cycle is only 10% leading to an order-of-magnitude reduced time-integrated dose. Alternatively (as just one example), 1 second pulses can be made at 10 times higher irradiance to achieve better viral disinfection while maintaining the same time-integrated dose as a continuous irradiance at the time-averaged level.

With continuing reference to FIG. 4, optionally the sensor 40, 42 is used to turn the UV-C light on or off based on the occupancy of the environment 2. If the dominant viral transmission vector is by way of respiratory droplets, and the bare virus particles after droplet evaporation stay suspended for several hours on average, then the occupancy-based control may be designed to turn the UV-C light on, or increase the intensity of the UV-C light, in response to detected occupancy, and then turn it off (or reduce the intensity) a number of hours after the detection of a cessation of occupancy. This can reduce energy consumption—however, energy consumption may be negligible due to the low intensity of the UV-C light emitted by the light source(s) 10. A more significant advantage of this occupancy-based control is to reduce the UV-C dose to surfaces inside the environment 2. For example, some fabrics, furniture covers, plastics, and the like can become discolored over time due to UV-C exposure. In the case of a space that is only occupied during an 8-hour work day, and possibly only for some small portion(s) of that work day (for example, a conference room that is only used for a couple hours during the work day), this approach of occupancy-based control can greatly reduce the UV-C exposure of surfaces, thereby reducing UV-C-induced surface discoloration.

With reference to FIG. 5, two illustrative examples of occupancy-based control using the motion sensor 40 of FIG. 2 are described. With reference first to the left-hand flowchart, at a state 60, the light source(s) 10 are assumed to be off or operating at low intensity. At a decision 62, the motion sensor 40 is monitored, and as long as motion is not detected the light source(s) 10 are kept in the state 60. When at the decision 62 motion is detected, then the light source(s) 10 are switched to a state 64 in which the light source(s) 10 are on or brought up to emit the UV-C light at a higher intensity. Thereafter, at a decision 66, the motion sensor 40 is again monitored to detect when motion ceases for a time interval T. As long as this condition is not met, the light source(s) 10 are kept in the state 64 to provide viral disinfection (or increased viral disinfection). When at the decision 66 it is determined that motion has ceased for the time interval T, then the light source(s) 10 are switched back to the state 60 in which the light source(s) 10 are off or reduced to the low intensity. The time interval T is suitably chosen based on (statistical) residency of virus particles in the ambient air. For coronavirus particles, this residency has been estimated to be about 2 hours; hence, the predetermined time T may suitably be between one and three hours inclusive in some embodiments. The time interval may be chosen for a specific implementation based on the statistical residency of the virus particles to be disinfected balanced by factors such as the desire to reduce UV-C damage to surfaces in the environment 2. In some embodiments, it is contemplated for the time interval T to be set to zero, in which case the light source(s) 10 are switched back to the state 60 in which the light source(s) 10 are off or reduced to the low intensity immediately upon detection of the cessation of motion at the operation 66.

With continuing reference to FIG. 5 but now referencing the right-hand flowchart, the control may also reduce or turn off the UV-C intensity in response to detected motion. By this alternative approach, the disinfection system may apply UV-C at an intensity such that the light emitted by the light source(s) 10 is effective to produce an actinic dose at a target plane in the environment above the 30 $J/m^2$ threshold over an eight hour period, but to do so only when the environment 2 is unoccupied. To this end, at a state 60', the light source(s) 10 are assumed to be on and operating at high intensity (again, optionally at an intensity such that the light emitted by the light source(s) 10 is effective to produce an actinic dose at a target plane in the environment above the 30 $J/m^2$ threshold over an eight hour period). At a decision 62', the motion sensor 40 is monitored, and as long as motion is not detected the light source(s) 10 are kept in the state 60'. When at the decision 62' motion is detected, then the light source(s) 10 are switched to a state 64' in which the light source(s) 10 are turned off or reduced to a lower intensity, e.g. to an intensity such that the light emitted by the light source(s) 10 is effective to produce an actinic dose at a target plane in the environment that is below the 30 $J/m^2$ threshold over an eight hour period. Thereafter, at a decision 66', the motion sensor 40 is again monitored to detect when motion ceases for a time interval T. As long as this condition is not met, the light source(s) 10 are kept in the state 64' to provide safety for the persons occupying the environment 2. When at the decision 66' it is determined that motion has ceased for the time interval T, then the light source(s) 10 are switched back to the state 60' in which the light source(s) 10 are on and emitting at the high intensity. Here, the time interval T may be set to zero, or may be set to a value chosen to allow for some error in the occupancy sensing operation 66'. For example, a time interval T of two minutes may be chosen to ensure that the light source(s) 10 are not switched to the state 60' due to a period of inactivity by the occupants.

Figure 6:
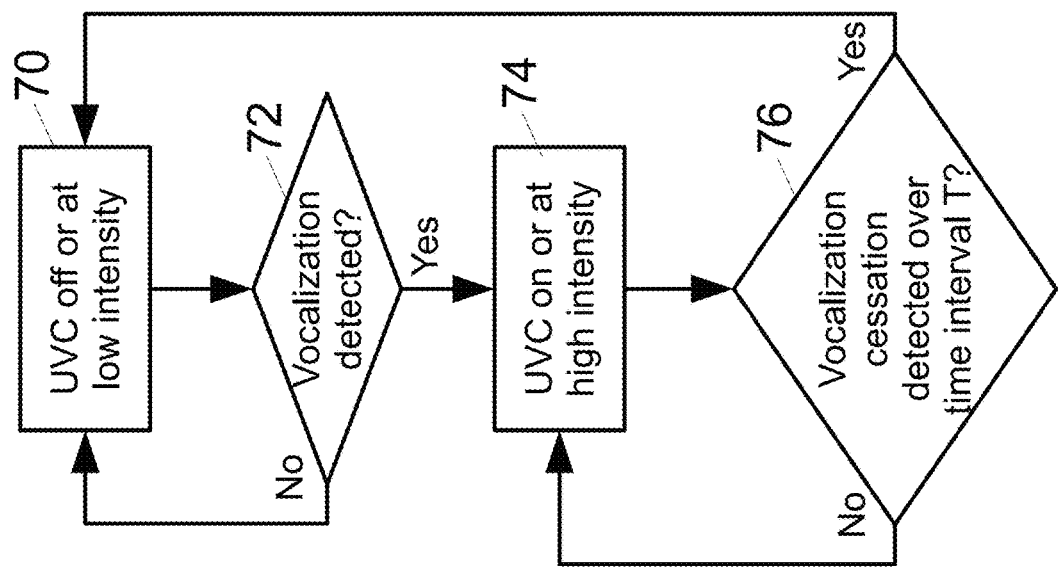

With reference to FIG. 6, an illustrative example of occupancy-based control using the microphone 42 of FIG. 3 is described. At a state 70, the light source(s) 10 are assumed to be off or operating at low intensity. At a decision 72, the microphone 42 is monitored, and as long as vocalization is not detected the light source(s) 10 are kept in the state 70. In a simple embodiment, any detected sound whose amplitude is above some minimum threshold is taken to be a detection of vocalization. In a more complex embodiment, spectral filtering, sound duration, or other automated analysis of the detected sound may also be applied so as to reduce likelihood that spurious noise caused by the HVAC system or other noise sources is misinterpreted as vocalization. When at the decision 72 vocalization is detected, then the light source(s) 10 are switched to a state 74 in which the light source(s) 10 are on or brought up to emit the UV-C light at a higher intensity. Thereafter, at a decision 76, the microphone 42 is again monitored to detect when vocalization ceases for a time interval T. As long as this condition is not met, the light source(s) 10 are kept in the state 74 to provide viral disinfection (or increased viral disinfection). When at the decision 76 it is determined that motion has ceased for the time interval T, then the light source(s) 10 are switched back to the state 70 in which the light source(s) 10 are off or reduced to the low intensity. The time interval T is suitably chosen as described for the motion sensor-based control of FIG. 5. An advantage of using vocalization detection for the control is that respiratory droplet mediated transmission is most likely in response to an infected person talking, singing, coughing, sneezing, or engaging in some other vocalization. On the other hand, if an infected person merely passes through the environment 2 without vocalizing, the likelihood of transmission is much lower compared with the case of vocalization. Hence, the vocalization-based control may provide more well-tailored application of the UV-C disinfection for these viruses. In some variant embodiments (not shown), the control approach of FIG. 6 may be adjusted to, for example, deliver a short period (e.g. 5-20 minutes in some embodiments) of higher intensity UV-C light in response to a detected loud vocalization such as a cough, singing, shouting, or multiple persons speaking or the like which (if done by a virus-infected person) is likely to expel a higher concentration of virus particles into the ambient air as compared with soft speaking. In another embodiment, the motion, occupancy, or microphone sensors may be spatially resolved thereby directing only those UV-C light sources that are most directly irradiating the source of the motion, occupancy or sound to be irradiated, or to receive enhanced irradiation.

It will be appreciated that a variant of the embodiment of FIG. 6 analogous to that of the right-hand flowchart of FIG. 5 may be employed, in which the UV-C is on at high intensity and is turned off or to lower intensity in response to detection of occupancy of the environment 2.

The disinfection system is sometimes referred to herein as a viral disinfection system, reflecting that the UV-C light is particularly effective for inactivating virus particles. However, it will be appreciated that the disinfection system is also expected to be effective for inactivating other pathogens such as planktonic or sessile bacteria, or fungi. Moreover, in some embodiments described herein, additional longer wavelength light sources may be provided along with the light sources 10 that output in the UV-C, in order to enhance the disinfecting efficacy, such as for certain bacteria for which UV-C may be less effective.

Having provided an overview of some disclosed viral disinfection systems and methods with reference to FIGS. 1-6, in the following some further aspects and more detailed embodiments are described.

The following terms are used herein.

Figure 7:
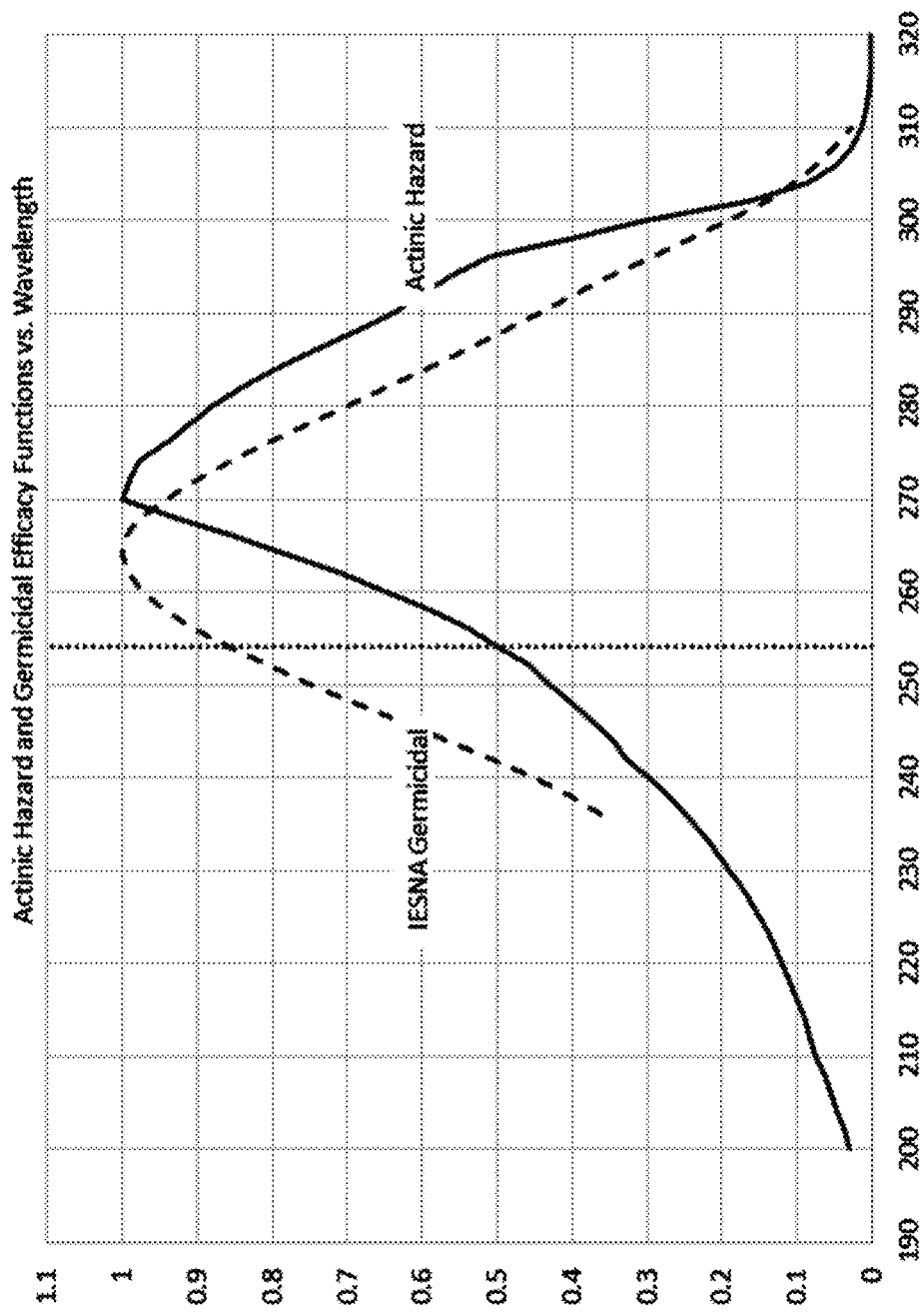
Figure 8:
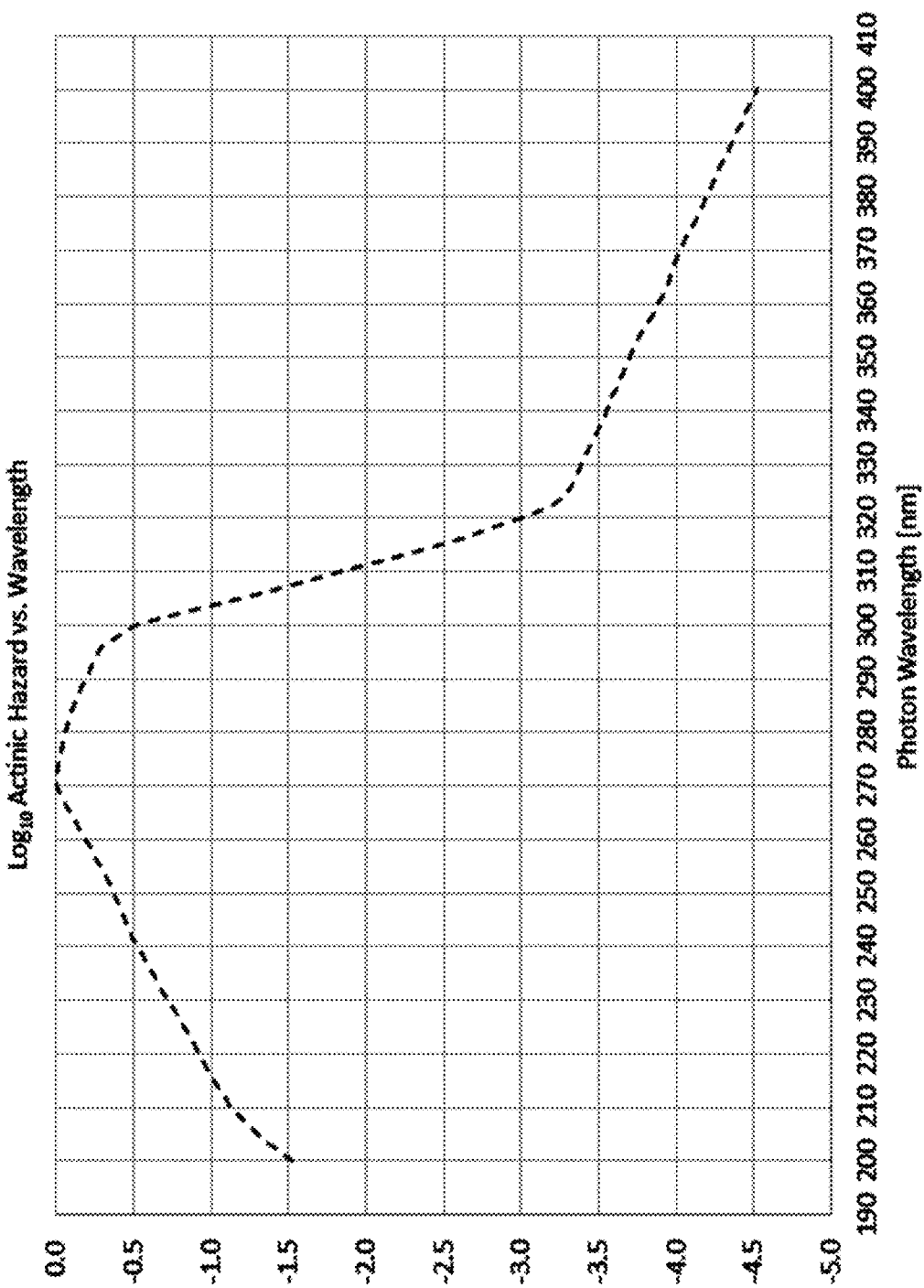

"Actinic dose" [$J/m^2$] is the quantity obtained by weighting spectrally the dose according to the actinic action spectrum value (see FIGS. 7 and 8) at the corresponding wavelength.

"Exposure limit" (EL) [$J/m^2$] is the level of exposure to the eye or skin that is not expected to result in adverse biological effects. Individuals in the vicinity of lamps and lamp systems shall not be exposed to levels exceeding the exposure limits. A dose Below the EL will be referred to as "BEL". EL may also be referred to as the Threshold Limit Value (TLV).

"Irradiance", E [$W/m^2$], at a point of a surface is the quotient of the radiant power incident on an element of a surface containing the point, by the area dA of that element.

"Luminaire" is restricted to apparatus used for distributing light in general lighting.

"Lamp system" or "lighting system" implies use of lamps in other than general lighting applications.

"Radiant energy" [J] is the time integral of the radiant power over a given duration.

"Radiant exposure" or "dose", H [$J/m^2$], the integral of the irradiance, E, at a given point over a given duration, $\Delta t$. May also be expressed in $mJ/cm^2$ or other units.

"Radiant power" [W] is power emitted, transmitted or received in the form of radiation, often called radiant flux.

"Spectral irradiance" [$W/m^2$-nm] is the quotient of the radiant power in a wavelength interval $d\lambda$, incident on an element of a surface, by the area dA of that element and by the wavelength interval $d\lambda$.

"Ultraviolet (UV) radiation" pertains to the range between 100 nm and 400 nm, commonly subdivided into UV-A, from 320 nm to 400 nm; UV-B, from 280 nm to 320 nm; and UV-C, from 100 nm to 280 nm.

The "wavelength" of a narrow-band light source, such as an LED or laser diode is understood to mean the peak wavelength, even though light is emitted from a narrow band of wavelengths shorter and longer than the peak wavelength, e.g. the full-width at half-maximum of an LED may be about 10 nm, or about +/−5 nm around the peak wavelength, with some emission even outside of the +/−5 nm range.

The "peak wavelength" of a narrow-band light source is understood to mean the wavelength having the highest spectral power [W/nm] of any wavelength in the emission spectrum of the light source.

The "peak wavelength" of a broad-band light source, or a light source having more than one emission line or band, such as a discharge lamp or excimer lamp is also understood to mean the wavelength having the highest spectral power [W/nm] of any wavelength in the emission spectrum of the light source.

"Multispectral" refers to light having more than one peak wavelength. An equivalent term in common use is polychromatic. Multispectral light is in contrast to monochromatic light which has only one peak wavelength, such as a light emitting diode or laser diode that emits a peak wavelength at the approximate center of a relatively narrow band of wavelengths, typically having a full-width at half-maximum (FWHM) of about 10 nm. The multiple emission peaks in a multispectral light source will typically be separated by relative minima between the peaks.

The Actinic UV hazard exposure limit for exposure to ultraviolet radiation incident upon the unprotected skin or eye apply to exposure within any 24-hour period.

To protect against injury of the eye or skin from ultraviolet radiation exposure produced by a broadband source, the effective integrated spectral irradiance (effective radiant exposure, or effective dose), $E_s$, of the light source shall not exceed 30 $J/m^2$.

In this disclosure, for the sake of simplicity with sufficient precision, we will assume that a nearly monochromatic light source such as an LED, or a low-pressure (LP) mercury (Hg) lamp having dominant radiation in the UV at 254 nm emits only at its peak wavelength, e.g. 254 nm for a low pressure Hg lamp or 270 nm or 365 nm for an LED lamp, et cetera. It can be shown, for precision, that the actual integral of the narrow band of emission from an LED, weighted by the actinic hazard function, may differ from the simplified assumption of a monochromatic emitter by as much as about 10%, that level of precision not being required for the purpose of this disclosure.

The effective integrated spectral irradiance, $E_s$, is then defined as the quantity obtained by weighting spectrally the dose (radiant exposure) according to the actinic action spectrum value at the corresponding wavelength. For example, given the actinic action spectrum value at 254 nm of 0.5, the effective dose, $E_s$, at 254 nm is 0.5×actual dose (or radiant exposure), so that the Exposure Limit for 254 nm radiation=30 $J/m^2$÷0.5=60 $J/m^2$.

In this disclosure, the term "light source" implies any source of visible or non-visible radiation (photons), including UV radiation. It may refer to an LED or an LED luminaire or a discharge lamp or a discharge lamp luminaire, or the p-n junction of an LED or the filament of an incandescent lamp, or a laser diode or a plurality of such sources, for example.

The term "low-pressure (LP)" in reference to mercury discharge lamps is used herein as defined by IESNA 1984 IES Lighting Handbook as having mercury vapor pressure ~0.01-10 torr, operating at envelope temperatures in the range about 10-100° C. with radiation dominated by the two mercury resonance lines at 185 and 254 nm, with about 90% of the energy radiated at 254 nm. A small percentage of energy is emitted at longer UV and visible wavelengths. The choice of glass envelope of the lamp may further reduce the amount of 185 nm emission to avoid creation of ozone in the air. (This is another example of the spectral filter 36 diagrammatically indicated in FIG. 3). The emission is generally referred to as UV-C.

The term "medium-pressure (MP)" in reference to mercury discharge lamps is used herein as defined by Helios Quartz UV Lamp brochure as having mercury vapor pressure ~10-100 atmospheres, operating at envelope temperatures in the range about 600-900° C. with radiation peaks extending throughout the UV and Visible ranges. The emission is generally referred to as UV-B/UV-C. Again, the spectral filter 36 may optionally be provided to block the UV-B component, unwanted UV-C component(s) (e.g. at wavelengths below about 200 nm as this radiation can produce ozone which may be considered undesirable), or other unwanted emission wavelengths.

The illustrative light source 10 having an inactivating portion of radiation in the Ultraviolet-C (UV-C) range may be a separate light source from a visible light source or may be included as part of a visible light source. The inactivating UV-C light source 10 may also be combined with a light source having an inactivating portion having wavelengths in the UV-A or other longer wavelength ultraviolet range, that is, longer than the UV-C range, e.g. of 280 to 380 nanometers, or with a light source having an inactivating portion in any other wavelength range from about 200 nm to about 3000 nm. For example, it is contemplated to combine UV-C light source(s) 10 as disclosed herein with light sources emitting in the UV-A or other longer wavelength ultraviolet range (e.g. 280-400 nm, or 280-380 nm, or in other embodiments 300-380 nm) as disclosed in U.S. Pub. No. 2016/0271281 A1 which is incorporated herein by reference in its entirety to provide more efficacious disinfection of a broader range of pathogens. This approach leverages the differences in inactivation effectiveness of longer wavelength ultraviolet versus UV-C for various pathogens. As an example, in general, it is typical (though not universal) that bacteria are more effectively inactivated by BEL doses of UV-A or other longer wavelength ultraviolet radiation compared with BEL doses of UV-C radiation; whereas, it is typical (though again not universal) that virus particles are more effectively inactivated by UV-C radiation compared with UV-A or other longer wavelength ultraviolet radiation. Hence, a disinfection system that includes both UV-A or other longer wavelength ultraviolet light sources and UV-C light sources can provide effective disinfection of both bacteria and viruses. In some such embodiments, the UV-A and UV-C light sources are chosen, and/or filters such as illustrative spectral filter 36 (see FIG. 3) are provided to ensure that the UV-A and UV-C light sources output little or no radiation in the UV-B range, as this range can be more detrimental to occupants of the environment 2 while contributing relatively less to the pathogen disinfection efficacy. Additionally or alternatively, the UV-A and UV-C light sources are chosen, and/or filters such as illustrative spectral filter 36 (see FIG. 3) are provided to ensure that the UV-A and UV-C light sources output little or no radiation below (about) 200 nanometers as these shorter wavelength UV-C emissions can interact with ambient air to produce ozone, which may be undesirable. In some embodiments, the UV-C light sources and the longer wavelength ultraviolet light sources may be integrated as a single unitary luminaire or lamp, e.g. such as the LED-based light source of FIG. 2 in which the LEDs disposed on the substrate 22 include both UV-C LEDs as disclosed herein and UV-A LEDs as disclosed in U.S. Pub. No. 2016/0271281 A1. In another contemplated embodiment, a unitary luminaire or lamp outputting in both the UV-C and longer wavelength (e.g. UV-A) range comprises a medium pressure (MP) mercury lamp or Xenon lamp, as these lamps output emission lines in both the UV-C and UV-A range. Optionally, a spectral filter and/or neutral density filter is added to tailor the output of the MP mercury or Xenon or excimer lamp to the desired spectrum.

Most viruses, and many other pathogens are inactivated with a log-linear response for inactivation levels below about 99%. That means that the logarithm of the inactivation level is linearly proportional to the accumulated dose [J/m$^2$], such that if the D90 (1-log$_{10}$) dose is doubled, then typically 99% (2-log$_{10}$) of the virus particles will be inactivated. This log-linear relationship is referred to as the single-stage regime of inactivation. Single stage inactivation is typical for viruses and some other pathogens, including the SARS-CoV-2 virus (a type of coronavirus), typically up to at least 99% (2-log) inactivation, but typically not beyond 3-log inactivation. It is disclosed herein that the maximum allowed dose (60 J/m$^2$) in a 24-hour period of UV-C having a peak wavelength of 254 nm is at least two times greater than the dose required to inactivate 90% of the population ("D90" dose) of a wide range pathogens in air, including viruses and bacteria, therefore in the log-linear regime applying to most viruses, and in particular coronaviruses, it may be expected that at least 99% (2-log) will be achieved at the exposure limit of 60 J/m$^2$ at 254 nm.

In general it should be noted that most UV-C germicidal studies have been conducted at the 254 nm resonance line of the Hg discharge lamp. Relatively little data has been reported at other UV-C wavelengths, especially at the wavelengths that are recently made accessible by UV-C LEDs, e.g. at about 260 to 280 nm. To infer the D90 dose (or rate constant) at these characteristic UV-C LED wavelengths, the IESNA Germicidal action spectrum of FIG. 7 may be consulted since that curve represents the probability of a photon inactivating a pathogen via breaks in DNA and RNA strands which is the primary lethality mode for UV-C in virus. The IESNA germicidal curve in FIG. 7 indicates 83% relative efficacy at 254 nm, 100% at about 265 nm, 82% at 275, and 70% at 280 nm. Therefore, it may be expected that the D90 dose for a given virus at 275 nm is comparable to the D90 dose at 254 nm, and further that irradiation in the entire range of about 260-280 nm may be about as effective as that at 254 nm, such that the D90 doses quoted in literature may be anticipated to fairly well represent the expected doses using UV-C LEDs in the range 260-280 nm.

In some illustrative embodiments, the light source 10 comprises one or more light emitting diodes (LEDs) 20 (e.g. FIG. 2) having peak wavelength in the UV-C, preferably in the range 200-300 nm, more preferably about 250-280 nm, most preferably about 255-275 nm, providing an (effective, e.g. wavelength corrected) actinic dose of not more than 30 J/m$^2$ at the floor of the space (assuming ceiling mounting of the light sources 10). More generally, the light emitted by the light source 10 should be effective to produce an actinic dose at a target plane in the environment 2 of 30 J/m$^2$ or less over an eight-hour period. The target plane in the environment 2 may be an actual surface, such as the surfaces 12, or may be a virtual surface such as (by way of non-limiting illustrative example) a plane at a specified height, e.g. 4 feet, above the floor 6 that represents a typical midpoint of the upper portion of a person occupying the environment 2. In general, the target plane is at head height or lower of persons occupying the environment 2. In some embodiments, the target plane is two meters or closer to the floor 6, which is the expected occupancy in a normal work environment. In some embodiments, the target plane is 2.1 meters above the floor 6, as specified in some regulations. Whereas the actinic dose should not exceed 30 J/m² at a location in the space defined by regulations, it should preferentially exceed the D90 dose of the target pathogen, more preferably exceed the D99 dose, over a significant fraction of the occupied volume of the space.

In one embodiment targeting the SARS-CoV-2 virus, having an estimated D90 in air at 254 nm of about 3 J/m², the 8-hour dose throughout a significant fraction of the occupied volume of the space should preferably exceed about 3 J/m², more preferably exceed about 6 J/m², and should not exceed 60 J/m², at any location below 2.1 m above the floor within the occupied space.

In some illustrative embodiments, the light source 10 comprises one or more low-pressure mercury lamps 30 (e.g. FIG. 3) having peak wavelength at about 254 nm providing an effective actinic dose of not more than 30 J/m² at the floor of the space (assuming ceiling mounting of the light sources 10).

In some illustrative embodiments, the light source 10 comprises one or more medium-pressure mercury lamps having significant emission throughout the UV-C, UV-B, UV-A, and short-wave visible ranges. The spectral filter 36 (see FIG. 3) may be provided to ensure the desired UV-C emission (e.g., at 254 nm) and optionally also longer wavelength, e.g. UV-A, emission, is selected for irradiating the environment 2.

While the illustrative embodiments of the light source(s) 10 is LED-based (FIG. 2) or Hg lamp-based (FIG. 3), other types of light sources emitting in the UV-C may be used as the light source(s) 10. As some further examples (not shown), the light source 10 may comprise: one or more Xenon lamps having substantial emission in the UV-C range; and/or one or more excimer lamps having substantial emission in the UV-C range. It may also be anticipated that UV laser diodes, when they become commercially viable, will provide efficacious inactivation similar to that of UV LEDs at the same wavelengths. The narrower bandwidth of a laser diode (about 1-5 nm) relative to an LED (about 10 nm) and the narrower beam distribution may provide advantages as discussed in sections above, including targeting of precise spatial locations in the environment 2 or scanning (rastering) the beam through a prescribed pattern in the space, or in response to sensors in the space.

In some illustrative embodiments, the light source 10 comprises one or more lamps having substantial emission in the UV-C range, with wavelengths outside the range of about 240-280 nm filtered out of the spectrum, e.g. by spectral filter 36.

In some illustrative embodiments, the light source 10 is controlled to limit the dose of the inactivating portion of light not to exceed the allowable maximum dose in an 8-hour period.

In some illustrative embodiments, the light source 10 is controlled to emit the inactivating portion of light only when the space is unoccupied, for example as described with reference to block 56 of FIG. 4 and with specific examples given in FIGS. 5 and 6.

In some illustrative embodiments, the light source 10 is controlled to emit the inactivating portion of light only when the space is occupied (e.g., FIGS. 5 and 6).

In some illustrative embodiments, the light source 10 is controlled to emit the inactivating portion of light when the space is occupied and unoccupied, determined by the history of occupancy.

In some illustrative embodiments, the light source 10 is controlled to emit the inactivating portion of light on a pre-programmed schedule of on and off periods of time. For example, if there is a time interval in which it is known that the environment 2 will not be occupied, it is contemplated to apply higher intensity UV-C light to provide further enhanced disinfection. As a specific example, if the environment is the interior of a taxicab, then if it is known the taxicab will be in the garage (and hence unoccupied) for a certain time interval then a higher intensity UV-C light can be applied. In other embodiments, a different wavelength of UV-C light (and/or longer wavelength ultraviolet light) may be applied to enhance the disinfection, albeit with higher actinic irradiance.

In some illustrative embodiments, the light source 10 is controlled to emit the inactivating portion of light in pulses (≤1 sec) or prolonged surges (>1 sec) having peak intensity greater than 50% of the time-averaged intensity, e.g. as described with reference to block 54 of FIG. 4.

In some illustrative embodiments, the light source 10 is directed by optical elements to provide a substantially more uniform spatial distribution than the inherent Lambertian distribution on a horizontal plane.

In some illustrative embodiments, the light source 10 is directed by optical elements to provide a substantially more uniform spatial distribution than the inherent Lambertian distribution on a vertical plane or other non-horizontal plane or surface, whether real or virtual.

In some illustrative embodiments, the light source 10 is directed by optical elements to provide a substantially more focused spatial distribution than the inherent Lambertian distribution on a horizontal plane.

In some illustrative embodiments, the light source 10 is directed by optical elements to provide a substantially more focused spatial distribution than the inherent Lambertian distribution on a vertical plane or other non-horizontal plane or surface, whether real or virtual.

In some illustrative embodiments, the light source 10 is directed by optical elements to provide a substantially more uniform spatial distribution than the inherent Lambertian distribution throughout the volume of the irradiated space.

In the following, some non-limiting more specific embodiments are described.

Optical elements for shaping the light emitted by the LEDs 20 or Hg lamp 30 or other UV-C emitter may comprise refractive or diffractive elements having high transmittance (e.g. >20%, 50%, 80%, 90%) in the UV-C range, or may comprise reflective elements having high reflectance (e.g. >20%, 50%, 80%, 90%) in the UV-C range.

The Exposure Limit per IEC 62471, in a space occupied by humans is 30 J/m² of actinic light per day. The maximum allowed UV-C emission from a light source is determined by dividing the Exposure Limit of actinic light by the actinic Hazard Function of FIGS. 7 and 8, which equals 0.50 at 254 nm and 1.00 at 270 nm. Therefore, the Exposure Limit of 254 nm radiation, in a space occupied by humans is 60 J/m² per day. The limit is defined as a dose (energy per unit area) and is therefore the product of irradiance (power per unit area) and duration (time). The dose can thus be reached by any number of combinations of irradiance and duration, such as, but not limited to: constant irradiation for 24 hours; constant irradiation for a shorter period such as 8 hours followed by 16 hours or no irradiation; variable irradiation such that the total energy per unit area integrated over the 24 hour period is at or below the limit; one or more short-duration pulses delivered in the 24 hour period. The space occupied by humans may be an indoor or an outdoor space.

The Exposure Limit of $E_s$=30 J/m² of actinic radiation may be exceeded in a space when not occupied by humans.

Any pathogen that is inactivated at an effective dose, $E_s$<30 J/m² (e.g. actual dose, H<30 J/m² at 270 nm or H<60 J/m² at 254 nm) on a surface, or in the air, may be inactivated while the space is occupied by humans for the time duration of the exposure of the actinic light.

The dose of light required to inactivate 90% (99%) of a population of pathogens is referred to as the D90 (D99) dose, typically expressed in J/m². The most common wavelength at which D90 and D99 values are reported in the literature is 254 nm, corresponding to the dominant emission wavelength of low-pressure (LP) mercury (Hg) lamps.

Any pathogen for which D90 (D99)<60 J/m² at 254 nm will be inactivated by at least 90% (99%) upon application of the 60 J/m² dose while the space is occupied by humans while satisfying the actinic hazard limit.

UV LEDs are generally available in the range of about 240 nm or higher, up to 400 nm, typically in 5 nm increments of peak wavelength, and having a full-width at half-maximum bandwidth (FWHM) of about 10 nm. A UV LED may be chosen with peak wavelength about 255 nm in order to provide comparable inactivation of pathogens as a LP Hg lamp having the same radiant power as the 255 nm LED lamp, or may be chosen with peak wavelength anywhere between about 240 to 280 nm in order to provide sufficient inactivation relative to that provided at 254 nm. Employing a lower end of 240 nm (as opposed to a lower end that is, e.g. 230 nm) has certain advantages, such as current LED costs being lower for LEDs with peak wavelength of 240 nm or higher compared with LEDs with a lower peak wavelength of, e.g., 230 nm. As the UV-C emission is decreased in wavelength below 240 nm the UV-C emission also tends to produce ozone, which can be detrimental from a health standpoint and the ozone may have a detectable odor for some individuals. However, it is contemplated to employ UV-C LEDs emitting in a wavelength range that is lower than 240 nm, e.g. at 230 nm. A lower wavelength such as 230 nm may be useful, for example, when targeting the inactivation of viral pathogens with very small diameter or length, as the shorter wavelength (e.g. 230 nm) may be more easily absorbed by these smaller viruses.

Alternatively, a UV LED may be chosen with peak wavelength about 265 nm to coincide with the peak of the IESNA Germicidal action spectrum which may provide more efficacious inactivation of certain pathogens than 254 nm radiation.

Alternatively, a UV LED may be chosen with peak wavelength about 270-280 nm, or even 280-300 nm, to take advantage of the generally higher efficiency, longer operating life and lower cost of UV LEDs at longer wavelengths yet retaining the relatively high germicidal efficacy in those wavelength ranges.

Although the germicidal efficacy of the radiation may generally decline for wavelengths longer than about 270 nm, the actinic hazard function (see FIG. 2) also declines somewhat in step with the germicidal efficacy function, so that Exposure Limit at longer wavelengths is higher, potentially enabling comparable inactivation of pathogens at wavelengths longer than 254 nm for doses at the Exposure Limit. An advantage of the longer wavelength LED, with comparable germicidal efficacy to 254 nm radiation, is the relative cost, greater availability and electrical efficiency of the longer wavelength LEDs.

Spatial uniformity at the target plane is next considered.

From the Reference Moreno, "Effects on illumination uniformity due to dilution on arrays of LEDs", 2004 Proceedings of SPIE, the spatial distribution of irradiance on a plane illuminated by the LED is calculated as follows. Because the emitting region of LEDs is typically less than 1 mm on a side, its irradiance variation with distance can be approximated with the inverse square law for a point source. An LED source is a Lambertian emitter which means the irradiance distribution is also a cosine function of viewing angle. In practice, this dependence turns out to be a power law that mostly depends on the encapsulant and semiconductor region shapes. The irradiance distribution [W/m²], assuming a perfect Lambertian emission from the LED is given by:

$$E(r,\theta) = E_0(r)\cos\theta \quad (1)$$

Where $\theta$ is the viewing angle; $E_0(r)$ is the irradiance on axis at distance r from the LED. The Lambertian assumption is generally good for LEDs having no optics, neither integrated with the LED (primary optic) nor external to the LED (secondary optic). The LED light source may comprise a single LED emitter (p-n junction), or a plurality of LED emitters comprising a luminaire. If the plurality of LEDs comprising the luminaire are distributed over some lateral extent, d, and if d<<Z, the distance from the LEDs to the target plane (e.g., the floor or the horizontal plane of a person's head), then the luminaire may be approximated as a point source for estimating the distribution of irradiance at the target plane.

The irradiance on a target plane from a plurality of LEDs is given by a summation of the irradiances from all of the LEDs. The irradiance on the target plane from either a single LED or a luminaire having lateral extent d<<Z is given by Equation (1) above for $E(r,\theta)$.

Since a typical viral disinfectant system such as that of FIG. 1 may have light sources mounted at or near the ceiling 4 in a regular, rectilinear array of LEDs or luminaires, it is convenient to the transform the equation for E from cylindrical (r,θ,z) coordinates in Equation (1) to cartesian (x,y,z) coordinates, as set forth below:

$$E_{LED}(x,y,z) = \frac{ZI_{LED}}{[(x-X)^2 + (y-Y)^2 + Z^2]^{1.5}} \quad (2)$$

For a single LED or luminaire located at position x'=X, y'=Y, z'=Z relative to a target point (x=y=z=0) that is located on a target plane defined by z=0, the irradiance at point x, y in the target plane is given by Equation (2) above, where $I_{LED}$ is the LED (or luminaire) intensity [W/sr] (and where "sr" here denotes "steradian").

For x=X, y=Y, i.e., the LED or luminaire mounted directly above the target point, this reduces to $E=I_{LED}/Z^2$ as expected, where the x and y terms in the denominator account for the cosθ Lambertian shape away from the target point.

Figure 9:
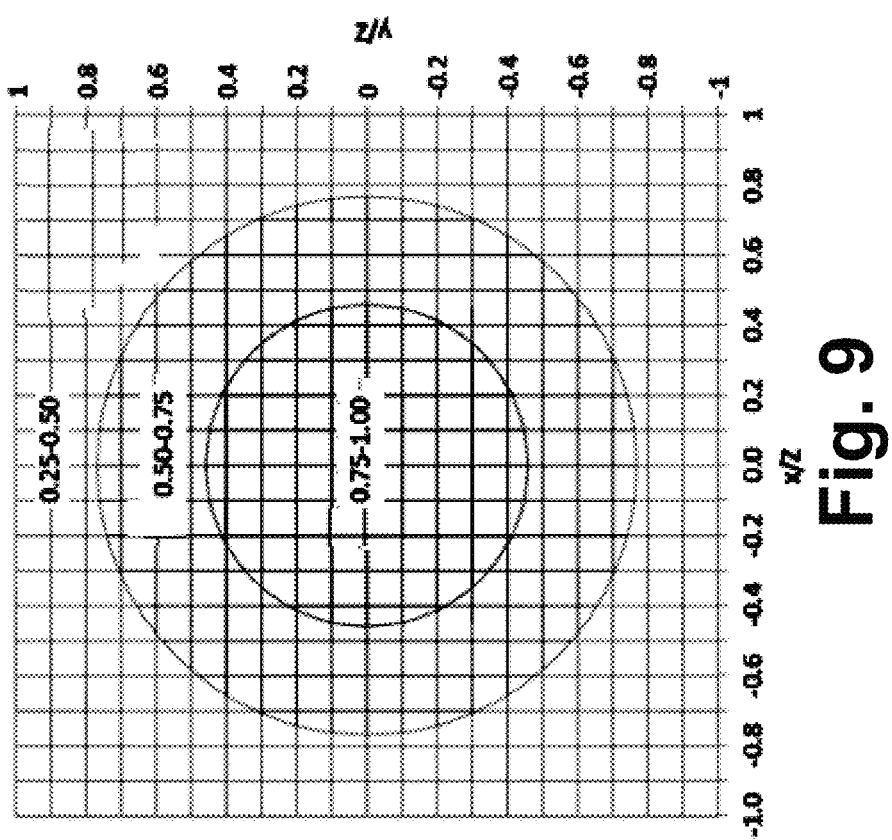
Figure 10:
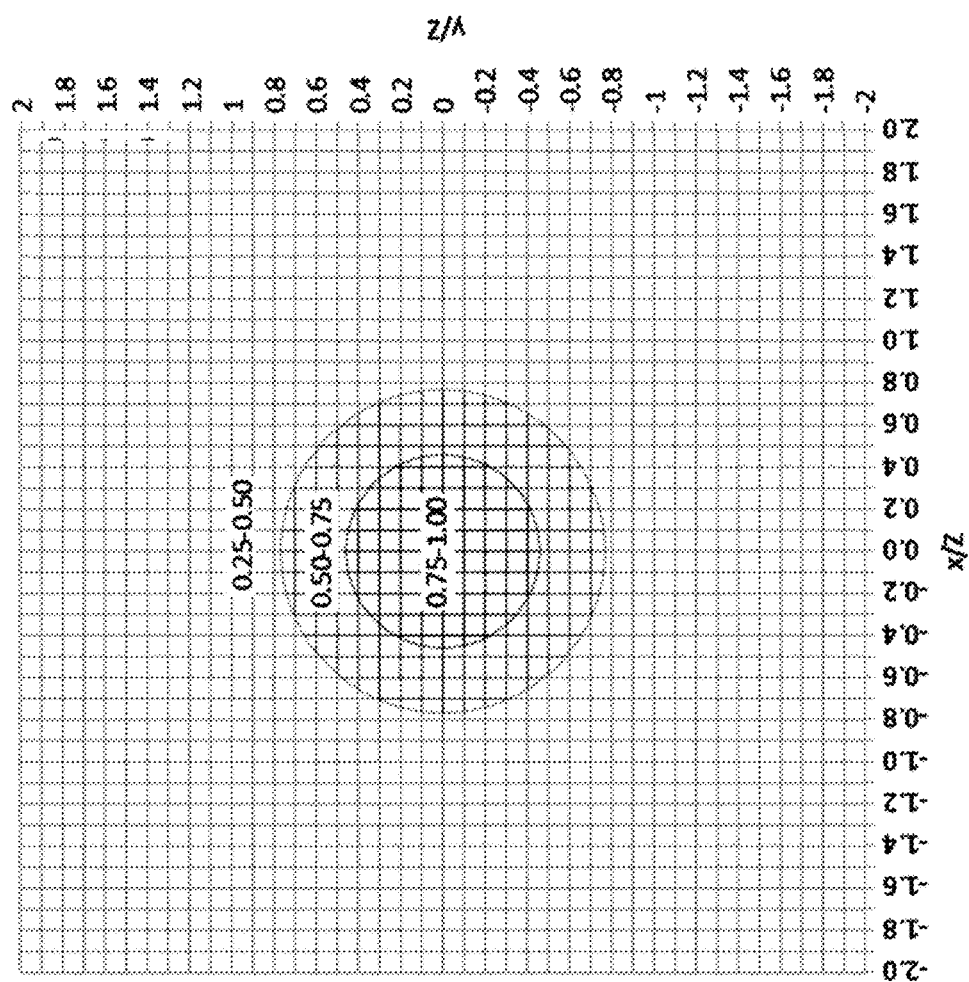
Figure 11:
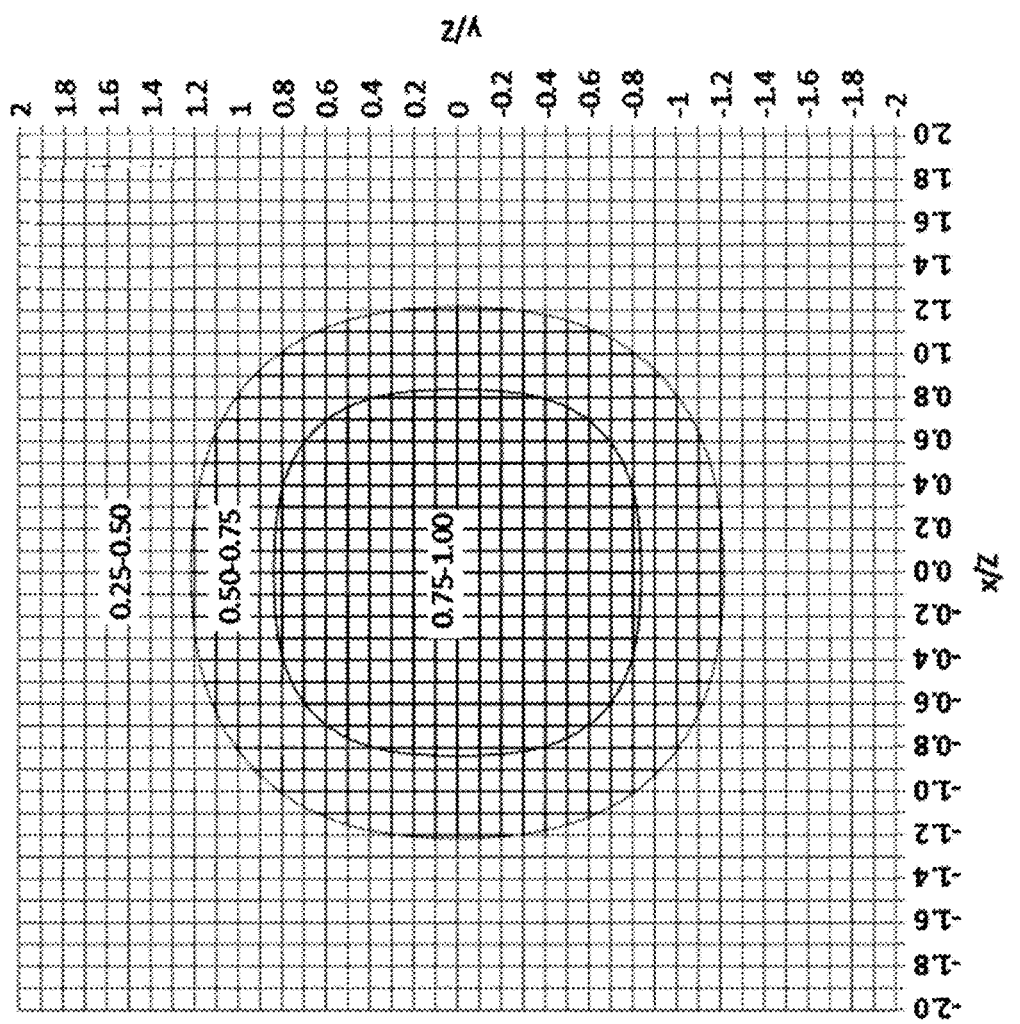
Figure 12:
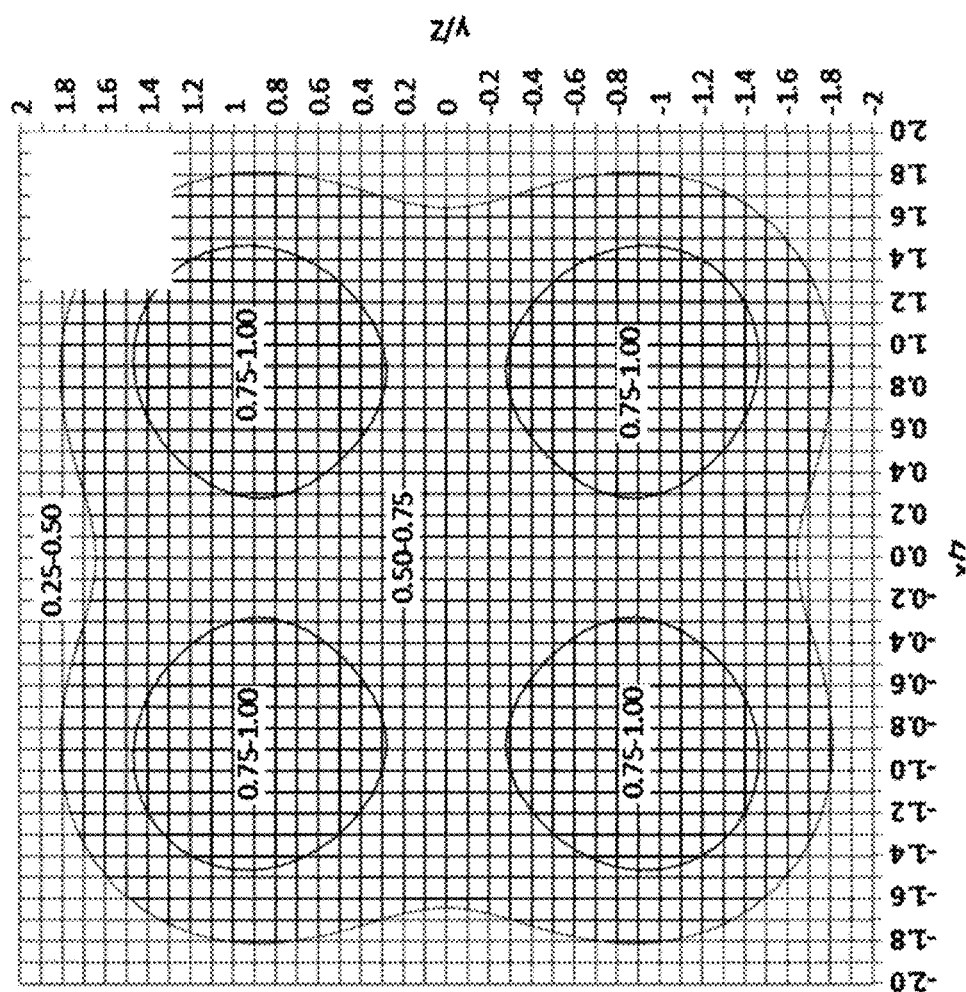
Figure 13:
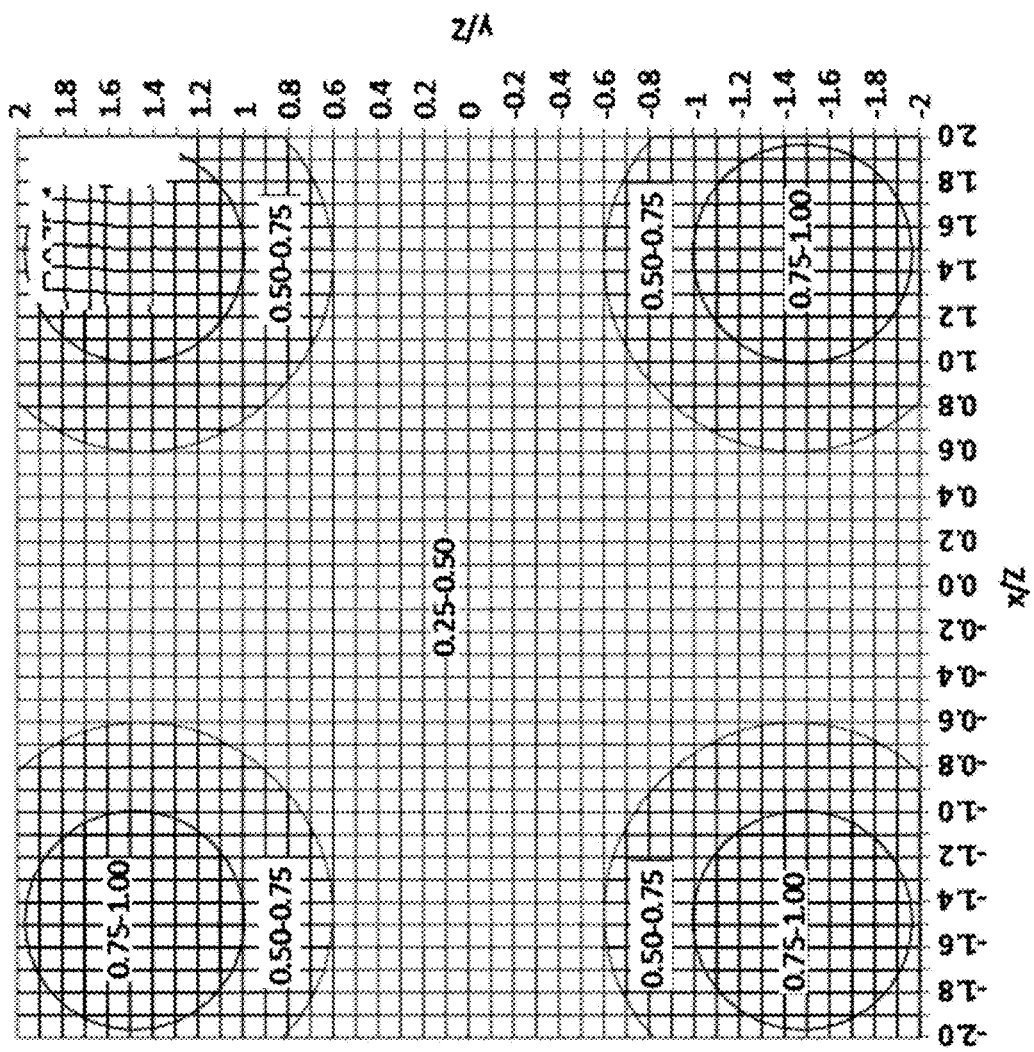
Figure 14:
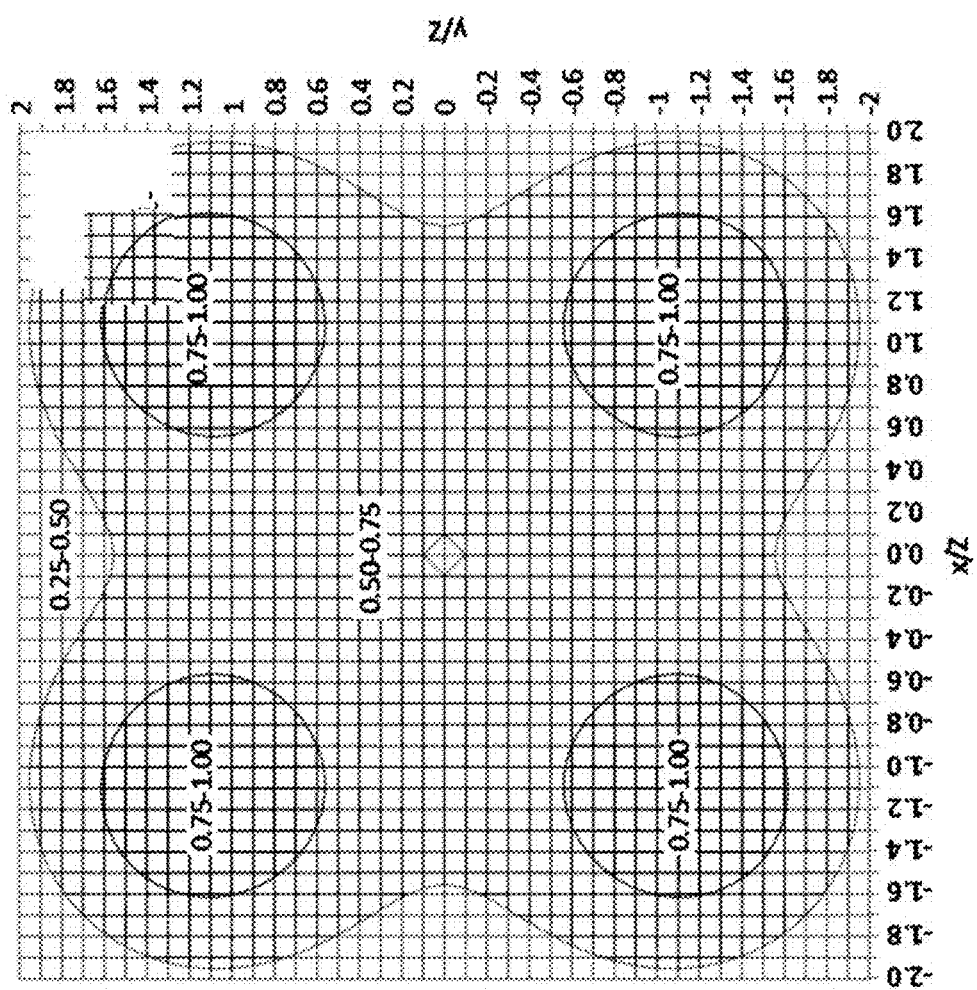

The spatial distribution of irradiance at positions x, y away from the target point (x=y=0) on the target plane (z=0), for a single LED or luminaire located at X=0, Y=0, Z is plotted in FIG. 9. In FIG. 9, regions with irradiance in the ranges "0.25-0.50", "0.50-0.75", and "0.75-1.00" are labeled, and boundaries therebetween delineated by curves. It is seen that the irradiance falls to a value of about 50% at a lateral distance from the target point of about 0.77 Z.

If, for the purpose of providing at least some minimum inactivation of a pathogen, it is desired that every point on the target surface have irradiance exceeding 50% of the maximum irradiance, then for example if the target plane is the floor lying 10 feet below the single LED or luminaire, with the maximum irradiance being directly below the LED or luminaire, the irradiance will drop to 50% of maximum at a distance about 7.7 feet away from the target point on the floor. If the design intent is to provide irradiance on the floor to be at least 50% of the max irradiance, then the effective irradiated zone would be a circle on the floor having a radius of about 7.7 feet. The irradiance on the remainder of the floor would be too low to provide desired minimum inactivation of the pathogen. To solve this problem, it is desired to have a plurality of LEDs or luminaires spaced apart such that the minimum irradiance anywhere on the floor will exceed 50% of the maximum.

The superposition of irradiances from a plurality of LEDs or luminaires is given by summing the contributions from each LED or luminaire in Equation (2) as in Equation (3), below:

$$E_{LED}(x, y, z) = \sum_{i=1}^{n} \frac{Z_n I_{LED,n}}{[(x - X_n)^2 + (y - Y_n)^2 + Z_n^2]^{1.5}} \quad (3)$$

For the case of a rectilinear array of LEDs or luminaires that are equally spaced along the x and y directions, i.e., a square array of luminaires, separated by distances x=y=aZ, where a=0, 0.5, 1.0, 1.5, 1.15 the results of Equation (3) are shown in FIG. 10, FIG. 11, FIG. 12, FIG. 13, and FIG. 14, respectively. In each of FIGS. 10, 11, 12, 13, and 14, regions with irradiance in the ranges "0.25-0.50", "0.50-0.75", and "0.75-1.00" are labeled, and boundaries therebetween delineated by curves. As the spacing between LEDs or luminaires increases from 0 (all LEDs or luminaires crowded together) toward a spacing equal to Z, the spatial coverage on the floor of irradiance within the range of 50-100% of maximum increases significantly from a lateral extent of 0.77 Z to 1.8 Z, reaching an optimal lateral extent of 1.95 Z with a spacing between LEDs or luminaires of 1.15 Z. This agrees with the result of the Moreno reference which provides a formula for the ideal spacing for a square array:

$$D = \sqrt{\frac{4}{3}} Z = 1.15Z \quad (4)$$

It may be expected that a more efficient array of LEDs or luminaires may result from a close-packed hexagonal array, rather than a square array, but typical grid layouts in ceilings tend to be square or rectangular, not hexagonal.

Therefore, in order to ensure that no portion of a target plane receives less than 50% of the irradiance received at the location of maximum irradiance (which will determine the exposure limit according to IEC 62471), the spacing between LEDs or luminaires should be no greater than about 1.15 times the distance from the LEDs or luminaires to the target irradiation plane. Referring again to FIG. 1, if the LEDs or luminaires 10 are mounted on or in the ceiling 4 at a height that is eight feet above the floor 6, and the floor 6 is the target plane, then the LEDs or luminaires should be spaced no further apart than about 9 feet in a square array. If, instead, the target plane is only about 3 feet below the ceiling 4, then the LEDs or luminaires should be spaced no further apart than about 3.5 feet in a square array. There is some preference for providing a greater number of LEDs or luminaires having a smaller spacing.

Of course, alternative solutions to improving uniformity are availed by modifying the angular distribution of radiation from the LEDs or luminaires using optics at additional expense per LED or per luminaire.

A preferred embodiment may be provided by minimizing the cost of each LED or luminaire so that a greater number may be used with less spacing between them.

Differentiation between inactivation of pathogens with UV-C and UV-A LEDs is next discussed.

The daily exposure limit allowed by IEC 62471 and ACGIH TLVs for UV-C radiation is 30 $J/m^2$ at the peak of the actinic hazard curve at 270 nm, and 60 $J/m^2$ at the nearby wavelength of 254 nm. By contrast, the exposure limit allowed by IEC 62471 for UV-A radiation ranges from 30 $kJ/m^2$ at 320 nm to 1000 $kJ/m^2$ at 400 nm, with 270 $kJ/m^2$ allowed at 365 nm. So, generally about 1000 times more irradiance is allowed in the UV-A than in the UV-C. If the maximum allowed UV-A dose is delivered at a constant flux over an 8-hour period, then the power density ranges from about 10 $W/m^2$ at 365 nm to about 40 $W/m^2$ at 400 nm.

Conversely, much less UV-C than UV-A is required to inactivate many pathogens to 99% or greater efficacy, typically by a factor of about $10^4$ to $10^5$ so that the allowed dose of UV-C during human occupancy is typically enough to inactivate many pathogens with 99% or greater efficacy. If the maximum allowed UV-C dose is delivered at a constant flux over an 8-hour period, then the power density at 254 nm is only about 2 $mW/m^2$.

The electrical efficiency of a UV-C LED at about 254 nm may be only about 0.5% (and about 2% at about 275 nm). Nonetheless, since the UV-C irradiance limit over 8 hours is only about 2 $mW/m^2$, then the electrical (and thermal) dissipation of the 254 nm LED will be only about 0.4 $W/m^2$. In contrast, with about 40% electrical efficiency, a 365 nm UV-A LED providing about 10 $W/m^2$ of UV-C irradiation will consume about 25 $W/m^2$ of electrical power and will dissipate about 15 $W/m^2$ of heat in the LEDs. Thereby, if the spacing of UV-A and UV-C LEDs or luminaires is about the same in a ceiling installation (to provided comparably uniform irradiation onto a target plane) then the UV-C LEDs will create only about 3% as much thermal load as the UV-A LEDs, and thereby may not require a heat sink (in the conventional sense of a heat sink component such as a metal component provided in thermal communication with the LEDs for the purpose of heat sinking the LEDs) in most viral disinfectant systems.

By reducing or eliminating the need for primary or secondary optics, and by reducing or eliminating the need for a heat sink, the application of UV-C LEDs for inactivation of pathogens at BEL doses for human occupancy facilitates a greatly simplified and cost-reduced design of the UV-C LED or luminaire.

Hence, one illustrative embodiment of UV-C LED or luminaire for inactivation of pathogens at BEL doses for human occupancy comprises a bare UV-C LED (no optics), with no (or minimal) heat sink structure, and providing direct irradiation of the target (e.g. the floor or other surface or material or the air or even a person) without any optical beam forming or spectral filtering. The relatively unencumbered LED or luminaire, with only an LED driver and optional control electronics, may be relatively small and light and inexpensive and may be mounted to any surface, requiring only a connection to a source of electricity.

In one illustrative embodiment of a UV-C LED luminaire, the form factor may be that of an LED puck, such as presently used for visible LEDs to provide illumination in a closet, undercabinet, or other restricted space. Such an embodiment is depicted in FIG. 2.

In another illustrative embodiment a UV-C LED may be attached to the outside of a traditional luminaire (i.e., for providing lighting) for example having the form factor of a ceiling troffer, typically having dimensions of 2×2 or 2×4 or 1×4 feet, for example. The troffer may provide visible illumination or UV-A irradiation or both.

Some further embodiments of the aspect of pulsing or otherwise time-modulating the emitted UV-C light, e.g. previously described with reference to blocks 54, 56 of FIG. 4, are next described.

Advantageously, the maximum allowed dose (EL) of 254 nm radiation in 8 hours (60 J/m$^2$) is expected to be sufficient to inactivate SARS-CoV-2 (and likely other coronaviruses) by at least 99% and possibly up to about 5-log or more. Since the allowed daily dose is based on cumulative (i.e. time-integrated) dose of UV-C energy, and is not restricted to any instantaneous UV-C power, it may be advantageous to tailor the temporal profile of the dose for greatest efficacy against airborne viruses, especially the SARS-CoV-2 and similar coronaviruses.

The SARS-CoV-2 virus has a spherical structure with a diameter of about 0.1 micron. The virus is primarily transferred between humans through the air, as opposed to via surfaces, water, or other means. The virus is introduced into the air as respiratory droplets by coughing, sneezing, singing or talking by the infected person, and the airborne virus particles then alight onto, or are then inhaled by, other people generally in the same interior space as the infected person. The virus may also be transmitted via air handling systems in the building, or less likely via exchange of air in the outdoors. While the transmission vectors of SARS-CoV-2 is an area of ongoing research, the present consensus is that the primary vector is air exchange from an infected person to other people sharing the same interior space.

The virus may typically be expelled from the infected person as a small droplet (typically ~2-20 μm diameter) containing the virus and about 1% by volume of non-volatile organics, such as mucus. Most of the liquid typically evaporates quickly, leaving the virus particles embedded in much smaller aerosol droplets, (typically ~0.2-5 μm diameter) comprising water and non-volatile organics which remain suspended in the air as an aerosol potentially for 1 to 3 hours or more. While the organic molecules, especially proteins, in the droplet may provide some protection for the virus from UV radiation, the virus is nonetheless about 10 times more susceptible to UV-C as an airborne particle than when it settles onto a surface or into water. Therefore, the virus should be preferentially irradiated by the disclosed viral disinfectant system while suspended in air.

A person breathing the contaminated air may need to be exposed for many minutes, typically about 20 minutes or longer, in order to inhale enough virus to become infected. Of course, with higher concentrations of virus in air, as introduced by a cough or a sneeze, the (statistically) required time may be shorter, and with enhanced ventilation in the space, it may be longer. It is therefore advantageous to deliver as much UV-C energy as feasible in a few minutes' time whenever there is an anticipated elevated exhalation of infectious virus, for example when more than one person occupies the same interior space, or if loud talking, singing, coughing, or sneezing is occurring.

In one illustrative embodiment, the irradiance may be elevated by about 2-100 times the 8-hour average dose rate when it is determined that multiple people occupy the space and especially if talking, singing, coughing, or sneezing is occurring. Sensors for monitoring occupancy (e.g., the motion sensor 40 of FIG. 2 and corresponding method of FIG. 5; or the microphone 42 of FIG. 3 and corresponding method of FIG. 6) may establish the timing of elevated doses.

Viruses may have enhanced susceptibility to elevated irradiances, so that the delivery of the allowed 60 J/m$^2$ may be more efficacious if delivered at high instantaneous power levels for short periods of time. It is also advantageous to deliver a dose exceeding the D90 dose in a time less than the required time for a susceptible subject to inhale enough virus to become infected, for example less than a few minutes, or less than about 20 minutes, or less than about an hour.

In some illustrative embodiments, the instantaneous power level may be increased substantially above the time-averaged power level in a pulsed mode (see block 54 of FIG. 4 and related discussion), where the maximum power exceeds the time-average power by at least 50%, more preferably by about 2× to 100× or more. Since the UV-C radiation is invisible, the frequency and duration of the pulses is not limited by the need to avoid the appearance of visible flicker.

Rate constants for 90-99% inactivation of pathogens may be estimated using a first-order exponential decay model, since these levels of inactivation are usually achieved by first-stage decay of the viruses. See Kowalski 2009. In general, any pathogen having D90<30 J/m$^2$, may also have D99<60 J/m$^2$ at 254 nm and thus may be inactivated with a BEL dose by at least 99% while the space is occupied by humans. A survey of D90 doses in air and on surfaces (and in water) for more than 100 bacteria and viruses is provided in Kowalski 2009.

With reference now to FIGS. 15-19 which present Tables 1-4, the virus and bacteria data in air and on surfaces are summarized. In Tables 1-4 of FIGS. 15-19, the headings are explained as follows.

Type: ss or ds means single-stranded or double-stranded RNA or DNA for viruses; sp=spore and veg=vegetative for bacteria.

D90 is the dose in J/m$^2$ required to inactivate 90% of pathogens in a population.

Media: air or s=surface.

RH=relative humidity.

Dia.=diameter of the pathogen.

Base Pairs=number (in kb=kilobases) of RNA or DNA pairs of bases in the pathogen—A,T,C,G for DNA; A, U,C,G for RNA.

UL is the Upper Limit of dose in J/m$^2$ for which the log-linear, single-stage inactivation applies in each reference. It represents the dose below which it may be assumed that an additional 10-times inactivation is achieved for each additional D90 amount of dose applied.

$Log_{10}$ inactivation is the base-10 logarithm of the fraction of surviving pathogens at a dose of 60 J/m$^2$, which is the maximum allowed dose in 8 hours at 254 nm. $Log_{10}$ inactivation is calculated assuming the log-linear relationship between dose and inactivation pertaining to the first stage of inactivation in two limits:

Max $log_{10}$ inactivation=60/D90, without regard to UL (upper limit).

Min $log_{10}$ inactivation=minimum of 60/D90 and UL/D90.

The range between min and max $log_{10}$ inactivation represents the inactivation achieved at a BEL dose within 8 hours, based on the data provided in each reference.

Any min $log_{10}$ inactivation >2.0 suggests that at least 99% of the pathogen will be inactivated at a BEL dose within 8 hours.

Any max $log_{10}$ inactivation >2.0 for which min $log_{10}$ inactivation <2.0 suggests that at least 99% of the pathogen may be inactivated at a BEL dose within 8 hours, but that the data provided is insufficient to validate the expectation of 99% inactivation.

The data in Tables 1-4 presented in FIGS. 15-19 were obtained assembling all of the data in Appendix A from Kowalski 2009 and by averaging the values in multiple rows of identical pathogens. Since the range of D90 values for any given pathogen often exceeds 10 times, a geometric mean is a more appropriate representation of the data than an arithmetic mean. In Tables 1-4 presented in FIGS. 15-19, multiple rows of D90 are averaged with a geometric mean, and the min and max $\log_{10}$ inactivation values are calculated from the geometric mean. Values of $\log_{10}$ inactivation exceeding 2.0 are highlighted with a gray background. The summary row below each table shows the % of the rows for which at least 99% inactivation is expected.

With reference to FIG. 20 which presents Table 5, a summary is shown of the percentage of pathogen species that are inactivated by at least 99% by 60 J/m$^2$ at 254 nm. Table 5 indicates that most of the viruses are at least 99% inactivated and that all of the viruses are inactivated by at least about 90% in air by 60 J/m$^2$ @ 254 nm.

Table 1 (FIG. 15) particularly indicates that both coronavirus and Influenza A are at least 99% inactivated in air by 60 J/m$^2$ at 254 nm. It is especially encouraging that D90 for coronavirus is only 3 J/m$^2$, about 20 times less than the maximum allowed dose in 8 hours, suggesting that coronavirus may be inactivated by >99.9% by a BEL 8-hour dose at 254 nm. Table 1 also indicates a D90 of only 12 J/m$^2$ and range of 1.5-5.1 $\log_{10}$ inactivation in air at the max allowed dose @ 254 nm of 60 J/m$^2$.

With reference to FIG. 21 which presents Table 6 showing geometric means of $\log_{10}$ inactivation of viruses at 254 nm on surfaces, these results indicate that most viruses are not inactivated by 90% or more on surfaces by 60 J/m$^2$ at 254 nm. However, only one of the pathogens appears in both Tables 5 and 6 for direct comparison of inactivation in air and on surfaces. That is the Adenovirus, which indicates about 7 times higher D90 on surfaces than in air, in agreement with the apparent general trend that viruses are more susceptible in air than on surfaces to an EL dose of 60 J/m$^2$ of 254 nm radiation.

Table 3 (FIG. 17) indicates that most of the bacteria are inactivated by 90-99% or more in air by 60 J/m$^2$ at 254 nm. Table 3 particularly indicates that *S. aureus* and possibly *E. coli* are at least 99% inactivated in air by 60 J/m$^2$ at 254 nm.

Table 4 (FIG. 18) indicates that about one-half of the bacteria are inactivated by at least 99% on surfaces by 60 J/m$^2$ at 254 nm. Table 4 particularly indicates that *S. aureus* is probably only about 90% inactivated on surfaces by 60 J/m$^2$ at 254 nm. This is in contrast with UV-A radiation at 365 nm which provides about 99% inactivation of *S. aureus* on surfaces at an EL dose in 8 hours.

A June 2020 pre-print publication reports that SARS CoV-2 virus is inactivated by at least 3-log10 with 37 J/m2 (vs. 60 J/m2 EL dose) @ 254 nm in water. https://doi.org/10.1101/2020.06.05.20123463 (Bianco). A May 2020 pre-print publication reports that SARS CoV-2 virus is inactivated by at least 6-$\log_{10}$ with 400 J/m$^2$ (vs. 60 J/m$^2$ EL dose) @ 254 nm in water (Patterson) https://doi.org/10.1101/2020.05.21.108035. A June 2020 press release reported results from Boston University and Signify (BU & Signify) that SARS CoV-2 virus is inactivated by at least 2-$\log_{10}$ with 12 J/m$^2$ at 254 nm on surfaces, https://www.hospimedica.com/covid-19/articles/294783097/uv-c-light-kills-sars-cov-2-virus-within-seconds-of-exposure-in-lab-study. A June 2020 pre-print publication (Inagaki) reports that SARS CoV-2 virus is inactivated with D90 of 42 J/m$^2$ at 280 nm in water. https://doi.org/10.1101/2020.06.05.20123463. An August 2020 pre-print publication (Kitigawa) reports that SARS CoV-2 virus is inactivated with D90 of 11 J/m$^2$ at 222 nm on surfaces. https://doi.org/10.1016/j.ajic.2020.08.022. A July 2020 pre-print publication (Heilingloh) reports that SARS CoV-2 virus is inactivated with D90 of 722 J/m2 at 254 nm in aqueous solution, although the SARS-CoV-2 was harvested from cell culture in DMEM, such that even after clarification to remove cell debris, the fluid is still DMEM which typically provides as much as about 10× protection to the virus from UV, such that the expected D90 in a standard aqueous solution may be expected to be about 10× lower, https://doi.org/10.1016/j.ajic.2020.07.031.

Table 6 (FIG. 21) compiles the D90 inactivation data from the six above references. For each of the six datasets, a linear interpolation is used, if necessary, to estimate the D90 dose, required for a 1-$\log_{10}$ inactivation. None of the 6 reports is measured in air, which is the medium of interest for inactivation of the SARS-CoV-2 virus in its two most probably transmission mechanisms: as airborne droplets or as suspended aerosols. Therefore, the reported inactivation data for SARS-CoV-2 must be estimated in air from the measured values in aqueous media and on surfaces.

As shown in Table 7 (FIG. 22), water is generally protective of viruses, reducing the UV rate constant by factors ranging from 2.5× to 40×, with a geometric mean of 8× from 8 published datasets. Therefore, the D90 dose in water from the Bianco, Patterson, Inagaki, and Heilingloh results may be expected to be lower on average by about a factor of 8× if measured in air. Kowalski 2009 states that surfaces are likewise protective of viruses against UV-C radiation, by about a factor of about 10× in D90, pertaining to the BU/Signify and Kitigawa data.

With reference to FIG. 24 presenting table 8, based on the estimated enhancement factor of 0.12 for k (inverse of dose) in Table 7 (FIG. 22), the results for SARS CoV-2 measured in water and on surfaces in the six pre-prints may be estimated in Air as shown in the second column of D90 data in Table 8.

Figure 23:
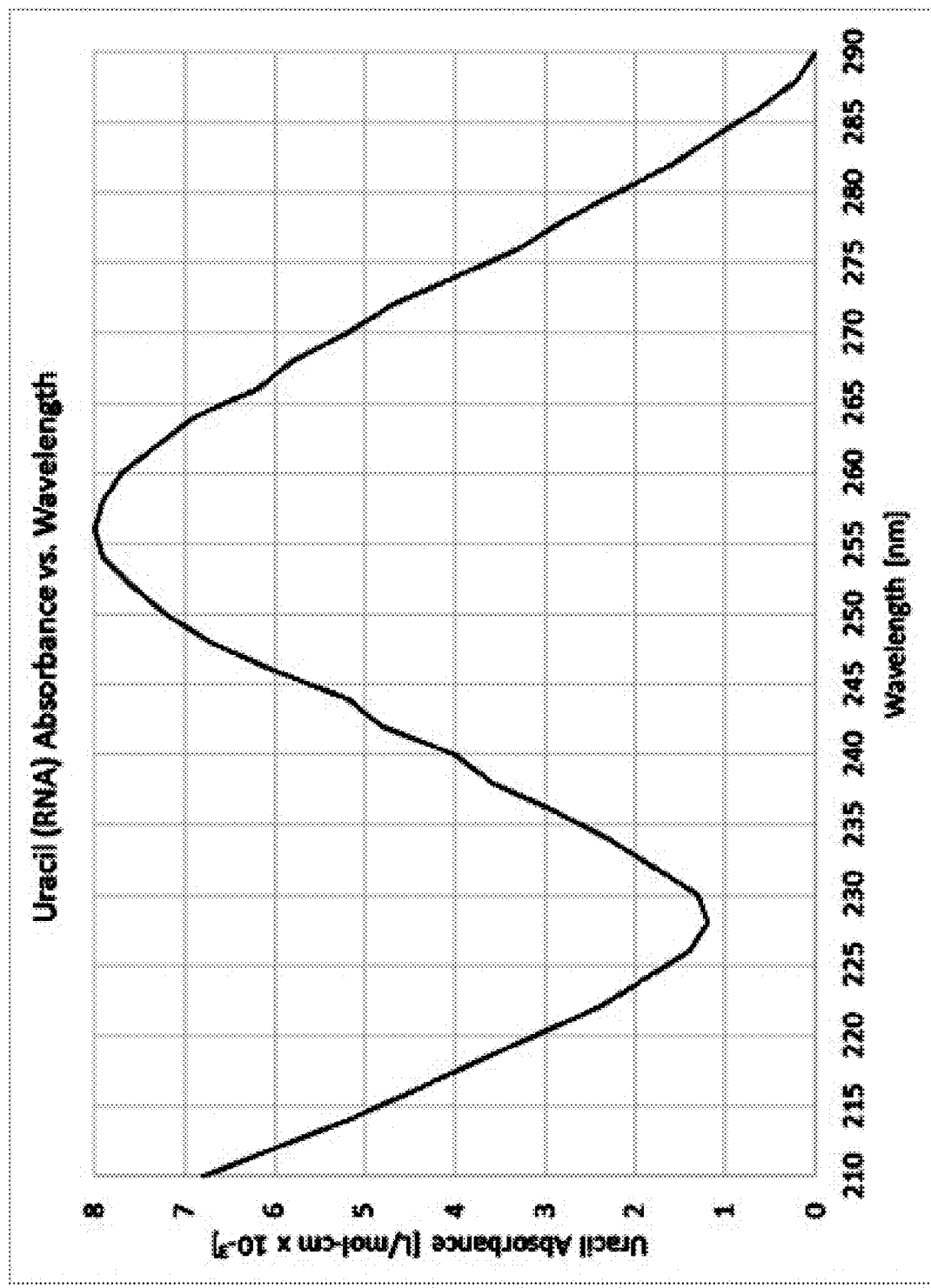

Two of the six reports of UV inactivation of SARS-CoV-2 were obtained at UV-C wavelengths other than 254 nm, namely 280 (Inagaki) and 222 nm (Kitigawa). Although there exist no reports of UV-C action spectra (inactivation vs. wavelength) for SARS-CoV-2 virus, the wavelength dependence may be estimated from the absorbance vs. wavelength of the nucleic acid, Uracil, that is known to be responsible for most of the UV inactivation for RNA viruses, such as coronaviruses, as shown in FIG. 23.

The Uracil absorbance values at 222, 254, and 280 nm are 2.8, 7.9, and 2.2 L/mol-cm×10$^{-3}$, respectively, demonstrating the high relative susceptibility of RNA viruses to UV-C at about 254 nm. By assuming that D90 for the SARS-CoV-2 reports at 280 and 22 nm may be estimated to be proportional to the Uracil absorbance at their respective wavelengths vs. the absorbance at 254 nm, then D90 may be estimated at 254 nm per the right-most column in FIG. 24. As seen in the bottom 4 rows of geometric means of the 6 values for D90 in air, the expected D90 for SARS-CoV-2 in air at 254 nm may be in the range of about 2 to 4 J/m$^2$, with a most likely estimate of about 3 J/m$^2$.

Hence, based on the presently available data for SARS CoV-2, indicating an estimated D90 in air at 254 nm of about 3 J/m$^2$, it is expected that 60 J/m$^2$ of 254 nm irradiation will provide inactivation between 2-$\log_{10}$ (99%) and 10-$\log_{10}$ (complete sterilization is considered to be 6-$\log_{10}$) in air.

As previously noted, in some multispectral embodiments the inactivating UV-C light source 10 may be combined with a light source having an inactivating portion having wavelengths in the UV-A or other longer wavelength ultraviolet range, that is, longer than the UV-C range, e.g. of 280 to 380 nanometers, or with a light source having an inactivating portion in any other wavelength range from about 200 nm to about 3000 nm. This multispectral approach leverages the differences in inactivation effectiveness of longer wavelength ultraviolet versus UV-C for various pathogens to effectively target different pathogens or combinations of pathogens, e.g. viruses which are typically more effectively inactivated by UV-C and bacteria which are typically more effectively inactivated by UV-A. Additionally, UV-B may be effective in preventing or reducing photo-repair of bacteria and other pathogens following irradiation by UV. Hence UV-B, although lacking high efficacy at inactivating pathogens alone, may be effective in combination with irradiation outside of the UV-B range. Certain medium-pressure Hg lamps; and Xenon (Xe) lamps, especially pulsed Xe lamps, may be used as sources of UV-B, with or without spectral filters to isolate the UV-B portion of the emission. Visible (Vis) and infrared (IR) light sources are capable of delivering doses sufficient to overheat the cell membranes or other organelles of a pathogen, so that in combination with the biological disruptions caused by UV or other wavelengths, the overall inactivation may be enhanced. Vis and IR light sources may be repetitively pulsed to deliver extremely high instantaneous heating of the pathogen, even though the time-average output of the light source may be designed for safe use in an occupied space. High intensity Vis and IR light sources are available in many lamp types, such as incandescent, halogen, high-pressure discharge lamps, LEDs, et cetera. This capability may be further enhanced by the extreme intensities enabled by the emerging capabilities of laser diodes, providing pulse times in the nanosecond range and becoming available at wavelengths throughout the UV, Vis and IR.

As further disclosed herein, in such a multispectral embodiment it is contemplated to provide a control for adjusting a distribution of the actinic budget across different spectral components (e.g. various in the UV-A, UV-B, UV-C, visible, and infrared in various embodiments) to address potentially dynamically changing disinfection goals. This aspect recognizes that the actinic limit is a constraint on the entire spectrum of ultraviolet light emitted by the multispectral light source, with the contribution of each wavelength component being weighted based on the wavelength dependence of the actinic hazard (see FIG. 7 and related text). The actinic dose delivered by the multispectral light source may be set to have a higher actinic dose fraction of UV-C versus UV-A, or vice versa. For example, during an outbreak of a viral pathogen it may be desired to increase the UV-C actinic dose fraction to increase the germicidal efficacy for viruses, and to concurrently reduce the UV-A actinic dose fraction to keep the total actinic dose delivered by the light source under the actinic limit. This operating mode is suitable for a viral outbreak since UV-C is more effective for inactivating viruses compared with UV-A. If at some later time, if the viral pathogen outbreak has subsided but a bacterial pathogen is now of greater concern, as would be typical in a hospital or healthcare environment, then the actinic dose budget may be shifted to increase the UV-A actinic dose fraction to increase the germicidal efficacy for bacteria, while concurrently reducing the UV-C actinic dose fraction in order to keep the total actinic dose delivered by the light source under the actinic limit.

The disclosed actinic dose budgeting is optionally more finely targeted. For example, in a hospital setting, the actinic dose budget may be individually set for specific patient rooms based on the pathogen infecting each patient. In another variant embodiment, one or more biosensors could be deployed to detect a dominant pathogen at a particular room or other location, and the actinic dose budget across the available spectral peaks of the multispectral light source is adjusted to target that specific pathogen when detected. The adjustment may be based on first principles (e.g., UV-C is more effective against viral agents while UV-A is more effective against bacterial agents) or based on empirical data such as a UV spectrum experimentally optimized to maximize inactivation efficacy for a specific pathogen species. Hence, while the illustration of targeting virus pathogens with UV-C versus bacterial pathogens with UV-A is provided as an example, it is contemplated to employ greater pathogen specificity targeting based, for example, on laboratory experiments demonstrating a particular efficacy of a certain UV actinic dose distribution across the available spectral peaks.

With reference now to FIG. 25, an illustrative example is diagrammatically shown of a multispectral (here UV-C and UV-A) light source for disinfection which is implemented as a single light fixture 80 that includes UV-C LEDs 82 and UV-A LEDs 84 along with driver and control electronics 86. In one suitable physical layout, the UV-C LEDs 82 may be disposed on a first (UV-C) printed circuit board (PCB) 92 which optionally may include power conditioning circuitry; and the UV-A LEDs 84 may be disposed similarly disposed on a second (UV-A) PCB 94 which again optionally may include power conditioning circuitry. Alternatively, the UV-C and UV-A LEDs may be disposed on a single PCB, or the UV-C (or UV-A) LEDs may be distributed across multiple PCBs.

In some embodiments, the driver and control electronics 86 do not include an electronic processor. For example, the driver and control electronics 86 of the light source 80 may comprise an analog or digital clock set to operate the UV-C and UV-A LEDs 92, 94 during a set time interval (e.g. 9:00 am to 5:00 pm for an office that is staffed from 9 am to 5 pm; or 8:00 am to 8:00 pm for a retail store that is open from 8 am to 8 pm; or so forth).

Alternatively, the driver and control electronics 86 may optionally include an electronic processor (e.g. a microprocessor or microcontroller) programmed to implement an actinic dose budget parser 96 that controls the outputs of the UV-C LEDs 82 and the UV-A LEDs 84 based on a control input. In another embodiment, the actinic dose budget parser 96 is implemented by analog circuitry or by digital circuitry that does not include an electronic processor. In general, the actinic dose fraction delivered by each UV LED set 82, 84 is controlled by adjusting the electrical current (or voltage) applied to the LEDs to adjust the output intensity. That is, the relative intensities of the light sources of the plurality of light sources are adjusted while keeping the actinic dose of the emitted disinfection light below the dose limit for actinic radiation exposure. In some embodiments, the control input is a manually supplied control input, e.g., provided wirelessly via a control application 100 running on a cellular telephone or other mobile device 102 operated by a building manager or other authorized person which transmits the control signal that is wirelessly received by a wireless transceiver (or wireless receiver) 104 of the driver and control electronics 86. Alternatively, the manually supplied control input may be implemented as a manual switch or other manual control built into the fixture 80. For example, the actinic dose budget control may in some embodiments have only two settings: (1) one setting to relatively increase the UV-C actinic dose fraction over the UV-A actinic dose fraction to emphasize virus inactivation over bacteria inactivation; and (2) the other setting to relatively increase the UV-A actinic dose fraction over the UV-C actinic dose fraction to emphasize bacteria inactivation over virus inactivation. In this case, the manual control could be a two-setting switch that can be set to: Setting 1—virus inactivation; or Setting 2—bacterial inactivation. (It should be noted that in this embodiment the virus inactivation setting may optionally still have some non-zero UV-A actinic dose fraction to provide some bacterial inactivation; and likewise the bacteria inactivation setting may optionally still have some non-zero UV-C actinic dose fraction to provide some viral inactivation). Other embodiments are contemplated, e.g. a three-position switch, a toggle switch, et cetera.

In yet another contemplated embodiment, the control input is automatically provided by one or more biosensors 106 that are integrated with the fixture 80 (as shown) or separate from the fixture but in wired or wireless communication with the electronics 86. The biosensor(s) 106 may employ any conventional biosensing technology (e.g., electrochemical, ion channel switch, fluorescent biosensor, et cetera) to detect a specific pathogen or class of pathogens. The biosensor(s) may be mounted on the fixture 80 as shown or may be mounted elsewhere and connected to the fixture electronics 86 by a wired (e.g. USB cable or DALI) or wireless (e.g. WiFi, Bluetooth, or Zigbee) connection.

To provide feedback control of the intensities of the UV-C LEDs 82 and UV-A LEDs 84, respectively, it is optionally contemplated to incorporate a UV-C-sensitive sensor, e.g. a photodiode 112 to directly measure the UV-C intensity and likewise a UV-A-sensitive sensor, e.g. a photodiode 114 to directly measure the UV-A intensity. In another non-limiting illustrative approach, open-loop control can be used based on a UV-C (or UV-A) output intensity versus drive current (or voltage) calibration that is predetermined for the specific fixture 80 or for that make/model of fixture 80.

With reference to FIGS. 26-30, some additional embodiments of multispectral light sources for performing disinfection in an occupied (or, in some embodiments, unoccupied) space are described. FIG. 26 illustrates a single fixture 120 that provides UV-C disinfection light at two different wavelengths by way of a first set of UV-C LEDs 82-1 emitting at a first UV-C wavelength $\lambda_1$ that may be disposed on a first PCB 92-1 which optionally may include power conditioning circuitry; and a second set of UV-C LEDs 82-2 emitting at a second UV-C wavelength $\lambda_2$ (where $\lambda_1 \neq \lambda_2$) that may be disposed similarly disposed on a second PCB 92-2 which again optionally may include power conditioning circuitry. Alternatively, the two sets of UV-C LEDs 82-1, 82-2 may be disposed on a single PCB. In this embodiment, the two UV-C wavelengths $\lambda_1$ and $\lambda_2$ are selected to provide effective inactivation of a target pathogen or class of pathogens. In one non-limiting illustrative example, $\lambda_1$=255 nm and $\lambda_2$=280 nm. Optionally, the actinic dose budget parser 96 is included with the driver and control electronics 86 to control the relative actinic dose fractions of the respective UV-C LEDs 82-1, 82-2 based on a control input such as already described with reference to FIG. 25. That is, the relative intensities of the light sources 82-1, 82-2 of the plurality of light sources are adjusted based on the control input, while keeping the actinic dose of the emitted disinfection light below the dose limit for actinic radiation exposure.

FIG. 26 illustrates another example, in which a single fixture 130 provides both disinfection by way of UV-C LEDs 82 and UV-A LEDs 84, and also illumination by way of white-light LEDs 132 (or, in other embodiments, a white fluorescent tube, white incandescent bulb, or other white light source). This arrangement is beneficially compact. Although not shown in FIG. 26, it is contemplated for the electronics 86 to include the actinic dose budget parser 96 (and optionally sensors) operating as described with reference to FIG. 25.

Figure 29:
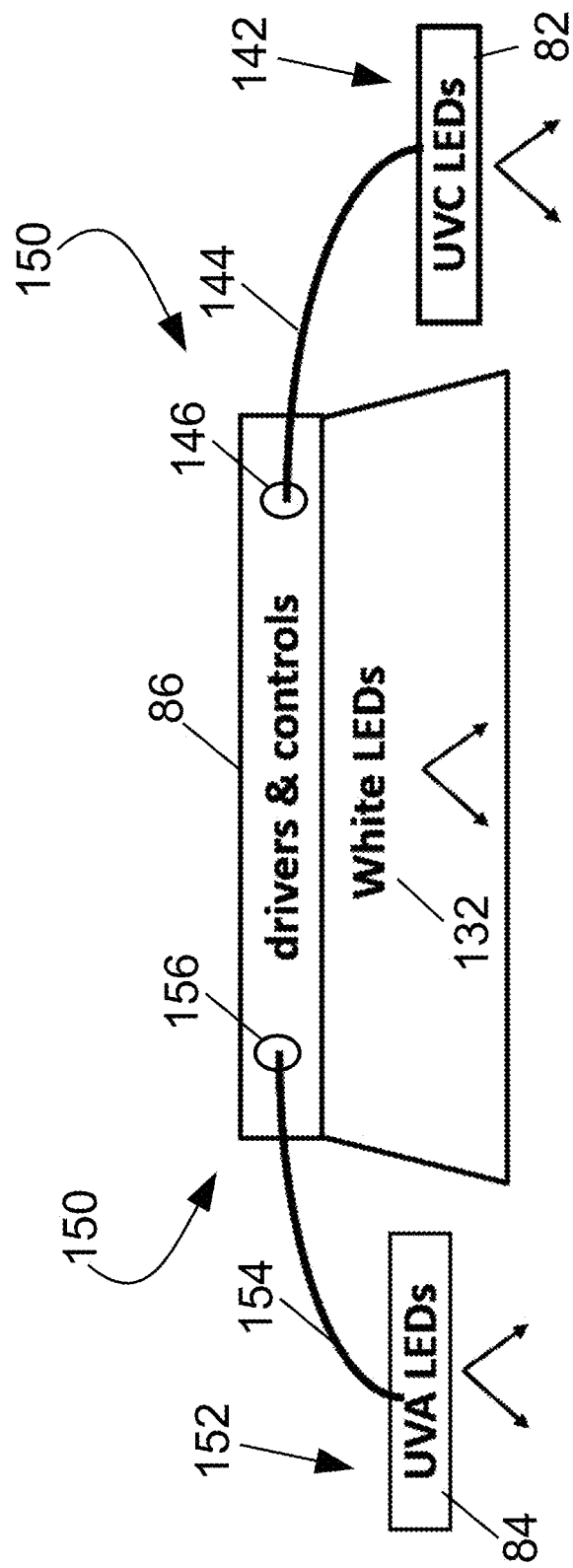

FIG. 28 illustrates an example similar to that of FIG. 26, except that in the example of FIG. 28 the UV-A LEDs 84 and the white LEDs 132 are mounted in a main fixture 140 while the UV-C LEDs 84 are mounted in an auxiliary fixture 142 connected with the driver and control electronics 86 by way of an electrical cable 144 connecting with a connector 146 of the main fixture 140. FIG. 29 illustrates an example similar to that of FIG. 28, except that here the main fixture 150 hosts only the white LEDs 132, with the UV-C LEDs 84 again mounted in the auxiliary fixture 142 and here with the UV-A LEDs 84 also mounted in an auxiliary fixture 152 which again is connected with the main fixture 150 by way of an electrical cable 154 connecting with a connector 156 of the main fixture 150. The arrangements of FIGS. 28 and 29 advantageously provide for modularity. For example, the main fixture 140 can be sold as a product and the auxiliary fixture or fixtures 142, 152 can be an optional add-on product(s).

Any of the fixture embodiments of FIGS. 25-29 may optionally include the actinic dose budget parser 96 to provide for adjusting the actinic dose budget between the UV LEDs of different wavelengths, that is, to adjust the relative intensities of the light sources of the plurality of light sources to be optimized for a particular disinfection task (e.g., to optimally inactivate a specific pathogen or class of pathogens) while keeping the actinic dose of the emitted disinfection light below the dose limit for actinic radiation exposure. Alternatively, any of the fixture embodiments of FIGS. 25-29 may omit the actinic dose budget parser 96, in which case the actinic dose fractions of the UV sources of the different wavelengths are fixed.

Figure 30:
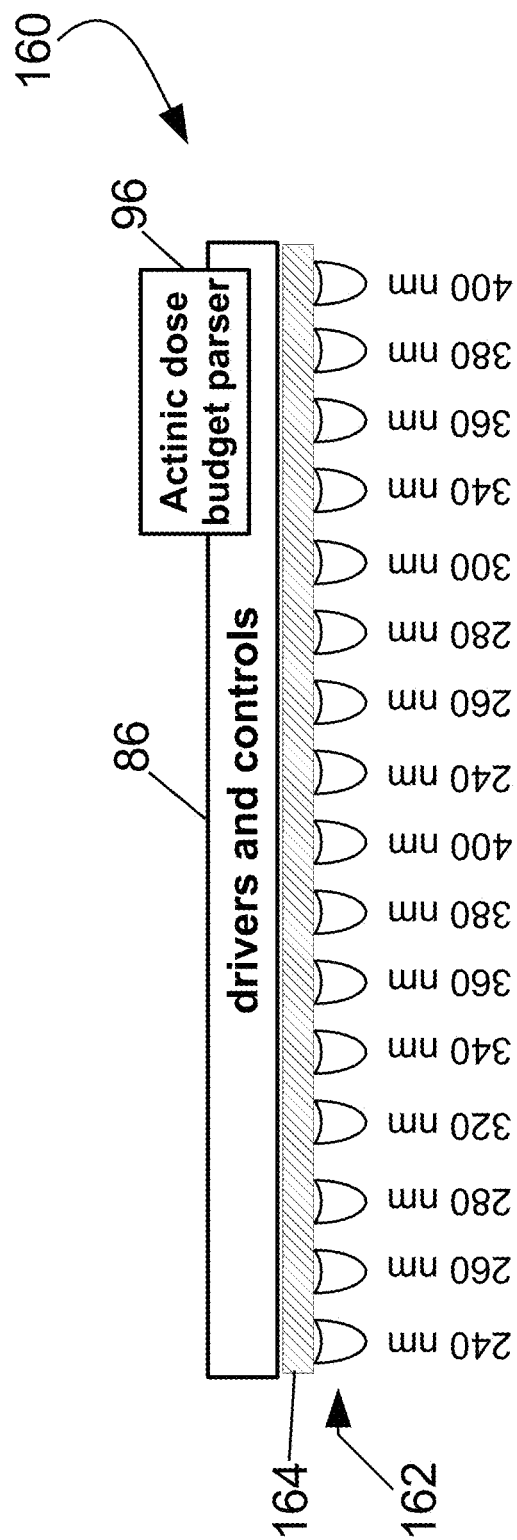

With reference to FIG. 30, UV LEDs enable near-exact selection of the inactivation wavelength for a given disinfection application. This is because LEDs are available with different peak wavelengths in about 5 nm increments, with about 10 nm linewidths (FWHM) throughout the UV, Visible, and Infrared regions of the electromagnetic spectrum. When combined with the actinic dose budget parser 96, in the embodiment of FIG. 30 this enables providing a light source for disinfection that provides a spectrum that is finely tailored for disinfecting a specific target pathogen. In the embodiment of FIG. 30, a single fixture 160 includes a bank of LEDs 162 with emission peaks at the labeled wavelengths in the (non-limiting illustrative) range of 240 nm to 400 nm inclusive in (non-limiting illustrative) 20 nm increments (except omitting an LED emitting at 300 nm which is in the UV-B range), mounted on a PCB 164 with the drivers and controls electronics 86 including the actinic dose budget parser 96. In this embodiment, the spectrum can be tuned in 20 nm increments to match an experimentally determined optimal spectrum for inactivating a specific target viral or bacterial pathogen. For example, in the event of an outbreak of a specific pathogen, laboratory tests can be performed to optimize the UV spectrum for inactivating that specific pathogen. The actinic dose budget parser 96 is then set to energize the LEDs 162 of the various wavelengths to output actinic dose fractions in accord with (an approximation of)

that empirically determined optimized UV spectrum, scaled in total dose to ensure the total dose remains below the EL. (Optionally, if the fixture 160 further or is operatively connected with includes an occupancy sensor, then the output can be scaled up above the EL when the space is determined to be unoccupied, as previously described with reference to FIG. 5). It will be appreciated that FIG. 30 is diagrammatic, and the LEDs of the various peak wavelengths may optionally be distributed in various ways over the two-dimensional area of the PCB 162. Moreover, while the illustrative fixture 160 contains LEDs 162 in the wavelength range 240-400 nm spanning large portions of the UV and violet spectral range, it is contemplated to include LEDs extending into other wavelength regions, such as UV-C wavelengths below 240 nm (e.g. 230 nm), and/or the visible and infrared regions insofar as visible and infrared radiation can be effective for inactivating some types of pathogens.

As noted, the illustrative fixture 160 of FIG. 30 omits an LED emitting at 300 nm which is in the UV-B range. This is based on the observation that light in the UV-B range is typically less effective for inactivating pathogens, while having a high actinic hazard. Nonetheless, this is an illustrative example, and in some embodiments one or more of the LEDs may be emitting in the UV-B range.

While reference is made to LEDs in describing the embodiments of FIGS. 25-30, it is to be appreciated that in some embodiments the LEDs may consist of a single LED, e.g. the UV-C LEDs 82 may consist of a single UV-C LED 82. Moreover, in other embodiments some or all of the LEDs may be replaced by other types of light sources (possibly including spectral filters) emitting at the design-basis wavelength peaks. For example, a low-pressure mercury lamp may be substituted for the UV-C LEDs.

In the following, some contemplated multispectral UV disinfection light source embodiments are described in terms of some contemplated spectral components. In these examples, while a light source is referenced, it is to be understood the light source may be implemented by way of multiple fixtures, e.g. as in the examples of FIGS. 28 and 29.

In one illustrative embodiment, a multispectral light source includes a plurality of inactivating portions (or spectral regions), including a first inactivating portion having wavelengths in the UV-A range and at least a second inactivating portion having wavelengths outside of the UV-A range, e.g. a first inactivating portion having wavelengths in a range of about 320 nm to about 380 nm, and a second inactivating portion having wavelengths in a range below about 320 nm or in a range greater than about 380 nm, the accumulated actinic dose of the combined inactivating portions controlled by the actinic dose budget parser 96 to be below the exposure limit for human occupancy (e.g., the actinic UV hazard exposure limit for exposure to ultraviolet radiation incident upon the unprotected skin or eye apply to exposure within any 24-hour period). For radiation having wavelengths longer than 320 nm other photobiological hazards must also be considered, for example the limit on total UV-A radiation between 320 and 400 nm; the blue light hazard limit that peaks in the blue range of the visible spectrum; and thermal hazards related to longer wavelengths, including IR wavelengths. For the purposes of pathogen inactivation, the actinic hazard is typically the most limiting of all photobiological hazards, but each hazard must be considered separately, in which case the actinic dose budget parser 96 is suitably replaced by a more general total hazard dose budget parser that considers each hazard limit separately.

In another illustrative embodiment, a multispectral light source is configured to generate light in an environment for human occupancy, the light including a plurality of inactivating portions, including a first inactivating portion having wavelengths in the UV-C range and at least a second inactivating portion having wavelengths outside of the UV-A range, e.g. a first inactivating portion having wavelengths in a range of about 200 nm to about 280 nm, and a second inactivating portion having wavelengths in a range greater than about 280 nm, the accumulated actinic dose of the combined inactivating portions controlled to be below the exposure limit for human occupancy.

In another illustrative embodiment, a multispectral light source configured to generate light in an environment for human occupancy includes a plurality of inactivating portions, including a first inactivating portion having wavelengths in the UV-A range and a second inactivating portion having wavelengths in the UV-C range, and at least a third inactivating portion having wavelengths outside of the UV-A and UV-C ranges, e.g. a first inactivating portion having wavelengths in a range of about 320 nm to about 380 nm, and a second inactivating portion having wavelengths in a range of about 200 nm to about 280 nm and a third inactivating portion having wavelengths in a range greater than about 380 nm or between about 280 nm and about 320 nm, the accumulated actinic dose of the combined inactivating portions controlled to be below the exposure limit for human occupancy (EL).

In further illustrative embodiments, a multispectral light source configured to generate light in an environment for human occupancy includes three or more inactivating portions.

In some illustrative embodiments, a multispectral light source configured to generate light in an environment for human occupancy emits light in two or more discrete peaks, for example corresponding to UV-A LEDs emitting at a peak in the UV-A spectrum (320 nm to 400 nm inclusive) and UV-C LEDs emitting at a peak in the UV-C spectrum (100 nm to 280 nm inclusive), and optionally further including one or more additional LEDs such as violet LEDs emitting at a peak in the violet spectrum (380 nm to 450 nm inclusive; for example, a violet LED whose peak wavelength is at greater than 400 nm, which which is visible to many individuals; or more particularly in some embodiments a violet LED whose peak wavelength is at 405 nm, or in another embodiment 425 nm, or so forth). In some non-limiting illustrative embodiments, the total emission intensity of the multispectral light source outside of these two or more discrete peaks is less than 40% of the total intensity emitted by the multispectral light source.

In the following, the benefits of a multispectral light source for disinfection that emits (at least) one or more peaks in the UV-A spectrum and one or more peaks in the UV-C spectrum are next further explained.

It is recognized herein that UV-C exposure is particularly efficacious for inactivating virus pathogens, even at dose levels acceptable in an occupied space (BEL), and that UV-A exposure is particularly efficacious for inactivating bacterial pathogens, even at dose levels acceptable in an occupied space (BEL). For example, a single coronavirus particle is extremely small, having a size of about 0.1 micron in diameter. The particles of many other pathogenic viruses are comparably small, e.g. well under 1 micron in diameter or length in many cases. As a result, UV-C radiation can penetrate the outside capsid or protective layer of a virus and damage the nucleic acid contained inside a virus particle very rapidly, while it's suspended in air, e.g. in less than eight hours, or less than about 1 to 3 hours, or less than about 10 to 30 minutes, with a time-accumulated dose of about 10 J/m² or less (the dose at 254 nm required to inactive about 90% of a typical virus in air). In another example, a single bacterium is typically larger, having a size of about 1-10 microns in diameter or length. As a result, UV-C radiation which easily penetrates a small virus particle, typically cannot penetrate with sufficient dose to damage the nucleic acids of bacteria sufficiently to inactivate the bacteria. Instead, UV-A is typically efficacious in inactivating bacteria by depositing its energy in the outer membrane of the cell, or the cell wall, where the energy of the UV-A photon is sufficient to create reactive oxygen species (ROS) or to drive other chemical reactions that may cause enough damage to the cell envelope to inactivate the bacterium.

Since, historically most UV-C disinfection was achieved using low-pressure mercury (Hg) lamps utilizing the exceptional germicidal efficacy of the dominant 254 nm resonance line of Hg at intensities well above the exposure limit for human occupancy (above the EL), most published data for UV inactivation of pathogens is provided at 254 nm. Other legacy light sources provide a range of other broad-band inactivating UV light sources, notably medium-pressure Hg lamps, Xenon lamps, and Excimer lamps. Often, a narrow-band or pass-band filter is incorporated to select only the desired wavelengths of these legacy light sources. On the other hand, UV LEDs enable near-exact selection of the inactivation wavelength for a given disinfection application, with LEDs becoming available in about 5 nm increments, with about 10 nm line-widths throughout the UV, Visible, and Infrared regions of the electromagnetic spectrum. Optionally, this enables providing a light source for disinfection that provides a spectrum that is tailored to optimally inactivate a specific target pathogen, as previously described with reference to FIG. 30.

By way of a specific illustration, a study of aerosolized coronavirus suggests that the virus particles typically remain suspended in indoor air for about 1 to 3 hours or longer, eventually settling onto a surface. Once a virus particle settles onto a surface, it typically requires about 10 times higher dose to inactivate it than the dose required in air as an aerosol (2009 Kowalski). Furthermore, public guidance from the U.S. Centers for Disease Control (CDC) (circa July 2020) advises that coronavirus particles may be propelled by as much as 6 feet from the mouth of a person speaking, even further if shouting, coughing or singing, and as far as 20 feet or more from a sneeze, and it is believed that the primary vector for transmission is inhalation of airborne virus, and that typically an exposure of about 20 minutes in air contaminated with virus may be sufficient to infect the person inhaling the air. For the above reasons, it is advantageous to inactive a virus while it is airborne, before it settles on a surface (in less than about 1 to 3 hours), and most preferably before a sufficient dose is inhaled to infect a person (in less than about 20 minutes). If the infectious person exhaling the virus and the susceptible person inhaling the virus are in close proximity for an extended period of time, then a sufficient dose of UV-C may desirably be provided to inactivate at least about 90% of the virus while the space is occupied to reduce the probability of infection. Since the exhaled viral contamination in any indoor space will diffuse into all available volume within the space within a few minutes, it is also desired to provide UV-C irradiation throughout the space, especially while the space is occupied, and for a period following termination of occupation, providing a dose sufficient to inactivate at least 90% of the virus in the ambient air in the space.

For coronaviruses, and many other viruses, a major transmission vector is by way of respiratory droplets (>5 micron diameter) or aerosols (<5 micron diameter) produced when an infected person coughs, sneezes, talks, shouts, or sings. In one model of this transmission vector, the droplets evaporate quickly (within seconds to a few minutes), leaving virions (infectious virus) enveloped in a mucus-water particle suspended in ambient air for on the order of one to three hours or more before settling onto surfaces. In a room, vehicle cabin, an aircraft cabin, train compartment, or other (at least mostly) enclosed environment for human occupancy, this means that airborne virus particles present a transmission threat for about an hour or more after an infected person leaves the environment.

In any space occupied by people, it's likely that both viral and bacterial contamination may be present in the space. Although the very small and light virus particles may remain airborne for many hours before settling onto a surface, the larger and heavier bacteria are either transferred from surface-to-surface, or if released into the air, settle onto a surface quickly. The primary vector for transmission of bacterial disease is via surfaces or liquids. Bacteria can remain viable on surfaces for many days, or in the case of spores and fungi, indefinitely long. Further, unlike the potential for airborne transmission of virus between people in just a few minutes, the likely time frame for transmission of bacteria, spores, or fungi via surface transfer may be many hours or days. Therefore, it may be advantageous to provide a constant, low-level direct irradiance of UV-A onto surfaces, not exceeding the Exposure Limit for human occupancy (DIBEL), so that surfaces may be continuously cleaned of bacteria, spores, or fungi even when the space is occupied by humans.

Some regulatory schemes set the dose limit for actinic radiation exposure (EL) at 270 nm to 30 J/m² over an eight-hour period, with higher doses allowed at longer and shorter UV wavelengths. For example, the Exposure Limits at 254 and 270 nm are 60 and 30 J/m² (respectively) and at 365 nm (UV-A) it is about 273,000 J/m², about 10,000 times higher. While 60 J/m² is a low dose, as discussed herein, since a typical virus is about 90% inactivated by about 10 J/m² in air at 254 nm, the relatively high Exposure Limit allowed during 8 hours for human occupation provides a window for employing disinfection of viruses in air in occupied spaces by way of UV-C light at BEL doses. However, since a typical bacterium requires about 30 J/m² for 90% inactivation at 254 nm on surfaces (about 3 times more dose than for typical viruses in air), UV-C surprisingly may not be generally as effective at inactivating bacteria as it is at inactivating viruses in occupied spaces. It will be shown that in general, UV-A is more efficacious than UV-C, each at their respective Exposure Limits, in inactivating bacteria on surfaces in occupied spaces. Therefore, it may be advantageous to combine UV-A and UV-C light sources in the same space for human occupation, each operating within the allowed Exposure Limit for actinic radiation (with BEL doses), in order to most efficaciously inactivate both viruses and bacteria. Similarly, it is expected that the inactivation efficacy for pathogens such as fungi, spores, or so forth may be wavelength dependent as can be determined by laboratory experimentation.

With reference now to FIG. 31, a table is shown which summarizes D90 doses at 254 nm for various categories of pathogens in water, on surfaces, and in low and high relative humidity air. The data presented in FIG. 31 is from 2009 Kowalski. In the table of FIG. 31, the cells highlighted in gray indicate D90 doses for which inactivation of at least 90-99% is expected with an EL dose at the EL=60 J/m² for 254 nm. This indicates that of all the categories of pathogens (virus, bacteria, fungi) in combination with media (air, surface, water), virus in air is the most susceptible to UV-C at 254 nm. Bacteria in air are similarly, but less, susceptible as viruses.

The table of FIG. 31 pertains to UV-C at 254 nm only. There is a relative sparsity of published data to fill in the corresponding cells of the table for any UV-A wavelengths. Some values for UV-A inactivation relative to UV-C for the same pathogen and medium may be obtained from the relatively few publications of Action Spectra covering the entire UV range, or specific studies comparing UV-A and UV-C rate constants.

Figure 32:
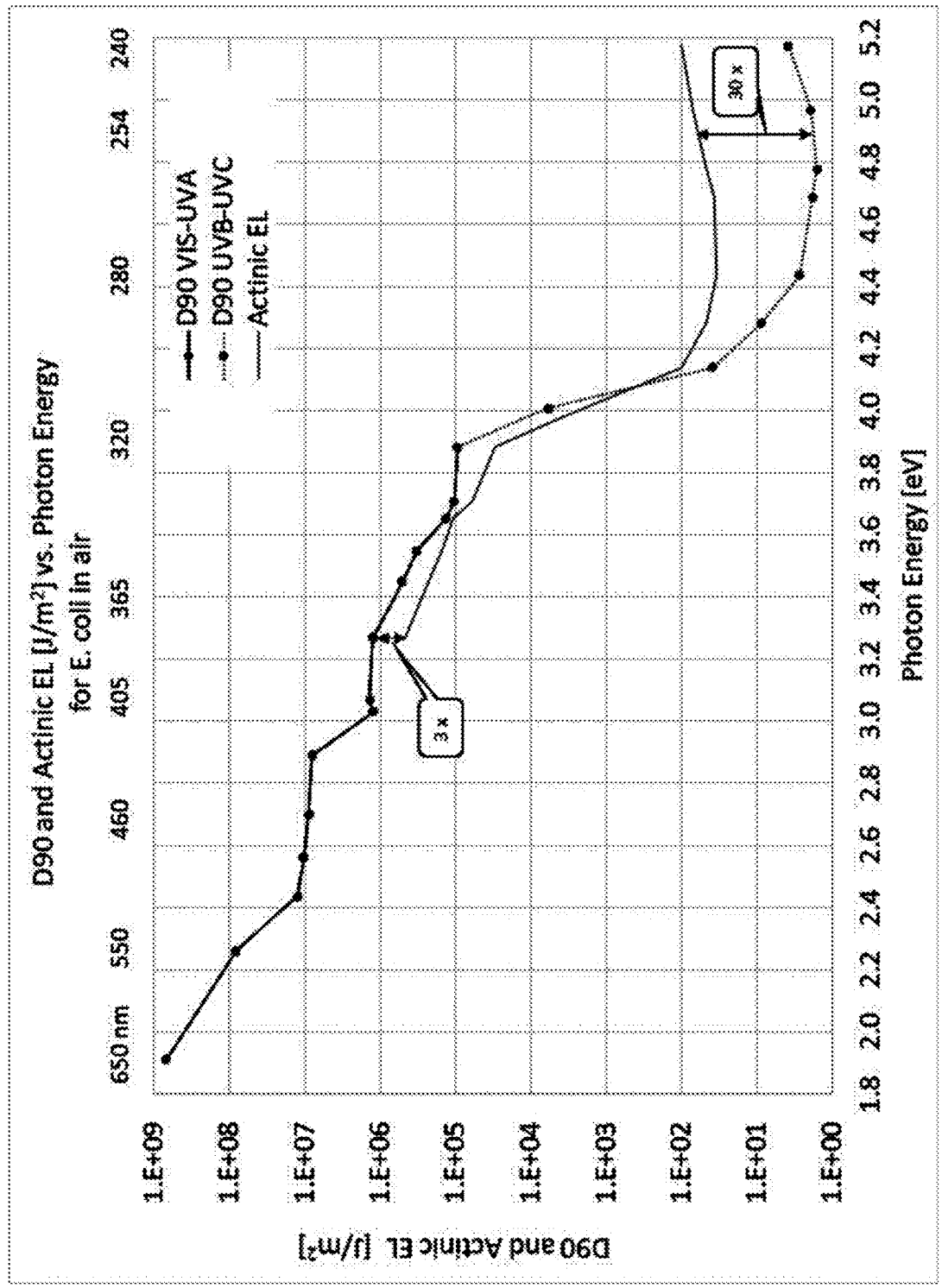

With reference now to FIG. 32, an example is plotted for the case of $E.$ $coli$ in air, from which D90~7×10⁵ J/m² in the UV-A (365 nm) vs. D90~2 J/m² in the UV-C (254 nm). D90 for $E.$ $coli$ in air at 254 nm (2 J/m²) is about 30 times lower than the EL at 254 nm (60 J/m²) as labeled in FIG. 32 by the difference label "30x", but is about 3 times greater than the EL at 365 nm (273,000 J/m²) as labeled in FIG. 32 by the difference label "3x". Therefore, $E.$ $coli$ may be easily inactivated by at least 99% in air at the EL for 254 nm, but not even 90% inactivated in air at the EL for 365 nm.

With reference to FIG. 33, another example is provided, which compares the D90 values for various bacteria inactivated in aqueous media at 3 UV wavelengths, 365 (UV-A), 302 (UV-B), and 254 nm (UV-C). The data presented in FIG. 33 is a summary of D90 doses and $\log_{10}$ inactivation at 365, 302, and 254 nm for various bacteria in aqueous solution and on dry surfaces, from 2013 Santos (Architectural Microbiology, 195:63-74, DOI 10.1007/s00203-012-0847-5) and 2020 Kvam (Journal of Photochemistry & Photobiology, B: Biology 209 (2020), https://doi.org/10.1016/j.jphotobiol.2020.111899). It can be seen that the Geometric Mean of $\log_{10}$ inactivation at the EL corresponding to each UV wavelength are comparable at 365 and 254 nm (0.5 and 0.8, respectively) whereas the inactivation at the EL for 302 nm is insignificant. One variety of bacteria, Brevibacterium, is actually more efficaciously inactivated at the EL for 365 nm than at the EL for 254 nm. Similarly, because the Geometric Means are comparable at 365 and 254 nm, it may be expected that other bacteria may be more efficaciously inactivated at 365 nm EL than at the 254 nm EL. In particular, 3 bacteria commonly responsible for healthcare acquired infections ($S.$ $aureus,$ $E.$ $faecalis,$ $E.$ $coli$) are shown to be inactivated on dry surfaces (typical of occupied indoor surfaces) by >>2-$\log_{10}$ at the EL for 365 nm, emphasizing the unexpected efficacy of 365 nm radiation within the allowed EL during human occupation.

By way of summary, it is clear that UV-C radiation at 254 nm within the allowed EL (BEL) is especially efficacious for inactivating most viruses in air; and that UV-A radiation at 365 nm is especially efficacious for inactivating particular bacteria of interest to public health on dry surfaces, as they may exist in healthcare, residential, and other occupied spaces.

Returning now to the embodiment of FIG. 30, in which the fixture 160 includes a set of LEDs in the range 240-400 nm, optimization of the spectrum by the actinic dose budget parser 96 can be performed as follows. To generalize, it is assumed that the fixture provides N sets of one or more LEDs each, emitting at respective wavelengths $\lambda_1, \ldots, \lambda_N$. Each wavelength has a corresponding germicidal coefficient $k_{germ}$, for example taken from FIG. 7 or from empirical (i.e. experimental) data for a specific target pathogen. Each wavelength further has a corresponding actinic hazard coefficient $\lambda_{act}$, for example also taken from FIG. 7. Then the actinic dose is given by:

$$D_{act} = \sum_{i=1}^{N} k_{act,i} H_i < \text{actinic limit, EL} \quad (5)$$

where $H_i$ denotes the "radiant exposure" or "dose" [J/m²] of the LEDs indexed by index i. As indicated in Equation (5), the actinic dose budge parser 96 must keep this actinic dose $D_{act}$ below the actinic limit, EL=30 J/m². On the other hand, the germicidal efficacy, $E_{germ}$, can be expressed as:

$$E_{germ} = \sum_{i=1}^{N} k_{germ} H_i \quad (6)$$

where again $k_{germ,i}$ is the germicidal coefficient for the LEDs indexed by i. Hence, it is desirable to maximize the germicidal efficacy, $E_{germ}$, for the specific pathogen by maximizing Equation (6) while ensuring the constraint $D_{act}$<actinic limit, EL as set forth in Equation (5) is satisfied. The actinic dose budget parser 96 suitably does this by adjusting the radiant exposures or doses $H_i$, i=1, ..., N for example using a least squares optimization (e.g., Levenberg-Marquardt algorithm).

More generally, the actinic dose budget parser 96 comprises an electronic processor programmed to optimize the radiant exposures (i.e. doses) of the light sources with different disinfection peak wavelengths of the multispectral light source to maximize germicidal efficacy for a target pathogen subject to a total actinic dose of the optimized radiant exposures (i.e. doses) of the light sources being at or below an actinic limit. In addition to optimizing the average irradiance produced as described with reference to Equations (5) and (6), the actinic dose budget parser 96 may also optimize the radiant exposures (i.e. doses) of the light sources with different disinfection peak wavelengths of the multispectral light source in a time-dependent manner, for example so as to maximize germicidal efficacy for a target pathogen during events likely to produce high airborne pathogen densities, while still being subject to the total actinic dose of the optimized radiant exposures (i.e. doses) of the light sources being at or below an actinic limit. Examples of this time-dependent actinic dose budge parsing are described by way of nonlimiting illustration with reference to FIGS. 4-6 (e.g., the example of FIG. 6 increases UV-C intensity in response to a detected vocalization that may be indicative of talking, singing, coughing, sneezing, or some other vocalization likely to be producing increased airborne pathogen concentration.

The following clauses provide additional disclosure.

Clause 1: A disinfection system comprises at least one light source configured to emit light into an environment for human occupancy to inactivate one or more pathogens in the environment for human occupancy. The light includes an inactivating portion in a range of 200 nanometers to 280 nanometers inclusive, and in some embodiments in a range of 240 nanometers to 280 nanometers inclusive. The light emitted by the at least one light source is effective to produce an actinic dose at a target plane in the environment of 30 J/m² or less over an eight hour period, wherein the target plane is 2.1 meters or closer to a floor of the environment for human occupancy.

Clause 2: The disinfection system of Clause 1 wherein the irradiation of the light emitted into the environment for human occupancy by the at least one light source is effective to achieve at least 90% inactivation in air of the one or more pathogens in the environment within 8 hours or less. Clause 3: The disinfection system of Clause 2 wherein the irradiation of the light emitted into the environment for human occupancy by the at least one light source is not effective to achieve at least 90% inactivation of the one or more pathogens on surfaces in the environment within 8 hours or less. Clause 4: The disinfection system of any one of Clauses 1-3 wherein the at least one light source is spaced from the one or more surfaces by a distance large enough for the light to have the irradiance at the one or more surfaces of 60 J/m² or less over an eight hour period. Clause 5: The disinfection system of any one of Clauses 1-4 wherein the environment for human occupancy is a room having a ceiling, a floor, and walls, and the at least one light source includes one or more light sources configured for mounting on the ceiling and/or wall of the room. Clause 6: The disinfection system of any one of Clauses 1-4 wherein the environment for human occupancy is a ground vehicle cabin, an aircraft cabin, or a train compartment. Clause 7: The disinfection system of any one of Clauses 1-5 wherein the at least one light source comprises at least one mercury lamp which may or may not include a phosphor. Clause 8: The disinfection system of Clause 6 wherein the at least one mercury lamp comprises at least one low-pressure mercury lamp. Clause 9: The disinfection system of any one of Clauses 1-8 wherein the at least one light source comprises one or more light emitting diodes. Clause 10: The disinfection system of any one of Clauses 1-9 wherein each light source of the at least one light source does not include a heat sink. Clause 11: The disinfection system of any one of Clauses 1-10 wherein each light source of the at least one light source does not include any refractive optical component. Clause 12: The disinfection system of any one of Clauses 1-10 wherein each light source of the at least one light source includes a UV-C transmissive refractive or diffractive component arranged to direct the light toward the one or more surfaces. Clause 13: The disinfection system of any one of Clauses 1-12 wherein each light source of the at least one light source includes a UV-C reflective mirror arranged to direct the light into the environment. Clause 14: The disinfection system of any one of Clauses 1-13 wherein each light source of the at least one light source comprises a light emitting diode (LED) or gas discharge lamp with no refractive optic component. Clause 15: The disinfection system of any one of Clauses 1-14 wherein the inactivating portion has peak wavelength in a range of 200 nanometers to 280 nanometers inclusive. Clause 16: The disinfection system of any one of Clauses 1-14 wherein the inactivating portion has peak wavelength in a range of 200 nanometers to 270 nanometers inclusive. Clause 17: The disinfection system of any one of Clauses 1-15 wherein each light source of the at least one light source includes a lightbulb base for mating with a lightbulb socket. Clause 18: The disinfection system of Clause 17 wherein the lightbulb base is one of an Edison screw lightbulb base, a bayonet lightbulb base, a bi-post lightbulb base, or a bi-pin lightbulb base. Clause 19: The disinfection system of any one of Clauses 1-18 wherein the at least one light source is configured to generate the light as pulses having a peak irradiance that is at least 1.5 times the time-averaged irradiance. Clause 20:

The disinfection system of any one of Clauses 1-19 further comprising a sensor configured to detect occupancy of the environment for human occupancy, and an electronic processor configured to control the at least one light source to generate the light into the environment based on the occupancy of the environment for human occupancy detected by the sensor. Clause 21: The disinfection system of Clause 20 wherein the electronic processor is configured to control the at least one light source to initiate the generation of the light into the environment or to increase irradiance of the light in response to the sensor detecting occupancy of the environment for human occupancy. Clause 22: The disinfection system of Clause 21 wherein the electronic processor is further configured to control the at least one light source to stop the generation of the light into the environment or to decrease the intensity of the light a predetermined time after the sensor detects a cessation of occupancy of the environment for human occupancy. Clause 23: The disinfection system of Clause 22 wherein the predetermined time is between one and three hours inclusive. Clause 24: The disinfection system of any one of Clauses 20-23 wherein the sensor includes a motion sensor. Clause 25: The disinfection system of any one of Clauses 20-23 wherein the sensor includes a microphone and the electronic processor is configured to detect human vocalization in the environment for human occupancy using the microphone and to control the light source to initiate the generation of the light into the environment or to increase intensity of the light in response to the detecting human vocalization. Clause 26: The disinfection system of Clause 25 wherein the electronic processor is further configured to control the light source to stop the generation of the light into the environment or to decrease the intensity of the light in response to the sensor a predetermined time after the sensor detects a cessation of the human vocalization in the environment for human occupancy.

Clause 27: A viral disinfection light source comprises a light source including a lamp or one or more LEDs disposed on a substrate, wherein the light source is configured to emit light including an inactivating portion having peak wavelength in a range of 200 nanometers to 280 nanometers inclusive, and in some embodiments more preferably in a range of 240 nanometers to 280 nanometers inclusive. Clause 28: The viral disinfection light source of Clause 27 wherein the light source comprises one or more LEDs disposed on a substrate. Clause 29: The viral disinfection light source of Clause 28 wherein the one or more LEDs disposed on the substrate include UV-C LEDs emitting light including the inactivating portion having peak wavelength in a range of 200 nanometers to 280 nanometers inclusive (and in some embodiments in a range of 240 nanometers to 280 nanometers inclusive) and longer wavelength LEDs emitting light in a longer wavelength inactivating range of 280-380 nm. Clause 30: The viral disinfection light source of Clause 28 wherein the one or more LEDs disposed on the substrate include UV-C LEDs emitting light including the inactivating portion having peak wavelength in a range of 200 nanometers to 280 nanometers inclusive (and in some embodiments in a range of 240 nanometers to 280 nanometers inclusive) and longer wavelength LEDs emitting light in a longer wavelength inactivating range of 300-380 nm. Clause 31: The viral disinfection light source of Clause 27 wherein the light source comprises a mercury lamp. Clause 32. The viral disinfection light source of Clause 31 wherein the light source comprises a low-pressure mercury lamp. Clause 33: The viral disinfection light source of any one of Clauses 27-32 wherein the light source does not include a heat sink. Clause 34: The viral disinfection light source of any one of Clauses 27-33 wherein the inactivating portion has peak wavelength in a range of 200 nanometers to 280 nanometers inclusive (and in some embodiments in a range of 240 nanometers to 280 nanometers inclusive). Clause 35: The viral disinfection light source of any one of Clauses 27-33 wherein the inactivating portion has peak wavelength in a range of 200 nanometers to 270 nanometers inclusive (and in some embodiments in a range of 200 nanometers to 270 nanometers inclusive). Clause 36: The viral disinfection light source of any one of Clauses 27-35 wherein at least 90% of the intensity of the light emitted by the light source is in a wavelength range of 240 nanometers to 280 nanometers inclusive. Clause 37: The viral disinfection light source of Clause 36 wherein the light source includes a spectral bandpass filter having a passband in the wavelength range of 240 nanometers to 280 nanometers inclusive. Clause 38: The viral disinfection light source of any one of Clauses 27-37 wherein the light source includes a lightbulb base that fits a lightbulb socket. Clause 39: The viral disinfection light source of Clause 38 wherein the lightbulb base is one of an Edison screw lightbulb base, a bayonet lightbulb base, a bi-post lightbulb base, or a bi-pin lightbulb base. Clause 40: The viral disinfection light source of any one of Clauses 27-39 further comprising a controller configured to control the light source to emit the light as pulses having pulse width of 1 second or less and pulse spacing of at least 10 seconds.

Clause 41: The viral disinfection light source of any one of any one of Clauses 27-40 further comprising a motion sensor, and a controller configured to control the light source to turn the light source on or increase the intensity of the light emitted by the light source in response to motion detected by the motion sensor, and to turn the light source off or decrease the intensity of the light emitted by the light source in response to cessation of motion detected by the motion sensor for a predetermined time interval.

Clause 42: The viral disinfection light source of any one of any one of Clauses 27-40 further comprising a microphone, and a controller configured to control the light source to turn the light source on or increase the intensity of the light emitted by the light source in response to vocalization detected by the microphone, and to turn the light source off or decrease the intensity of the light emitted by the light source in response to cessation of vocalization detected by the microphone for a predetermined time interval.

Clause 43: The viral disinfection light source of any one of any one of Clauses 27-40 further comprising a motion sensor, and a controller configured to control the light source to turn the light source off or decrease the intensity of the light emitted by the light source in response to motion detected by the motion sensor, and to turn the light source on or increase the intensity of the light emitted by the light source in response to cessation of motion detected by the motion sensor for a predetermined time interval.

Clause 44: The viral disinfection light source of any one of any one of Clauses 27-40 further comprising a microphone, and a controller configured to control the light source to turn the light source off or decrease the intensity of the light emitted by the light source in response to vocalization detected by the microphone, and to turn the light source on or increase the intensity of the light emitted by the light source in response to cessation of vocalization detected by the microphone for a predetermined time interval.

Clause 45: A viral disinfection method comprises operating a viral disinfection light source as set forth in any one of Clauses 27-44 to emit the light into an environment for human occupancy. Clause 46: The viral disinfection method of Clause 45 wherein the environment for human occupancy is a room, a ground vehicle cabin, an aircraft cabin, or a train compartment. Clause 47: The viral disinfection method of any one of Clauses 45-46 wherein the operating includes pulsing the emitted light. Clause 48: The viral disinfection method of any one of Clauses 45-47 wherein the operating includes modulating the emitted light based on occupancy of the environment for human occupancy detected using an occupancy sensor.

The following statements provide additional disclosure.

Statement 1: A multispectral light source for disinfection, in which the multispectral light source comprises a plurality of light sources with different disinfection peak wavelengths wherein each disinfection peak wavelength is effective for disinfection, and electronics configured to drive the plurality of light sources to emit light at the different disinfection peak wavelengths.

Statement 2: The multispectral light source of Statement 1 wherein the multispectral light source is configured to emit light into an environment for human occupancy to inactivate one or more pathogens in the environment for human occupancy. The light emitted by the multispectral light source is effective to produce an actinic dose at a target plane in the environment of 30 J/m$^2$ or less over an eight hour period, wherein the target plane is 2.1 meters or closer to a floor of the environment for human occupancy.

Statement 3: The multispectral light source of any one of Statements 1-2 wherein the multispectral light source is configured to emit light into an environment for human occupancy to inactivate one or more pathogens in the environment for human occupancy, and the irradiation of the light emitted into the environment for human occupancy by the multispectral light source is effective to achieve at least 90% inactivation of the one or more pathogens in the environment within 8 hours or less.

Statement 4: The multispectral light source of any one of Statements 1-3 wherein the plurality of light sources with different disinfection peak wavelengths include at least one UV-A light source with a disinfection peak wavelength in the UV-A range and at least one UV-C light source with a disinfection peak wavelength in the UV-C range. Statement 5: The multispectral light source of Statement 4 wherein the at least one UV-C light source with a disinfection peak wavelength in the UV-C range includes a first UV-C light source with a disinfection peak wavelength $\lambda_1$ in the UV-C range and a second UV-C light source with a disinfection peak wavelength $\lambda_2$ in the UV-C range, where $\lambda_1$ and $\lambda_2$ are different wavelengths in the UV-C range. Statement 6: The multispectral light source of any one of Statements 4-5 wherein the multispectral light source does not include a UV-B light source emitting in the UV-B range.

Statement 7: The multispectral light source of any one of Statements 1-6 wherein the electronics include an actinic dose budget parser configured to control the plurality of sets of LEDs to emit the different disinfection peak wavelengths to output a predetermined spectrum optimized to inactivate a specific target pathogen or class of pathogens.

Statement 8: The multispectral light source of any one of Statements 1-7 wherein the different disinfection peak wavelengths are discrete peak wavelengths and a total emission intensity of the multispectral light source outside of the discrete peak peaks is less than 40% of the total intensity emitted by the multispectral light source.

Statement 9: The multispectral light source of Statement 1 wherein the plurality of light sources with different disinfection peak wavelengths comprise a plurality of sets of LEDs wherein each set of LEDs includes one or more LEDs emitting at a respective disinfection peak wavelength, and the electronics include an actinic dose budget parser comprising an electronic processor programmed to control the plurality of sets of LEDs to emit the different disinfection peak wavelengths to output a predetermined spectrum optimized to inactivate a specific target pathogen or class of pathogens.

Statement 10: A multispectral light source for disinfection, in which the multispectral light source comprises: one or more UV-C light sources emitting ultraviolet light in a UV-C range, and one or more UV-A light sources emitting ultraviolet light in a UV-A range. Statement 11: The multispectral light source of Statement 10 further comprising one or more white light sources emitting white light providing illumination. Statement 12: The multispectral light source of Statement 11 further comprising a single fixture in which the one or more UV-C light sources, the one or more UV-A light sources, and the white light sources are mounted. Statement 13: The multispectral light source of Statement 11 further comprising a main fixture in which the one or more UV-A light sources and the white light sources are mounted, and an auxiliary fixture in which the one or more UV-C light sources are mounted. Statement 14: The multispectral light source of Statement 13 wherein the main fixture includes a connector and the auxiliary fixture is connected to receive electrical power from the main fixture via the connector.

Statement 15: The multispectral light source of any one of Statements 10-14 further comprising electronics programmed to control the one or more UV-C light sources and the one or more UV-A light sources to control a total actinic dose emitted by the combination of the one or more UV-C light sources and the one or more UV-A light sources.

Statement 16: A disinfection method comprises emitting light in the UV-C range into an occupied space, and emitting light outside of the UV-C range that is effective for inactivating at least one target pathogen into the occupied space. Statement 17: The disinfection method of Statement 16 wherein the emitting of the light outside of the UV-C range that is effective for inactivating the at least one target pathogen into the occupied space comprises emitting light in the UV-A range into the occupied space. Statement 18: The disinfection method of any one of Statements 16-17 wherein the emitting of the light outside of the UV-C range that is effective for inactivating the at least one target pathogen into the occupied space comprises emitting light in the violet range into the occupied space. Statement 19: The disinfection method of any one of Statements 16-18 wherein the emitting of the light outside of the UV-C range that is effective for inactivating the at least one target pathogen into the occupied space comprises emitting light in the infrared range into the occupied space. Statement 20: The disinfection method of any one of Statements 16-19 wherein the emitting of the UV-C light into the occupied space and the emitting of the light outside of the UV-C range that is effective for inactivating the at least one target pathogen into the occupied space are performed simultaneously.

The present disclosure has been described with reference to exemplary embodiments. Modifications and alterations may occur to others upon reading and understanding the preceding detailed description. It is intended that the present disclosure be construed as including all such modifications and alterations insofar as they come within the scope of the appended claims or the equivalents thereof.

The invention claimed is:

1. A disinfection system comprising:
  a fixture comprising:
    at least one light source configured to emit light into an environment for human occupancy to inactivate one or more pathogens in the environment for human occupancy, each light source comprising one or more UV-C LEDs disposed on a UV-C reflective board, the one or more UV-C LEDs configured to emit the light including an inactivating portion in a range of 230 nanometers to 280 nanometers, and one or more UV-A LEDs configured to emit the light including an inactivating portion in a range of 320 nanometers to 380 nanometers; and
    a manual control;
  wherein the light emitted by the at least one light source is effective to produce an actinic dose at a target plane in the environment of 30 J/m$^2$ or less over a pre-defined time period, wherein the target plane is a floor of the environment for human occupancy and the UV-C reflective board is configured to reflect UV-C light towards the target plane;
  wherein the actinic dose comprises a UV-C actinic dose fraction produced by the one or more UV-C LEDs and a UV-A actinic dose fraction produced by the one or more UV-A LEDs, and the manual control has (1) a virus inactivation setting in which the UV-C actinic dose fraction is greater than the UV-A actinic dose fraction and (2) a bacteria inactivation setting in which the UV-A actinic dose fraction is greater than the UV-C actinic dose fraction; and
  wherein the disinfection system does not include an imaging sensor.

2. The disinfection system of claim 1 wherein the irradiation of the light emitted into the environment for human occupancy by the at least one light source is effective to achieve at least 90% inactivation of the one or more pathogens in the environment within 8 hours or less.

3. The disinfection system of claim 1 wherein the environment for human occupancy is:
  a room having a ceiling, a floor, and walls, and the fixture is configured for mounting on the ceiling; or
  a ground vehicle cabin, an aircraft cabin, or a train compartment.

4. The disinfection system of claim 1 wherein the UV-C reflective board has a reflectance greater than 50% for the inactivating portion of the emitted light in the range of 230 nanometers to 280 nanometers.

5. The disinfection system of claim 1 wherein the UV-C reflective board is coated with an ePTFE layer.

6. The disinfection system of claim 1 wherein the at least one light source is configured to emit the light as pulsed light having a peak irradiance that is at least 1.5 times a time-averaged irradiance emitted by the at least one light source.

7. The disinfection system of claim 1 wherein the at least one light source does not include a heat sink.

8. A disinfection system comprising:
  a plurality of UV-C LEDs configured to emit UV-C light into an environment for human occupancy to inactivate one or more pathogens in the environment for human occupancy, the UV-C light including an inactivating portion in a range of 230 nanometers to 280 nanometers, wherein the plurality of UV-C LEDs is not controlled based on an imaging sensor; and
  an optical component arranged to reflect the UV-C light emitted by the plurality of UV-C LEDs toward the environment for human occupancy;
  a plurality of UV-A LEDs configured to emit UV-A light into an environment for human occupancy to inactivate one or more pathogens in the environment for human occupancy, the UV-A light including an inactivating portion in a range of 320 nanometers to 380 nanometers; and an electronic processor programmed to control the plurality of UV-C LEDs and the plurality of UV-A LEDs based on a control input having;
  (1) a virus inactivation setting causing the electronic processor to increase a UV-C actinic dose fraction output by the plurality of UV-C LEDs over a UV-A actinic dose fraction output by the plurality of UV-A LEDs, and
  (2) a bacteria inactivation setting causing the electronic processor to increase the UV-A actinic dose fraction output by the plurality of UV-A LEDs over the UV-C actinic dose fraction output by the plurality of UV-C LEDs;
  wherein the plurality of UV-C LEDs and the plurality of UV-A LEDs are mounted on a ceiling of the environment for human occupancy.

9. The disinfection system of claim 8 wherein the UV-C light has its peak wavelength in a range of 240 nanometers to 280 nanometers.

10. The disinfection system of claim 8 wherein UV-C light is effective to produce an actinic dose at a target plane in the environment for human occupancy of 30 J/m² or less over an eight hour period, wherein the target plane is a horizontal plane 2.1 meters or more from a floor of the environment for human occupancy.

11. The disinfection system of claim 8 wherein:
  the disinfection system does not include a UV-B light source emitting in the UV-B range.

12. The disinfection system of claim 8 wherein the optical component is arranged to shape the UV-C light emitted by the plurality of UV-C LEDs to form a spatial irradiance distribution on a plane in the environment for human occupancy in which every point on the plane has irradiance exceeding 50% of a maximum irradiance at any point on the plane in the environment for human occupancy.

13. The disinfection system of claim 8 wherein the plurality of UV-C LEDs does not include a spectral filter.

14. The disinfection system of claim 6 wherein the pulsed light comprises pulses having pulse width of 1 second or less and pulse spacing of at least 10 seconds.

15. The disinfection system of claim 8 wherein the ceiling of the environment for human occupancy includes a ceiling troffer and the UV-C LEDs are attached to an outside of the ceiling troffer.

16. A disinfection system comprising:
  a plurality of light sources each comprising one or more UV-C LEDs configured to emit UV-C light into a room for human occupancy having a ceiling and a floor to inactivate one or more viral pathogens in the room, the UV-C light including an inactivating portion in a range of 230 nanometers to 280 nanometers, and one or more UV-A LEDs configured to emit UV-A light into the room for human occupancy to inactivate one or more bacterial pathogens in the room, the UV-A light including an inactivating portion in a range of 320 nanometers to 380 nanometers; and
  an electronic processor programmed to implement an actinic dose budget processor controlling the outputs of the UV-C LEDs and the UV-A LEDs based on a control input to emphasize viral pathogen inactivation over bacterial pathogen inactivation or to emphasize bacterial pathogen inactivation over viral pathogen inactivation;
  wherein the light sources are mounted to the ceiling of the room and the light sources are arranged as a rectilinear array distributed across the ceiling of the room with spacings between the light sources of the rectilinear array configured to produce an actinic dose at the floor of the room of 30 J/m² or less over a pre-defined time period and to ensure that no portion of the floor of the room receives less than 50% of an irradiance received at a location of maximum irradiance on the floor of the room;
  wherein the disinfection system does not include an imaging sensor.

17. The disinfection system of claim 16 wherein the spacings between the light sources of the rectilinear array are 1.15 times a distance from the light sources to the floor of the room or less.

18. The disinfection system of claim 1, wherein the fixture is a first auxiliary fixture, and further comprising:
  a main fixture including white-light LEDs and a connector; and
  an electrical cable connecting the first auxiliary fixture with the connector of the main fixture.

19. The disinfection system of claim 18 further comprising:
  a second auxiliary fixture including the one or more UVA-LEDs; and
  a second electrical cable;
  wherein the main fixture includes a second connector and the second electrical cable connects the second auxiliary fixture with the second connector of the main fixture.

20. The disinfection system of claim 8 wherein the UV-C LEDs emit a Lambertian distribution, and the optical component is arranged to shape the UV-C light emitted by the plurality of UV-C LEDs to form a more uniform spatial distribution throughout the volume of the environment for human occupancy than the Lambertian distribution emitted by the UV-C LEDs.

* * * * *